United States Patent
Fischer et al.

(10) Patent No.: US 7,511,122 B2
(45) Date of Patent: *Mar. 31, 2009

(54) HUMANIZED AND CHIMERIC ANTIBODIES SPECIFIC FOR LIPOTEICHOIC ACID OF GRAM POSITIVE BACTERIA

(75) Inventors: Gerald Walter Fischer, Bethesda, MD (US); Richard F. Schuman, Gaithersburg, MD (US); Hing Wong, Weston, FL (US); Jeffrey R. Stinson, Brookville, MD (US)

(73) Assignees: Henry M. Jackson Foundation for the Advancement of Military Medicine, Rockville, MD (US); Altor BioScience Corporation, Miramar, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/193,440

(22) Filed: Aug. 1, 2005

(65) Prior Publication Data

US 2006/0002939 A1    Jan. 5, 2006

Related U.S. Application Data

(63) Continuation of application No. 10/601,171, filed on Jun. 23, 2003, which is a continuation of application No. 09/097,055, filed on Jun. 15, 1998, now Pat. No. 6,610,293.

(60) Provisional application No. 60/049,871, filed on Jun. 16, 1997.

(51) Int. Cl.
C12P 21/08 (2006.01)
C07K 16/00 (2006.01)
A61K 39/395 (2006.01)
G01N 33/574 (2006.01)
C12P 21/04 (2006.01)
C07H 21/04 (2006.01)

(52) U.S. Cl. ............ 530/387.3; 530/387.9; 530/388.1; 530/388.22; 424/133.1; 424/139.1; 424/141.1; 424/143.1; 435/69.6

(58) Field of Classification Search ................ None
See application file for complete search history.

(56) References Cited

U.S. PATENT DOCUMENTS

| | | |
|---|---|---|
| 4,027,010 A | 5/1977 | Kiselev et al. |
| 4,197,290 A | 4/1980 | Yoshida |
| 4,235,869 A | 11/1980 | Schwarzberg |
| 4,425,330 A | 1/1984 | Norcross et al. |
| 4,460,575 A | 7/1984 | d'Hinterland |
| 4,482,483 A | 11/1984 | Curry et al. |
| 4,596,769 A | 6/1986 | Shockman et al. |
| 4,719,290 A | 1/1988 | Curry et al. |
| 4,732,757 A | 3/1988 | Stolle et al. |
| 4,744,982 A | 5/1988 | Hunter et al. |
| 4,761,283 A | 8/1988 | Anderson |
| 4,789,735 A | 12/1988 | Frank et al. |
| 4,830,852 A | 5/1989 | Marburg et al. |
| 4,888,279 A | 12/1989 | Zeiger |
| 4,902,616 A | 2/1990 | Fournier et al. |
| 4,954,449 A | 9/1990 | Hunter et al. |
| 5,034,515 A | 7/1991 | Proctor et al. |
| 5,043,267 A | 8/1991 | Richards |
| 5,055,455 A | 10/1991 | Pier et al. |
| 5,153,312 A | 10/1992 | Porro |
| 5,175,096 A | 12/1992 | Hook et al. |
| 5,354,654 A | 10/1994 | Ligler et al. |
| 5,440,014 A | 8/1995 | Hook et al. |
| 5,505,945 A | 4/1996 | Gristina et al. |
| 5,530,101 A * | 6/1996 | Queen et al. |
| 5,530,102 A | 6/1996 | Gristina et al. |
| 5,538,733 A | 7/1996 | Emery et al. |
| 5,545,721 A | 8/1996 | Caroll et al. |
| 5,571,511 A | 11/1996 | Fischer |
| 5,624,904 A | 4/1997 | Krieger et al. |
| 5,652,217 A | 7/1997 | Hook et al. |

(Continued)

FOREIGN PATENT DOCUMENTS

| | | |
|---|---|---|
| EP | 0 724 016 A1 | 7/1996 |
| WO | WO 89/00999 | 2/1989 |
| WO | WO-90/03398 | 4/1990 |
| WO | WO-93/09811 | 5/1993 |
| WO | WO 93/17044 | 9/1993 |
| WO | WO-93/019373 | 9/1993 |
| WO | WO 94/11026 | 5/1994 |
| WO | WO 96/09321 | 3/1996 |
| WO | WO 96/23896 | 8/1996 |
| WO | WO 96/39518 | 12/1996 |
| WO | WO 97/26010 | 7/1997 |

OTHER PUBLICATIONS

Fundamental Immunology, William E. Paul ed., 3rd Edition, pp. 292-295, 1993.*

(Continued)

*Primary Examiner*—David J. Blanchard
(74) *Attorney, Agent, or Firm*—Lahive & Cockfield, LLP; Amy E. Mandragouras, Esq.; Megan E. Williams, Esq.

(57) ABSTRACT

The present invention encompasses monoclonal and chimeric antibodies that bind to lipoteichoic acid of Gram positive bacteria. The antibodies also bind to whole bacteria and enhance phagocytosis and killing of the bacteria in vitro and enhance protection from lethal infection in vivo. The mouse monoclonal antibody has been humanized and the resulting chimeric antibody provides a previously unknown means to diagnose, prevent and/or treat infections caused by gram positive bacteria bearing lipoteichoic acid. This invention also encompasses a peptide mimic of the lipoteichoic acid epitope binding site defined by the monoclonal antibody. This epitope or epitope peptide mimic identifies other antibodies that may bind to the lipoteichoic acid epitope. Moreover, the epitope or epitope peptide mimic provides a valuable substrate for the generation of vaccines or other therapeutics.

79 Claims, 27 Drawing Sheets

U.S. PATENT DOCUMENTS

| | | | |
|---|---|---|---|
| 5,770,208 | A | 6/1998 | Fattom et al. |
| 5,840,846 | A | 11/1998 | Hook et al. |
| 5,851,535 | A | 12/1998 | Jolivet-Reynaud |
| 5,955,074 | A | 9/1999 | Fischer |
| 5,955,078 | A | 9/1999 | Burnham et al. |
| 6,487,198 | B1 | 11/2002 | Pierson, Jr. |
| 6,610,293 | B1 | 8/2003 | Fischer |
| 6,939,543 | B2 | 9/2005 | Fischer et al. |
| 7,250,494 | B2 | 7/2007 | Stinson et al. |
| 2002/0031528 | A1 | 3/2002 | Fattom |
| 2002/0102262 | A1 | 8/2002 | Hook et al. |
| 2003/0103969 | A1 | 6/2003 | Ulevitch et al. |
| 2003/0119101 | A1 | 6/2003 | Burnie et al. |
| 2004/0013673 | A1 | 1/2004 | Fischer et al. |
| 2004/0052779 | A1 | 3/2004 | Stinson et al. |
| 2008/0019976 | A1 | 1/2008 | Stinson et al. |

OTHER PUBLICATIONS

Rudikoff et al. Proc. Natl. Acad. Sci. USA, 79:1979-1983, Mar. 1982.*
Coleman P. M. Research in Immunology, 145:33-36, 1994.*
Bendig M. M. Methods: A Companion to Methods in Enzymology, 1995; 8:83-93.*
Lederman et al. Molecular Immunology 28:1171-1181, 1991.*
Li et al. Proc. Natl. Acad. Sci. USA 77:3211-3214, 1980.*
Ahmad et al., "Sequential Release of Antigens from Chloroform-treated *Staphylococcus epidermidis*: Application Towards a Possible Vaccine," *J. App. Bacteriol.*, vol. 69, pp. 676-685 (1990).
Ahmed et al., "Preparation and Efficacy of Staphylococcal Vaccine by Sequential Release of Antigen from Solvent Treated Bacteria," *Soc. Appl. Bacter.*, vol. 67: xv (1989).
A. McGraw-Hill Publication, pp. 2-3 (Oct. 4, 1993). "Another Sepsis Drug Down -Immunex's TNF Receptor", *Biotechnology Newswatch*.
Archibald, A.R. et al., "Molecular arrangement of teichoic acid in the cell wall of *Staphylococcus lactis*," *Nature New Biology*, vol. 241, No. 105, pp. 29-31 (1973).
Baird-Parker, "The Basis for the Present Classification of Staphylococci and Micrococci, Recent Advances in Staphylococcal Research," *Ann. N.Y. Acad. Sci.*, 236: 7-14 (W. Yotis, ed. 1974).
Baker et al., "Intravenous Immune Globulin for the Prevention of Nosocomial Infection in Low Birth Weight Neonates", *New Eng. J. Med.*, 327: 213-19 (1992).
Baker et al., "Multicenter Trial of Intravenous Immunoglobulin (IVIG) to Prevent Late-Onset Infection in Preterm Infants: Preliminary Results," *Ped. Res.*, 25:275A (1989).
Bonnerjea et al., "Protein Purification: The Right Step at the Right Time," *Biotechnology*, 4:954-58 (1986).
Borrebaeck, *Antibody Engineering*, 2nd Ed., Oxford University Press, NY (1995).
Boslego et al., "Gonorrhea Vaccines," In Vaccines and Immunotherapy, Chap. 17, Cryz ed., Pergamon Press, pp. 211-223 (1991).
Brock, J.H., "Vaccination of the bovine against *Staphylocccal mastitis* with special reference to teichoic acid antibodies and the virulence of *S.aureus*," 1972-1973, publ. 1975, Index to Theses, vol. 23, p. 101, Reading University, citation only.
Campbell, "Monoclonal Antibodies and Immunosensor Technology," *Laboratory Techniques in Biochemistry and Molecular Biology* 23, Chapter 1, pp. 1-49 (1991).
Carozzi et al., "Response of CAPD Patients with a High Incidence of Peritonitis to Intraperitoneal Immunoglobulin Therapy," *Trans. Am. Soc. Artif. Intern. Organs.*, 34: 635-39 (1988).
Carruthers and Kabat, "Mediation of Staphylococcal Adherence to Mucosal Cells by Lipoteichoic Acid," *Infect Immun.*, 40:444-46 (1983).
Chugh, T.D. et al., "Adherence of *Staphylococcus epidermidis* to Fibrin-Platelet Clots In Vitro Mediated by Lipoteichoic Acid," *Infect. and Immun.*, vol. 58, pp. 315-319 (1990).
Cieslak et al., "Post-Immunization Antibodies to *S. epidermidis* are Broadly Reactive and Opsonic," *Ped. Research*, 31: 275A (1992).
Clapp et al., "Use of Intravenously Administered Immune Globulin to Prevent Nosocomial Sepsis in Low Birth Weight Infants: Report of a Pilot Study," *J. Pediatr.*, 115: 973-78 (1989).
Clark et al., "Opsonic Activity of Intravenous Immunoglobulin Preparations Against *Staphylococcus epidermidis*," *J. Clin. Pathol.*, 39:856-60 (1986).
Clark et al., "Opsonic Requirements of *Staphylococcus epidermidis*," *J. Med. Microbiol.*, 22:1-7 (1986).
Current Methods in Hybridoma Formation, Bartal et al. (ed.) *Methods of Hybridoma Formation*, Humana Press, Clifton, New Jersey (1987).
De Kimpe et al., "The Cell Wall Components Peptidoglycan and Lipoteichoic Acid From *S. aureus* Act in Synergy to Cause Shock and Multiple Organ Failure," *Proc. Nat. Acad. Sci. (USA)*, 92:10359. 63 (1995).
Derwent English language abstract of EP 0 724 016 AI, Abstract No. 96-343531/199635.
Dick et al., "Glycoconjugates of Bacterial Carbohydrate Antigens," *Contrib. Microbiol & Immunol.*, 10: 48-114 (1989).
Doyle et al., "Soluble Macromolecular Complexes Involving Bacterial Teichoic Acids," *J. Bacteriol.* 124: 341-47 (1975).
Ellis, "New Technologies for Making Vaccines," In Vaccines, Chap. 29, W.B. Saunders Co., at 56875 (Plotkin and Mortimer eds., 1988).
Endl, J. et al., "Chemical Composition and Structure of Cell Wall Teichoic Acids of Staphylococci," *Arch Microbiol*, vol. 135, 1983, pp. 215-223.
Espersen et al., "Enzyme-Linked Immunosorbent Assay for Detection of *Staphylococcus epidermidis* Antibody in Experimental *S. epidermidis* Endocarditis," *J. Clin. Microbiol.* 23: 339-42 (1986).
Espersen et al., "Solid-Phase Radioimmunoassay for IgG Antibodies to *Staphylococcus epidermidis*," *Arch. Intern. Med.* 147:689-93 (1987).
Espersen et al., *Staphylococcus aureus*, in "Antigen Detection to Diagnose Bacterial Infections," vol. II, CRC Press Inc., at 127-34 (Kohler, ed., 1986).
Espersen, F. et al., "Cross-Reactions Between *Staphylococcus epidermidis* and 23 Other Bacterial Species," *Acta path. microbial. scand.*, sect. B. vol. 89, 1981, pp. 253-260.
Etzioni et al., "Effect of an Intravenous Gammaglobulin Preparation on the Opsonophagocytic Activity of Preterm Serum Against Coagulase-Negative Staphylococci," *Acta. Paediatr. Scand.*, 79:156-61 (1990).
Fanaroff et al., "A Controlled Trial of Intravenous Immune Globulin to Reduce Nosocomial Infections in Very Low Birth Weight Infants," *New Eng. J. Med.* 330: 1107-13 (1992).
Fattom et al., "Capsular polysaccharide serotyping scheme for *Staphylococcus epidermidis*," *J. Clin. Microbiol.* 30: 3270-73 (1992).
Fattom et al., "Synthesis and Immunologic Properties in Mice of Vaccines Composed of *Staphylococcus aureus* Type 5 and Type 8 Capsular Polysaccharides Conjugated to *Pseudomonas aeruginosa* Exotoxin A," *Infect. & Immun.* 58(7): 2367-74 (1990).
Fischer et al., "Diminished Bacterial Defences with Intralipid," *Lancet* 2: 819-20 (1980).
Fischer et al., Directed Immune Globulin Enhances Survival in an Intralipid Induced Neonatal Model of Lethal *Staphylococcus epidermidis* Sepsis, *Ped. Res. Abstr.* Abstract No. 1670 (Apr. 1991).
Fischer et al., Improved Preparation of Lipoteichoic Acids, *Eur. J. Biochem.* 133:523-30 (1983).
Fischer et al., "Opsonic antibodies to *Staphylococcus epidermidis*: in vitro and in vivo studies using human intravenous immune globulin," *J. Inf. Dis.* 169: 324-29 (1994).
Fischer et al., "Therapeutic Uses of Intravenous Gammaglobulin for Pediatric Infections," *Ped. Clin. N. Amer.* 35: 517-33 (1988).
Fleer et al., "Opsonic Defense to *Staphylococcus epidermidis* in the Premature Neonate," *J. Infect. Dis.* 152: 930-37 (1985).
Fleer et al., "Septicemia due to Coagulase-negative Staphylococci in a Neonatal Intensive Care Unit: Clinical and Bacteriological Features and Contaminated Parenteral Fluids as a Source of Sepsis," *Pediatr. Infect. Dis.* 2: 426-31 (1983).
Fournier, *Staphylococcus aureus, Vaccines and Immunotherapy*, Ch. 13, pp. 166-177 (1991).

Freeman et al., "Association of Intravenous Lipid Emulsion and Coagulase-negative *Staphylococcal bacteremia* in Neonatal Intensive Care Units," *New Eng. J. Med.* 323: 301-08 (1990).

Gazmuri, R.J. et al., "The Ha-1a monoclonal antibody for gram negative sepsis (correspondence)," *New England Journal of Medicine*, vol. 325, No. 4, pp. 279-283 (1991).

Ginsburg, I. et al., "Lipoteichoic acid-antilipoteichoic acid complexes induce superoxide generation by human neutrophils," *Inflammation*, vol. 12, No. 6, pp. 525-548 (1988).

Gonzalez and Hill, "The Current Status of Intravenous Gammaglobulin Use in Neonates," *J. Ped. Infect. Dis.* 8:315-22 (1989).

Green et al., "Antigen-Specific Human Monoclonal Antibodies from Mice Engineered with Human Ig Heavy and Light Chain YACs," *Nat. Genet.* 7:13-21 (1994).

Gunn, "Comparative Virulence of Human Isolates of Coagulase-Negative Staphylococci Tested in an Infant Mouse Weight Retardation Model," *J. Clin. Microbiol.* 27: 507-11 (1989).

Hancock, "Bacterial Cell Surface Carbohydrates: Structure and Assembly," *Biochem. Soc. Trans.* 25:183-87 (1997).

Haque et al., "IgM-Enriched Intravenous Immunoglobulin Therapy in Neonatal Sepsis," *AJDC 142*: 1293-96 (1988).

Harlow et al., Monoclonal Antibodies, *Antibodies: A Laboratory Manual*, Cold Spring Harbor Laboratory, Chapter 6, 139-243 (1988).

Ichiman et al., "Induction of Resistance with Heat-Killed Unencapsulated Strains of *Staphylococcus epidermidis* Against Challenge with Encapsulated Strains of *Staphylococcus epidermidis*," *Microbiol. Immunol.* 33: 277-86 (1989).

Ichiman et al., "Cross Protection of Mice with the Smith Diffuse Strain of *Staphylococcus aureus* versus a type la Strain of Group B *Streptococci*," *Can. J. Microbiol.* 28: 726-32 (1982).

Ichiman et al., "Monocional IgM Antibody Protection in Mice Against Infection with an Encapsulated Strain of *Staphylococcus epidermidis*," *Can. J. Microbiol.* 37: 404-07 (1991).

Ichiman et al., "Protective Antibodies in Human Sera Against Encapsulated Strains of *Staphylococcus epidermidis*," *J. App. Bacter.* 63: 165-69 (1987).

Ichiman et al., "Relation of Human Serum Antibody Against *Staphylococcus epidermidis* Cell Surface Polysaccharide Detected by Enzyme-Linked Immunosorbent Assay to Passive Protection in the Mouse," *J. App. Bacter.* 71: 176-81 (1991).

Ichiman, Y. et al., "The Relationship of Capsular-type of s*Staphylococcus epidermidis* to Virulence and Induction of Resistance in the Mouse," *J. Appl. Bacteriology*, vol. 51, pp. 229-241 (1981).

Jackson, Dianne E. et al., "Monoclonal Antibodies to Immunodeterminants of Lipoteichoic Acids," *Infection and Immunity*, pp. 800-803, Mar. 1984.

Jendeberg et al., "Engineering of $FC_1$ and $FC_3$ From Human Immunoglobulin G to Analyse Subclass Specificity for Staphylococcal Protein A," *J. Immunol. Methods* 201:25-34 (1997).

Johnsen et al., "Studies on Polysaccharide C of *Staphylococcus epidermidis*," Acta Path. Microb. 83: 226-34 (1975).

Karakawa, W.W. et al., "Immunochemisty of an acidic antigen isolated from a *Staphylococcus aureus*," *Journal of Immunology*, vol. 114 (No. 1, pt. 2), pp. 310-315 (1975).

Klein, From Harmless Commensal to Invasive Pathogen, *New Eng. J. Med.* 323: 339-40 (1990).

Klesius, P.H. et al., "Human antibody response to a group A *Streptococcal teichoic acid*," *Canadian Journal of Microbiology*, vol. 20, No. 6, pp. 853-859 (1974).

Kojima, Yoshifumi et al., "Antibody to the Capsular Polysaccharide/ Adhesin Protects Rabbits against Catheter-Related Bacteremia Due to Coagulase-Negative *Staphylococci*," *J. of Infectious Diseases*, vol. 162, pp. 435-441 (1990).

Kotani et al., "Immunoadjuvant Activities of the Enzymatic Digests of Bacterial Cell Walls Lacking Immunoadjuvancy by Themselves," *Biken Journal* 20: 87-90 (1977).

Lamperi et al., "Intraperitoneal Immunoglobulin (1g) Treatment in Prophylaxis of Bacterial Peritonitis in CAPD," *Biomat., Art. Cells, Art. Org.* 15: 151-59 (1987).

Lee, "The Prospects for Developing a Vaccine Against *Staphylococcus aureus*," *Trends In Micro.* 4:162-66 (1996).

Lehner, T., "Monoclonal antibodies against micro-organisms", *Current Opinion in Immunology*, vol. 1, No. 3, pp. 462-466 (1989).

LoBuglio et al., "Mouse/Human Chimeric Monoclonal Antibody in Man: Kinetics and Immune Response," *P.N.A.S.* 86:4220-24 (1989).

Losnegard et al., "Immunochemical Studies on Polysaccharides from *Staphylococcus epidermidis*," *Acta Path. Microbiol. Scand.* 58: 493-500 (1963).

Low et al., "Mimicking Somatic Hypermutation: Affinity Maturation of Antibodies Displayed on Bacteriophage Using a Bacterial Mutator Strain," *J Mol Biol* 260:359-68 (1996).

Mancuso, G. et al., "Anti-Lipoteichoic Acid Antibodies Enhance Release of Cytokines by Monocytes Sensitized with Lipoteichoic Acid," *Infection and Immunity*, pp. 1470-1473 (1994).

McDermid et al., "A Porcine Model of *Staphylococcus epidermidis* Catheter-Associated Infection," *J. Infect. Dis.* 168: 897-903 (1993).

Modun et al., "A Preparation of *Staph. epidermidis* Vaccine by Enzymatic Digestion of Bacterial Cells," *J. Appl. Bacteriol.* 67:xv-xvi (1989).

Modun et al., "Cell Envelope Proteins of *Staphylococcus epidermidis* Grown in Vivo in a Peritoneal Chamber Implant," *Infect. & Immun.* 60: 2551-53 (1992).

Modun et al., "Extraction by Immune Complexing of Protective Antigens of *Staphylococcus epidermidis*; Application Towards Vaccine Preparation," *J. Appl. Bacteriol.* 67: xvi (1989).

Modun et al., "Staphylococci Express a Receptor for Human Treansferrin: Identification of a 42-Kilodalton Cell Wall Transferrin-Binding Protein," *Infect & Immun.* 62: 3850-58 (1994).

Naumova et al., "The Occurrence of Teichoic Acids in *Streptomycetes*, Abstract No. 3555r," *Chem. Abstracts* 93:342 abstract 3555r (1980).

Naumova, T.B. et al., "The Occurrence of Teichoic Acids in *Streptomycetes*," *Arch. Microbiol.*, vol. 126, pp. 71-75 (1980) (abstract only).

Nealon and Mattingly, "Role of Cellular Lipoteichoic Acids in Mediating Adherence of Serotype III Strains of Group B *Streptococci* to Human Embryonic, Fetal, and Adult Epithelial Cells," *Infect Immun.* 43:523-30 (1984).

NIH Consensus Conference, Intravenous Immunoglobulin: Prevention and Treatment of Disease, *JAMA* 264: 3189-93 (1990).

Niizuma, "Passive Protection Activities of Specific Human Immunoglobulin Against Strain ST67P of *Staphylococcus hyicus* Extracted from Pooled Human Sera," *St. Marianna Med. J.* 18:940-46 (1990) (original, translation, and certificate of translation).

Niizuma, "Passive Protective Activities of Specific Human Immunoglobulin Against Strain ST67P of *Staphylococcus hyicus* Extracted from Pooled Human Sera," *Chem. Abstracts* 115:181022v at 713 (1990).

Oeding et al., "Classification of Coagulase-Negative *Staphylococci* in the Diagnostic Laboratory," *ACTA Path. Microbiol. Scand.* 85:136-40 (1977).

Ohshima, Y et al, "Staphylococcal lipoteichoic acid, a potent simulant of immune cell porliferation, maturation and activation," *Zentralblatt Fur Bakteriologie- supplement*, 1994, issue 26, pp. 437-439.

Oshima et al., "Comparison of Cell Wall Teichoic Acid Fractions Isolated from Three Different Encapsulated Strains of *Staphylococcus epidermidis*," *Ann. Microbiol.* 135:353-65 (1984).

Osland et al., "Immunochemical Analysis of the Teichoic Acid from *Staphylococcus hyicus*," *ACTA Path. Microbiol. Scan.* 87: 165-69 (1979).

Osland, Arve et al., "Immunochemical Analysis of the Teichoic Acid from *Staphylococcus simulans*," *Acta path. microbial. scand.*, Sect. B, vol. 88, 1980, pp. 121-123.

Patrick et al., "Defining *Staphylococcus epidermidis* Cell Wall Proteins," *J. Clin. Microbiol.* 28:2757-60 (1990).

Patrick, "Coagulase-negative Staphylococci: Pathogens with Increasing Clinical Significance," *J. of Pediatr.* 116: 497-507 (1990).

PCT International Search Report, dated Sep. 9, 2003.

Peake, S., "Monoclonal antibodies-immunotherapy for the critically ill," *Anaesth Intens Care*, vol. 21, pp. 739-751 (1993).

Peterson et al., "Effect of Protein A on Staphylococcal Opsonization," *Infection and Immunity* 15:760-64 (1977).

Peterson et al., "Influence of Encapsulation on Staphylococcal Opsonization and Phagocytosis by Human Polymorphonuclear Leukocytes," *Infection and Immunity* 19:943-49 (1978).

Plaunt et al., "Identification of the Innate Human Immune Response to Surface-Exposed Proteins of Coagulase-Negative *Staphylococci*," *J. Clin. Microbiol.* 29: 857-61 (1991).

Poole-Warren et al., "The Role of Vaccination in the Prevention of *Staphylococcal peritonitis* in Continuous Ambulatory Peritoneal Dialysis," *Per. Dial. Int.* 13:176-77 (1993).

Prokop, O. et al., English title and descriptors, "The therapeutic use of anti-A-HP in the treatment of staphylococcal skin diseases as a result of the affinity of the hetero," *ACTA biologica et medica Germanica*, vol. 24, No. 3, pp. 19-23 (1970) (German article).

Quie et al., "Defective Phagocytosis of *Staphylococci*," *Ann. N. Y. Acad. Sci.* 236:233-43 (1974).

Raynor, Robert H. et al., "Lipoteichoic Acid Inhibition of Phagocytosis of *Staphylococcus aureus* by Human Polymorphonuclear Leukocytes", *Clinical Immunology and Immunopathology*, vol. 19, pp. 181-189 (1981).

Robbins et al., "Polysaccharide-Protein Conjugates: A New Generation of Vaccines," *J. Infect. Dis.* 161:821-32 (1990).

Roitt, *Essential Immunology*, Blackwell Scientific Publication, Oxford England, Chap. 4, at 55-68 (1988).

Romero-Vivas et al., "Mortality Associated with Nosocomial Bacteremia due to Methicillin-Resistant *Staphylococcus aureus*," *Clin. Infect. Dis.* 21:1417-23 (1995).

Salton, "The Bacterial Cell Envelope—A Historical Perspective," in J.-M. Ghuyson and R. Hakenbeck (Ed.), *Bacterial Cell Wall*, Elsevier Science BV, Amsterdam, pp. 1-22 (1994).

Santos et al., "Functional Leukocyte Administration in Protection Against Experimental Neonatal Infection," *Pediatr. Res.* 14: 1408-1410 (1980).

Schwab et al., "Increased Adherence of *Staphylococcus aureus* From Cystic Fibrosis Lungs to Airway Epithelial Cells," *Am. Rev. Respir. Dis.* 148:365-69 (1993).

Shaio et al., "Effect of Immune Globulin Intravenous on Opsonization of Bacteria by Classic and Alternative Complement Pathways in Premature Serum," *Ped. Res.* 25: 634-40 (1989).

Shulman et al., "A Better Cell Line for Making Hybridomas Secreting Specific Antibodies," *Nature* 276:269-70 (1978).

Siber, "Immune Globulin to Prevent Nosocomial Infections," *New Eng. J. Med.* 327:269-71 (1992).

Smith et al., "Characterization of Cell Envelope Proteins of *Staphylococcus epidermidis* Curtured on Human Perioneal Dialysate," *Infect. & Immun.* 59: 617-24 (1991).

Stashenko, P. et al., "Effect of monoclonal antibodies against lipoteichoic acid from the oral bacterium *Streptococcus mutans* on its adhesin and plaque-accumulation in vitro," *Archives of oral biology*, vol. 31, No. 7, pp. 455-461 (1986).

Sutcliffe, I.C. et al., "Atypical Lipoteichoic Acids of Gram-Positive Bacteria," *J. Bacteriology*, vol. 173, No. 22, pp. 7065-7069 (1991).

Sutherland, Separation and Purification of Bacterial Antigens, Handbook of Experimental Immunology, 3rd ed., at. 2.1-2.17 (D.M. Weir, ed., 1978).

Takada et al., "Molecular and Structural Requirements of a Lipoteichoic Acid From *Enterococcus hirae* ATCC 9790 for Cytokine-Inducing, Antitumor, and Antigenic Activities," *Infection and Immunity* 63:57-65 (1995).

Takeda et al., "Protection against endocarditis due to *Staphylococcus epidermidis* by immunization with capsular polysaccharide/adhesin," *Circulation* 84: 2539-46 (1991).

Teti et al., "Adherence of Group B Streptococci to Adult and Neonatal Epithelial Cells Mediated by Lipoteichoic Acid," *Infect Immun.* 55:3057-64 (1987).

Thörig et al., "Effect of Immunization on the Induction and Course of Experimental *Streptococcus sanguis* and *Staphylococcus epidermidis* Endocarditis," *Infection* 8: 267-74 (1980).

Timmerman et al., "Characterisation and Functional Aspects of Monoclonal Antibodies Specific for Surface Proteins of Coagulase-Negative *Staphylococci*," *J. Med. Microbiol.* 35: 65-71 (1991).

Timmerman et al., "Characterization of a Proteinaceous Adhesin of *Staphylococcus epidermidis* which Mediates Attachment to Polystyrene," *Infect & Immun.* 59: 4187-92 (1991).

Tojo et al., "Isolation and Characterization of a Capsular Polysaccharide Adhesin from *Staphylococcus epidermidis*," *J. Infect. Dis.* 157:713-22 (1988).

Van Bronswijk et al., "Heterogeneity in Opsonic Requirements of *Staphylococcus epidermidis*: Relative Importance of Surface Hydrophobicity, Capsules and Slime," *Immunol.* 67: 81-86 (1989).

Verbrugh et al., "Opsonic Recognition of *Staphylococci* Mediated by Cell Wall Peptidoglycan: Antibody-Independent Activation of Human Complement and Opsonic Activity of Peptidoglycan Antibodies," *J. Immunol.* 124: 1167-73 (1980).

Verhoef et al., "Opsonic Requirements for Staphylococcal phagocytosis," *Immunology* 33:191-97 (1977).

Verhoef et al., "*Staphylococcus epidermidis* Endocarditis and *Staphylococcus epidermidis* Infection in an Intensive Care Unit," *Scand. J. Infect. Dis.* Supp. 41: 56-63 (1983).

Wadström, "Molecular Aspects of Bacterial Adhesion, Colonization, and Development of Infections Associated with Biomaterials," *J. Invest. Surgery* 2:353-60 (1989).

Wagner et al., "Antibodies Generated from Human Immunoglobulin Miniloci in Transgenic Mice," *Nuc. Acids Res.* 22:1389-93 (1994).

Wagner et al., "The Diversity of Antigen-Specific Monoclonal Antibodies from Transgenic Mice Bearing Human Immunoglobulin Gene Miniloci," *Eur J Immunol* 24:2672-81 (1994).

Waldvogel, "*Staphylococcus aureus* (Including Toxic Shock Syndrome)," In Mandell, G.L. et al. (ed.) *Principles and Practices of Infectious Diseases*, Third Edition, Churchill Livingstone, New York, Ch. 173, pp. 1489-1510 (1990).

Wedrén, On Chronic Prostatitis with Special Studies of *Staphylococcus epidermidis*, *Scand. J. Urololgy & Nephrol.* Supp. 123: 3-36 (1989).

Weisman et al., "Intravenous Immune Globulin Prophylaxis on Late-Onset Sepsis in Premature Neonates," *J. Ped.* 125:922-30 (1994).

Wergeland et al., "Antibodies to Various Bacterial Cell Wall Peptidoglycans in Human and Rabbit Sera," *J. Clin. Microbiol.* 25: 540-45 (1987).

West, Timothy E. et al., "Detection of Anti-Teichoic Acid Immunogloublin G Antibodies in Experimental *Staphylococcus epidermidis* Endocarditis," *Infection and Immunity*, vol. 42, No. 3, 1983, pp. 1020-1026.

Wheat, Analysis of Hexosamines in Bacterial Polysaccharides by Chormatographic Procedures, *Methods in Enzymology* 8: 60-78 (1966).

Wilcox et al., "Variation in the Expression of Cell Envelope Proteins of Coagulase-Negative Staphylococci Cultured Under Iron-Restricted Conditions in Human Peritoneal Dialysate," *J. Gen. Microbiol.* 137: 2561-70 (1991).

Wilkinson, "Immunochemistry of Purified Polysaccharide Type Antigens of Group B Streptococcal Types Ia, Ib, and Ic," *Infect. Immun.* 11: 845-52 (1975).

Williams et al., "Protein Antigens of *Staphylococcus epidermidis* Grown Under Iron-Restricted Conditions in Human Peritoneal Dialysate," *FEMS Mircrobiol. Ltrs.* 50:29-33 (1988).

Winter et al., "Making Antibodies by Phage Display Technology," *Annu. Rev. Immunol.* 12:433-55 (1994).

Wu, T.C. et al., "Chemical characterization of a new surface antigenic polysaccharide from a mutant of *Staphylococcus aureus*," *Journal of Bacteriology*, vol. 108, No. 2, pp. 874-884 (1971).

Yamada et al., "Possible Common Biological and Immunological Properties for Detecting Encapsulated Strains of *Staphylococcus epidermidis*," *J. Clin. Microbiol.* 26:2167-72 (1988).

Yang et al., "Mechanisms of Bacterial Opsonization by Immune Globulin Intravenous: Correlation of Complement Consumption with Opsonic Activity and Protective Efficacy," *J. Infect. Dis.* 159:701-07 (1989).

Yoshida et al., "Cross Protection Between a Strain of *Staphylococcus epidermidis* and Eight Other Species of Coagulase-Negative *Staphylococci*," *Can. J. Microbiol.* 34:913-15 (1988).

Yoshida et al., "Cross Protection Between an Encapsulated Strain of *Staphylococcus hyicus* and Encapsulated Strains of *Staphylococcus aureus*," *J. App. Bact.* 65:491-99 (1988).

Yoshida et al., "Immunological Response to a Strain of *Staphylococcus epidermidis* in the Rabbit: Production of Protective Antibody," *J. Med. Microbial.* 11: 371-77 (1977).

Yoshida et al., "Mouse Virulent Strain of *Staphylococcus epidermidis*," *Jap. J. Microbiol.* 20:209-17 (1976).

Yoshida et al., "Staphylococcal Capsular Vaccine for Preventing Mastitis in Two Herds in Georgia," *J. Dairy Sci. 67*: 620-27 (1984).

Yoshitomi, "Serological Differentiation of Strains of *Staphylococcus epidermidis* by the Soft Agar Technique," *St. Marianna Med. J.* 17:166-74 (1989).

Aasjord, Per et al., "Antibodies to Lipoteichoic Acid from *Staphylococcus aureus*," *Acta path, microbiol. immunol. scand.*, Sect. C, vol. 93:245-250 (1985).

Hamada, Shigeyuki et al., "Characterization of a Monoclonal Antibody Specific for Lipoteichoic Acid from Various Gram-Positive Bacteria," *Microbiol. Immunol.*, vol. 28(9):1009-1021 (1984).

Roitt, Ivan M. et al., Chapts. 1, 24, Immunology, Third Edition, Mosby, pp. 1.1-1.12, 24.1-24.12 (1993).

Drabick, J. et al., "A Monoclonal Antibody Directed Against Lipoteichoic Acid by Streptococcus Pyogenes is Broadly Cross-reactive with Many Gram Positive Organisms," Abstracts of the General Meeting of the American Society for Microbiology, the Society, Washington, DC, US, vol. 93;109 (1993).

Winter, Greg et al., "Humanized antibodies," *Immunology Today*, vol. 14(6):243-246 (1993).

Ausubel, F., Short Protocols in Molecular Biology, Greene Publishing Assoc., pp. iii-xvi (1989).

Dale, J.B. et al., "Passive protection of mice against group A streptococcal pharyngeal infection by lipoteichoic acid," *J. Infect. Dis.*, vol. 169(2):319-323 (1994).

Gennaro, Alfonso R., Remington's Pharmaceutical Science, 18th Edition, Mack Publishing Company, Easton, Pennsylvania, pp. xv-xvi (1990).

Sambrook, J. et al., Molecular Cloning, a Laboratory Manual, 2nd Edition, Cold Spring Harbor Laboratory Press, pp. xi-xxxviii (1989).

Wergeland, Heidrun I, et al., "Antibodies to Staphylococcal Peptidoglycan and Its Peptide Epitopes, Teichoic Acid, and Lipoteichoic Acid in Sera from Blood Donors and Patients with Staphylococcal Infections," *Journal of Clinical Microbiology*, vol. 27(6):1286-1291 (1989).

* cited by examiner

6MER.SEQ

| | 10 | 20 | 30 | | | |
|---|---|---|---|---|---|---|
| 41:13.6mer2-1 | GGGGCTCATG | CGGATAGGGT | TTATGGGGCC | SEQ | ID | NO:4 |
| 61 | G A H | A D R V | Y G A | SEQ | ID | NO:5 |
| 42:14.6mer2-2 | GGGGCTCATG | CGGATAGGGT | TTATGGGGCC | SEQ | ID | NO:4 |
| 65 | G A H | A D R V | Y G A | SEQ | ID | NO:5 |
| 43:15.6mer2-3 | GGGGCTCATG | CGGATAGGGT | TTATGGGGCC | SEQ | ID | NO:4 |
| 66 | G A H | A D R V | Y G A | SEQ | ID | NO:5 |
| 44:16.6mer2-4 | GGGA-TCATG | CGGATAGGGT | TTATGGGGCC | SEQ | ID | NO:6 |
| 62 | G ? H | A D R V | Y G A | SEQ | ID | NO:7 |
| 45:17.6mer2-5 | GGGGCTCATG | CGGATAGGGT | TTATGGGGCC | SEQ | ID | NO:4 |
| 67 | G A H | A D R V | Y G A | SEQ | ID | NO:5 |
| 46:18.6mer2-6 | GGGGCTCATG | CGGATAGGGT | TTATGGGGCC | SEQ | ID | NO:4 |
| 68 | G A H | A D R V | Y G A | SEQ | ID | NO:5 |
| 47:19.6mer2-7 | GGGGCTCATG | CGGATAGGGT | TTATGGGGCC | SEQ | ID | NO:4 |
| 69 | G A H | A D R V | Y G A | SEQ | ID | NO:5 |
| 48:20.6mer2-8 | GGGGCTCATG | CGGATAGGGT | TTATGGGGCC | SEQ | ID | NO:4 |
| 70 | G A H | A D R V | Y G A | SEQ | ID | NO:5 |
| 49:21.6mer2-9 | GGGGCTCATG | CGGATAGGGT | TTATGGGGCC | SEQ | ID | NO:4 |
| 71 | G A H | A D R V | Y G A | SEQ | ID | NO:5 |
| 51:23.6mer2-11 | GGGGCTCATG | CGGATAGGGT | TTATGGGGCC | SEQ | ID | NO:4 |
| 72 | G A H | A D R V | Y G A | SEQ | ID | NO:5 |
| 52:24.6mer2-12 | GGGGCTCATG | CGGATAGGGT | TTATGGGGCC | SEQ | ID | NO:4 |
| 73 | G A H | A D R V | Y G A | SEQ | ID | NO:5 |
| 53:25.6mer2-13 | GGGGCTCATG | CGGATAGGGT | TTATGGGGCC | SEQ | ID | NO:4 |
| 74 | G A H | A D R V | Y G A | SEQ | ID | NO:5 |
| 54:26.6mer2-14 | GGGGCTCATG | CGGATAGGGT | TTATGGGGCC | SEQ | ID | NO:4 |
| 75 | G A H | A D R V | Y G A | SEQ | ID | NO:5 |
| 55:27.6mer2-15 | GGGGCTCATG | CGGATAGGGT | TTATGGGGCC | SEQ | ID | NO:4 |
| 76 | G A H | A D R V | Y G A | SEQ | ID | NO:5 |
| 56:28.6mer2-16 | GGGGCTCATG | CGGATAGGGT | TTATGGGGCC | SEQ | ID | NO:4 |
| 77 | G A H | A D R V | Y G A | SEQ | ID | NO:5 |
| 58:30.6mer2-18 | GGGGCTCATG | CGGATAGGGT | TTATGGGGCC | SEQ | ID | NO:4 |
| 78 | G A H | A D R V | Y G A | SEQ | ID | NO:5 |
| 59:31.6mer2-19 | GGGGCTCATG | CGGATAGGGT | TTATGGGGCC | SEQ | ID | NO:4 |
| 79 | G A H | A D R V | Y G A | SEQ | ID | NO:5 |
| 60:32.6mer2-20 | GGGGCTCATG | CGGATAGGGT | TTATGGGGCC | SEQ | ID | NO:4 |
| 80 | G A H | A D R V | Y G A | SEQ | ID | NO:5 |

*FIG. 5*

| 15MER2.SEQ | | 10 | 20 | 30 | 40 | 50 | 60 | |
|---|---|---|---|---|---|---|---|---|
| 50:07.15mer2-1/0 | GGGGCTTGGC | A(W) | ATTGGCGTCA | TCGTATTCCT | CTTCAGCTTG | CTGCTGGTCG | TGGGGCC | SEQ ID NO.8 |
| 70 | G A (W) | H W R H | R I P | L Q L | A A G R | G A | SEQ ID NO.9 |
| 52:09.15mer2-3/0 | GGGGCTCGTC | GGGATGGTAA | TTTTTCATT | TTTTTCATC | GTCGTTCAT | TGGGGCC | SEQ ID NO.10 |
| 72 | G A R | (H) G N | F (S) (H) | F F (H) | (R) S L I | G A | SEQ ID NO.11 |
| 53:10.15mer2-4/0 | GGGGCTTCGA | AGGCTTTGT | TAGTCATTCT | TATCGTCCTC | GGGGTTCGGC | TGGGGCC | SEQ ID NO.12 |
| 73 | G A (W) | (K) A L (F) | (S) (H) S | Y (R) P | R G S A | G A | SEQ ID NO.13 |
| 54:11.15mer2-5/0 | GGGGCTTGGC | ATTGGCGTCA | TCGTATTCCT | CTTCAGCTTG | CTGCTGGTCG | TGGGGCC | SEQ ID NO.14 |
| 74 | G A R | H W R H | R I P | L Q L | A A G R | G A | SEQ ID NO.15 |
| 56:13.15mer2-7/0 | GGGGCTTGGC | ATTGGCGTCA | TCGTATTCCT | CTTCAGCTTG | CTGCTGGTCG | TGGGGCC | SEQ ID NO.16 |
| 76 | G A W | H W R H | R I P | L Q L | A A G R | G A | SEQ ID NO.17 |
| 57:14.15mer2-8/0 | GGGGCTTGGC | ATTGGCGTCA | TCGTATTCCT | CTTCAGCTTG | CTGCTGGTCG | TGGGGCC | SEQ ID NO.18 |
| 77 | G A W | H W R H | R I P | L Q L | A A G R | G A | SEQ ID NO.19 |
| 58:15.15mer2-9/0 | GGGGCTCAGG | TGGCTGTTTT | CTATCCCTCT | TTGGCTGATG | CTACTGAGCT | TGGGGCC | SEQ ID NO.20 |
| 78 | G A Q | V A V L | Y P P | L A D | A T E L | G A | SEQ ID NO.21 |
| 59:16.15mer2-10/0 | GGGGCTCGTC | GGGATGGTAA | TTTTTCATT | TTTTTCATC | GGTCGTTCAT | TGGGGCC | SEQ ID NO.22 |
| 79 | G A R | R H G N | F S H | F F H | R S L I | G A | SEQ ID NO.23 |
| 60:17.15mer2-11/0 | GGGGCTCGTC | GGGATGGTAA | TTTTTCATT | TTTTTCATC | GGTCGTTCAT | TGGGGCC | SEQ ID NO.24 |
| 80 | G A R | R H G N | F S H | F F H | R S L I | G A | SEQ ID NO.25 |
| 61:18.15mer2-12/0 | GGGGCTTGGC | GTATGTATTT | TTCTCATCGT | CATGCGCATC | TTCGTAGTCC | TGGGGCC | SEQ ID NO.26 |
| 81 | G A (W) | R M Y (F) | (S) (H) R | H A (H) | (L) R S P | G A | SEQ ID NO.27 |
| 62:19.15mer2-13/0 | GGGGCTTGGC | GTATGTATTT | TTCTCATCGT | CATGCGCATC | TTCGTAGTCC | TGGGGCC | SEQ ID NO.28 |
| 82 | G A W | R M Y F | S H R | H A H | L R S P | G A | SEQ ID NO.29 |
| 63:20.15mer2-14/0 | GGGGCTTGGC | GGAAGTATTT | TTCTTATCAT | CATGCGCATC | TTTGTAGTCC | TGGGGCC | SEQ ID NO.30 |
| 83 | G A W | R M Y F | S Y H | H A H | L C S P | G A | SEQ ID NO.31 |
| 64:21.15mer2-15/0 | GGGGCTTGGC | GTATGTATTT | TTCTCATCGT | CATGCGCATC | TTCGTAGTCC | TGGGGCC | SEQ ID NO.32 |
| 84 | G A W | R M Y F | S H R | H A H | L R S P | G A | SEQ ID NO.33 |
| 65:22.15mer2-16/0 | GGGGCTTGGC | GTATGTATTT | TTCTCATCGT | CATGCGCATC | TTCGTAGTCC | TGGGGCC | SEQ ID NO.34 |
| 85 | G A W | R M Y F | S H R | H A H | L R S P | G A | SEQ ID NO.35 |

FIG. 6A

.5MER2.SEQ

| | 10 | 20 | 30 | 40 | 50 | 60 | |
|---|---|---|---|---|---|---|---|
| 66:23.15mer2-17/0 86 | GGGGCTTGGC G A W | GTATGTATTT R M Y F | TTCTCATCGT S H R | CATGCCATC H A H | TTCGTAGTCC L R S P | TGGGCC G A | SEQ ID NO.36 SEQ ID NO.37 |
| 67:24.15mer2-18/0 87 | GGGGCTCGTC G A R | GGCATGGTAA R H G N | TTTTCTCAT F S H | TTTTTCATC F F H | GGTCGTTGAT R S L I | TGGGCC G A | SEQ ID NO.38 SEQ ID NO.39 |
| 68:25.15mer2-19/0 88 | GGGGCTTGGC C A W | ATTGGCGTCA H W R H | TCGTATTCCT R I P | CTTCAGCTTG L Q L | CTGCTGGTCG A A G R | TGGGCC G A | SEQ ID NO.40 SEQ ID NO.41 |
| 69:26.15mer2-20/0 89 | GGGGCTCGTC G A R | GGCATGGTAA R H G N | TTTTTCTCAT F S H | TTTTTCATC F F H | GGTCGTTGAT R S L I | TGGGCC G A | SEQ ID NO.42 SEQ ID NO.43 |

| 15MER1.SEQ | 10 | 20 | 30 | 40 | 50 | 60 | |
|---|---|---|---|---|---|---|---|
| 51:28.15mer1-2/0 67 | GGGGCTGATT G A D | CGATTACTTT W I T | TCATCGTCGT H R R | CATCATGATC H H D | GTGTTCTTTC V L S | TGGGGCC G A | SEQ ID NO.44 |
| 52:29.15mer1-3/0 68 | GGGGCTGGTT G A G | CGATTACTTT W I T | TCATCGTCGT H R R | CATCATGATC H H D | GTGTTCTTTC R V L S | TGGGGCC G A | SEQ ID NO.45 |
| 53:32.15mer1-6/0 65 | GGGGCTGGTT G A G | CGATTACTTT W I T | TCATCGTCGT H R R | CATCATGATC H H D | GTGTTCTTTC R V L S | TGGGGCC G A | SEQ ID NO.46 |
| 62:13.15mer1-7/0 66 | GGGGCTGGTT G A G | CGATTACTTT W I T | TCATCGTCGT H R R | CATCATGATC H H D | GTGTTCTTTC R V L S | TGGGGCC G A | SEQ ID NO.47 |
| 63:14.14mer1-8/0 67 | GGGGCTGGTT G A G | CGATTACTTT W I T | TCATCGTCGT H R R | CATCATGATC H H D | GTGTTCTTTC R V L S | TGGGGCC G A | |
| 64:15.15mer1-9/0 68 | GGGGCTGGTT G A G | CGATTACTTT W I T | TCATCGTCGT H R R | CATCATGATC H H D | GTGTTCTTTC R V L S | TGGGGCC G A | |
| 65:16.15mer1-10/0 69 | GGGGCTGGTT G A G | CGATTACTTT W I T | TCATCGTCGT H R R | CATCATGATC H H D | GTGTTCTTTC R V L S | TGGGGCC G A | |
| 56:17.15mer1-11/0 70 | GGGGCTGGTT G A G | CGATTACTTT W I T | TCATCGTCGT H R R | CATCATGATC H H D | GTGTTCTTTC R V L S | TGGGGCC G A | |
| 57:20.15mer1-12/0 71 | GGGGCTGGTT G A G | CGATTACTTT W I T | TCATCGTCGT H R R | CATCATGATC H H D | GTGTTCTTTC R V L S | TGGGGCC G A | |
| 58:29.15mer1-13/0 72 | GGGGCTGGTT G A G | CGATTACTTT W I T | TCATCGTCGT H R R | CATCATGATC H H D | GTGTTCTTTC R V L S | TGGGGCC G A | |
| 59:20.15mer1-14/0 73 | GGGGCTGGTT G A G | CGATTACTTT W I T | TCATCGTCGT H R R | CATCATGATC H H D | GTGTTCTTTC R V L S | TGGGGCC G A | |
| 70:21.15mer1-15/0 74 | GGGGCTGGTT G A G | CGATTACTTT W I T | TCATCGTCGT H R R | CATCATGATC H H D | GTGTTCTTTC R V L S | TGGGGCC G A | |
| 71:22.15mer1-16/0 75 | GGGGCTGGGA G A G | AGCTATGTT K A M | TAGTCATTCT E S H | TATCGTCATC Y R H | GGGGTCGGC G S A | TGGGGCC G A | SEQ ID NO.48 |
| 72:23.15mer1-17/0 76 | GGGGCTGGTT G A G | CGATTACTTT W I T | TCATCGTCGT H R R | CATCATGATC H H D | GTGTTCTTTC R V L S | TGGGGCC G A | SEQ ID NO.49 |

FIG. 7A

| 15MER1.SEQ | | 10 | 20 | 30 | 40 | 50 | 60 |
|---|---|---|---|---|---|---|---|
| 73:24.15mer1-18/0<br>77<br>74:25.15mer1-19/0<br>78<br>75:26.15mer1-20/0<br>79 | | GGGGCTGGTT<br>G A G<br>GGGGCTGGTT<br>G A G<br>GGGGCTGGTT<br>G A G | CGATTACTTT<br>W I T F<br>CGATTACTTT<br>W I T F<br>CGATTACTTT<br>W I T F | TCATCGTCGT CATCATGATC<br>H R R H H D<br>TCATCGTCGT CATCATGATC<br>H R R H H D<br>TCATCGTCGT CATCATGATC<br>H R R H H D | GTGTTCTTTC<br>R V L S<br>GTGTTCTTTC<br>R V L S<br>GTGTTCTTTC<br>R V L S | TGGGGCC<br>G A<br>TGGGGCC<br>G A<br>TGGGGCC<br>G A | |

FIG. 7B

| masterlist | 10 | 20 | 30 | 40 | 50 | 60 | 70 | |
|---|---|---|---|---|---|---|---|---|
| 51:15mer 1st.1 57 | GGGGCTGATT | CGATTACTTT | TCATCGTCGT | CATCATGATC | GTGTTCTTTC | TGGGGCC | 16/17 | SEQ ID NO.50 |
|  | G A D | W I T F | H R R | H H D | R V L S | G A | | SEQ ID NO.51 |
| 90:15mer 1st.2 91 | GGGGCTAGTC | GTCATATGCT | TGCTCGGTGG | TCGGCGTTGC | TTGCGTTTC | TGGGGCC | 1/10 | SEQ ID NO.52 |
|  | G A S | R H M L | A R W | S R L | L A V P | G A | | SEQ ID NO.53 |
| 71:15mer 1st.16 85 | GGGGCTGGGA | AGGCTATGTT | TAGTCATTCT | TATCGTCATC | GCGGTTCGGC | TGGGGCC | 1/17 | SEQ ID NO.54 |
|  | G A G | K A M F | S H S | Y R H | R G S A | G A | | SEQ ID NO.55 |
| 92:15mer 2nd.1 98 | GGGGCTTGGC | ATTGGCGTCA | TCGTATTCCT | CTTCAGCTTG | CTGCTGGTCG | TGGGGCC | 5/18 | SEQ ID NO.56 |
|  | G A W | H W R H | R I P | L Q L | A A G R | G A | | SEQ ID NO.57 |
| 93:15mer 2nd.3 99 | GGGGCTCGTC | GGCATGGTAA | TTTTTCTCAT | TTTTTCATC | GGTCGTTGAT | TGGGGCC | 6/18 | SEQ ID NO.58 |
|  | G A R | R H G N | F S H | F F H | R S L I | G A | | SEQ ID NO.59 |
| 94:15mer 2nd.4 100 | GGGGCTTGGA | AGGCTTTGTT | TAGTCATTCT | TATCCTCCTC | GGGGTTCGGC | TGGGGCC | 1/18 | SEQ ID NO.60 |
|  | G A W | X A L F | S H S | Y R P | R G S A | G A | | SEQ ID NO.61 |
| 95:15mer 2nd.9 101 | GGGGCTTGGC | TGGCTGTTTT | GTATCCTCCT | TTGGCTGATG | CTACTGAGCT | TGGGGCC | 1/18 | SEQ ID NO.62 |
|  | G A Q | V A V L | Y P P | L A D | A T E L | G A | | SEQ ID NO.63 |
| 96:15mer 2nd.12 102 | GGGGCTTGGC | GTATGTATTT | TTCTCATCGT | CATGCGCATC | TTCGTAGTCC | TGGGGCC | 6/18 | SEQ ID NO.64 |
|  | G A W | R M Y F | S H R | H A H | L R S P | G A | | SEQ ID NO.65 |
| 97:6mer 2nd.1 103 | GGGGCTCATG | CGGATAGGGT | TTATGGGCC | | | | 18/18 | SEQ ID NO.66 |
|  | G A H | A D R V | Y G A | | | | | SEQ ID NO.67 |

FIG. 8

MOUSE HEAVY CHAIN "FRONT" PRIMERS
JSS1
5'-ATTTCAGGCCCAGCCGGCCATGGCCGARGTRMAGCTKSAKGAGWC-3'   SEQ ID NO.68
JSS2
5'-ATTTCAGGCCCAGCCGGCCATGGCCGARGTYCARCTKCARCARYC-3'   SEQ ID NO.69
JSS3
5'-ATTTCAGGCCCAGCCGGCCATGGCCCAGGTGAAGCTKSTSGARTC-3'   SEQ ID NO.70
JSS4
5'-ATTTCAGGCCCAGCCGGCCATGGCCGAVGTGMWGCTKGTGGAGWC-3'   SEQ ID NO.71
JSS8
5'-ATTTCAGGCCCAGCCGGCCATGGCCCAGGTBCARCTKMARSARTC-3'   SEQ ID NO.72

MOUSE HEAVY CHAIN "BACK" PRIMERS
JS160
5'-GCTGCCACCGCCACCTGMRGAGACDGTGASTGARG-3'   SEQ ID NO.73
JS161
5'-GCTGCCACCGCCACCTGMRGAGACDGTGASMGTRG-3'   SEQ ID NO.74
JS162
5'-GCTGCCACCGCCACCTGMRGAGACDGTGASCAGRG-3'   SEQ ID NO.75

MOUSE LIGHT CHAIN LEADER "FRONT" PRIMERS
PMC12
5'-CCCGGGCCACCATGGAGACAGACACACTCCTG-3' SEQ ID NO.76
PMC13
5'-CCCGGGCCACCATGGATTTTCAAGTGCAGATTTC-3' SEQ ID NO.77
PMC14
5'-CCCGGGCCACCATGGAGWCACAKWCTCAGGTC-3' SEQ ID NO.78
PMC15
5'-CCCGGGCCACCATGKCCCCWRCTCAGYTTCTKG-3' SEQ ID NO.79
PMC55
5'-CCCGGGCCACCATGAAGTTGCCTGTTAGGCTG-3' SEQ ID NO.80

MOUSE LIGHT CHAIN "BACK" PRIMER
OKA57
5'-GCACCTCCAGATGTTAACTGCTC-3' SEQ ID NO. 81

"96-110" SPECIFIC PRIMERS
96110HF2
5'-TAATATGCGACACAGGTGTCCACTCCCGAAGTGATGCTGGTGGAGWCTG-3' SEQ ID NO.82
96100HB
5'-TTATAGAATTCTGAGGAGACGGTGAGTGAG-3' SEQ ID NO.83
96110BLF
5'-TTAGGCGATAGCGTTCTCTCCCAGTCTCC-3' SEQ ID NO.84
96110BLB
5'-GTAACCGTTCGAAAGTGTACTTACGTTTTATTCCAGCATGGTCC-3' SEQ ID NO.85

96-110 ANTI-STAPH (HAY) HEAVY CHAIN VARIABLE REGION (TYPE IIIA)

```
GAAGTGATGCTGGTGGAGTCTGGTGGAGGATTGGTGCAGCCTCTCAGCCTCTGATTCACCTTCAAT
 E  V  M  L  V  E  S  G  G  G  L  V  Q  P  K  G  S  L  K  L  S  C  A  A  S  G  F  T  F  N

AACTACGCCATGAAT TGGGTCCGCCAGGCTCCAGGAAAAGGGTTTGAATGGGTTGCT
 N  Y  A  M  N   W  V  R  Q  A  P  G  K  G  L  E  W  V  A

CGCATAAGAAGTAAAAGTAATAATTATGCAACATTTTATGCCGATTCAGTGAAAGAC
 R  I  R  S  K  S  N  N  Y  A  T  F  Y  A  D  S  V  K  D

AGGTTCACCATCTCCAGAGATGATTCACAAAGCATGCTCTATCTGCAAATGAACAACTTGAAAACTGAGGACACAGCCATGTATTACTGTGTGAGA
 R  F  T  I  S  R  D  D  S  Q  S  M  L  Y  L  Q  M  N  N  L  K  T  E  D  T  A  M  Y  Y  C  V  R

CGGGGGGGCTTCAGGGATTGACTATGCCTATGGACTAC TGGGGTCAAGGAACCTCACTCACCGTCTCCTCA SEQ ID NO. 86
 R  G  A  S  G  I  D  Y  A  M  D  Y    W  G  Q  G  T  S  L  T  V  S  S              SEQ ID NO. 87
```

FIG. 12A 96-110 ANTI-STAPH (HAY) LIGHT CHAIN VARIABLE REGION (TYPE VI)

```
CAAATTGTTCTCTCCAGTCTCCAGCAATCCTGTCTGCATCTCCAGGGGAAAAGGTCACAATGACTTGC
 Q  I  V  L  S  Q  S  P  A  I  L  S  A  S  P  G  E  K  V  T  M  T  C

AGGGCCAGTCAAGTGTAAATTACATGCAC
 R  A  S  S  V  N  Y  M  H

TGGTACCAGCAGAAGCCAGGATCCTCCCCCAAACCCTGGATTTCT GCCACATCCAACCTGGCTTCT
 W  Y  Q  Q  K  P  G  S  S  P  K  P  W  I  S   A  T  S  N  L  A  S

GGAGTCCCTGCTCGCTTCAGTGGCAGTGGGTCTGGGACCTCTTACTCTCTCACAATCAGCAGAGTGGAGGCTGAAGATGCTGCCACTTATTACTGC
 G  V  P  A  R  F  S  G  S  G  S  G  T  S  Y  S  L  T  I  S  R  V  E  A  E  D  A  A  T  Y  Y  C

CAGCAGTGGAGTAGTAACCCACCCACG TTCGGAGGGGGGACCATGCTGGAAATAAGA  SEQ ID NO. 88
 Q  Q  W  S  S  N  P  P  T   P  G  G  G  T  M  L  E  I  R       SEQ ID NO. 89
```

CDR REGIONS UNDERLINED

FIG. 12B

HUMANIZED AND CHIMERIC ANTIBODIES SPECIFIC FOR LIPOTEICHOIC ACID OF GRAM POSITIVE BACTERIA

CROSS REFERENCE TO RELATED APPLICATIONS

This application is a continuation of co-pending U.S. patent application Ser. No. 10/601,171, filed Jun. 23, 2003, which is a continuation of U.S. patent application Ser. No. 09/097,055, filed Jun. 15, 1998, now issued as U.S. Pat. No. 6,610,293, which claims the benefit of U.S. Provisional Patent Application Ser. No. 60/049,871, filed Jun. 16, 1997, which application is specifically incorporated herein by reference.

FIELD OF THE INVENTION

This invention in the fields of immunology and infectious diseases relates to antibodies that are specific for Gram positive bacteria, particularly to lipoteichoic acids exposed on the surface of the bacteria. The invention includes monoclonal and chimeric antibodies, as well as fragments, regions and derivatives thereof. This invention also relates to the epitope to which the antibodies of the invention bind as well as the sequences, fragments, and regions of the epitopes. Both the antibodies and peptides that encompass the epitope, and regions and fragments thereof, may be used for diagnostic, prophylactic and therapeutic applications.

BACKGROUND OF THE INVENTION

Man has long battled bacterial infections, and no one can doubt the tremendous successes obtained. Before the discovery and development of antibiotics, death due to a bacterial infection was frequently rapid and inevitable. Surgical procedures and sanitary conditions have vastly improved from the time when amputation was associated with a 50 percent mortality rate.

Nonetheless, the battle has not been won. Undoubtedly a significant part of the problem is that bacteria are the product of nearly 3 billion years of natural selection from which they have emerged as an immensely diverse group of organisms that colonize almost all parts of the world and its inhabitants. To begin to understand bacteria requires categorization, and the most fundamental categories for bacteria are their response to the Gram stain, yielding (for the most part) Gram positive bacteria and Gram negative bacteria.

The difference in response to the Gram stain results from differences in bacterial cell walls. The cells walls of Gram negative bacteria are made up of a unique outer membrane of two opposing phospholipid-protein leaflets, with an ordinary phospholipid in the inner leaflet but the extremely toxic lipopolysaccharide in the outer leaflet. The cell walls of Gram positive bacteria seem much simpler in comparison, containing two major components, peptidoglycan and teichoic acids plus additional carbohydrates and proteins depending on the species.

Of the Gram positive bacteria, one of the most common genera is *Staphylococcus*. Staphylococci commonly colonize humans and animals and are an important cause of human morbidity and mortality, particularly in hospitalized patients. Staphylococci are prevalent on the skin and mucosal linings and, accordingly, are ideally situated to produce both localized and systemic infections.

There are two main groups of Staphylococci divided according to the production of "coagulase," an enzyme that causes fibrin to coagulate and to form a clot: coagulase positive and coagulase negative. The coagulase positive *Staphylococcus* species most frequently pathogenic in humans is *Staphylococcus aureus*. *S. aureus* is the most virulent *Staphylococcus* and produces severe and often fatal disease in both normal and immunocompromised hosts. *Staphylococcus epidermidis* is the most common coagulase negative species.

In recent years, *S. epidermidis* has become a major cause of nosocomial infection in patients whose treatments include the placement of foreign objects such as cerebrospinal fluid shunts, cardiac valves, vascular catheters, joint prostheses, and other implants into the body. *S. epidermidis* and *S. aureus* are common causes of post-operative wound infections and *S. epidermidis* has also become a common cause of peritonitis in patients with continuous ambulatory peritoneal dialysis. In a similar manner, patients with impaired immunity and those receiving parenteral nutrition through central venous catheters are at high risk for developing *S. epidermidis* sepsis. (C. C. Patrick, J. Pediatr., 116:497 (1990)). *S. epidermidis* is now recognized as a common cause of neonatal nosocomial sepsis. Infections frequently occur in premature infants that have received parenteral nutrition which can be a direct or indirect source of contamination.

Staphylococcal infections are difficult to treat for a variety of reasons. Resistance to antibiotics is common and becoming more so. See L. Garrett, *The Corning Plague*, "The Revenge of the Germs or Just Keep Inventing New Drugs" Ch. 13, pgs. 411-456, Farrar, Straus and Giroux, N.Y., Eds. (1994). In one study, the majority of Staphylococci isolated from blood cultures of septic infants were multiply resistant to antibiotics (A. Fleer et al., Pediatr. Infect. Dis. 2:426 (1983)). A more recent study describes methicillin-resistant *S. aureus* (J. Romero-Vivas, et al., Clin. Infect. Dis. 21:1417-23 (1995)) and a recent review notes that the emergence of antibiotic resistance among clinical isolates makes treatment difficult (J. Lee., Trends in Micro. 4(4):162-66 (April 1996). Recent reports in the popular press also describe troubling incidents of antibiotic resistance. See *The Washington Post* "Microbe in Hospital Infections Show Resistance to Antibiotics," May 29, 1997; *The Washington Times*, "Deadly bacteria outwits antibiotics," May 29, 1997.

In addition, host resistance to Staphylococcal infections is not clearly understood. Opsonic antibodies have been proposed to prevent or treat Staphylococcal infections. See U.S. Pat. No. 5,571,511 to G. W. Fischer issued Nov. 5, 1996, specifically incorporated by reference. The microbial targets for these antibodies have been capsular polysaccharides or surface proteins. As to capsular polysaccharides, the immunization studies of Fattom et al., J. Clin. Micro. 30(12):3270-3273 (1992) demonstrated that opsonization was related to *S. epidermidis* type-specific anti-capsular antibody, suggesting that *S. epidermidis* and *S. aureas* have a similar pathogenesis and opsonic requirement as other encapsulated Gram positive cocci such as *Streptococcus pneumonia*. As to surface proteins, Timmerman, et al., J. Med. Micro. 35:65-71 (1991) identified a surface protein of *S. epidermidis* that was opsonic for the homologous strain used for immunization and for monoclonal antibody production. While other monoclonal antibodies were identified that bound to non-homologous *S. epidermidis* strains, only the monoclonal antibody produced to the homologous strain was opsonic and opsonization was enhanced only to the homologous strain but not to heterologous strains. Accordingly, based on the studies of Fattom et al., and Timmerman et al., and others in the field (and in contrast to our own studies), one would not expect that an antibody that is broadly reactive to multiple strains of *S. epidermidis* and to *S. aureus* would have opsonic activity against both. This is particularly true for antibodies that bind to both coagulase positive and coagulase negative Staphylococci.

Accordingly, there is a need in the art to provide monoclonal antibodies that can bind to *Staphylococcus* of both coagulase types and that can enhance phagocytosis and killing of the bacteria and thereby enhance protection in vivo. There is also a need in the art for the epitope of the site to which such antibodies can bind so that other antibodies with similar abilities can be identified and isolated.

There is a related need in the art for humanized or other chimeric human/mouse monoclonal antibodies. In recent well publicized studies, patients administered murine anti-TNF (tumor necrosis factor) monoclonal antibodies developed anti-murine antibody responses to the administered antibody. (Exley A. R., et al., Lancet 335:1275-1277 (1990)). This type of immune response to the treatment regimen, commonly referred to as the HAMA response, decreases the effectiveness of the treatment and may even render the treatment completely ineffective. Humanized or chimeric human/mouse monoclonal antibodies have been shown to significantly decrease the HAMA response and to increase the therapeutic effectiveness. See LoBuglio et al., P.N.A.S. 86:4220-4224 (June 1989).

SUMMARY OF THE INVENTION

To address these needs in the art, the present invention encompasses opsonic and protective monoclonal and chimeric antibodies that bind to lipoteichoic acid of Gram positive bacteria. The antibodies also bind to whole bacteria and enhance phagocytosis and killing of the bacteria in vitro and enhance protection from lethal infection in vivo. The mouse monoclonal antibody has been humanized and the resulting chimeric antibody provides a previously unknown means to diagnose, prevent and/or treat infections caused by gram positive bacteria bearing lipoteichoic acids. This invention also encompasses a peptide mimic of the lipoteichoic acid epitope binding site defined by the monoclonal antibody. This epitope or epitope peptide mimic identifies other antibodies that may bind to the lipoteichoic acid epitope. Moreover, the epitope or epitope peptide mimic provides a valuable substrate for the generation of vaccines or other therapeutics.

BRIEF DESCRIPTION OF THE DRAWINGS

FIG. 5 (SEQ ID NOS 4 and 5, and 6 and 7, respectively) provides a list of 18 resulting sequences for the 6mer library panning. SEQ ID NO designations are provided only for sequences not previously given a SEQ ID NO. Thus, the following identified nucleotide sequences all share the sequence listing designation of SEQ ID NO.4: 41:13.6mer2-1; 42:14.6mer2-2; 54:13.6mer2-3; 45:17.6mer2-5; 46:18.6mer2-6; 47:19.6mer2-7; 48:20.6mer2-8; 49:21.6mer2-9; 51:23.6mer2-11; 52:24.6mer2-12; 53:25.6mer2-13; 54:26.6mer2-14; 55:27.6mer2-15; 56:28.6mer2-16; 58:30.6mer2-18; 59:31.6mer2-19; and 60:32.6mer2-2. The corresponding amino acid sequences all share the sequence listing designation of SEQ ID NO 5.

FIGS. 6A and 6B (SEQ ID NOS 8-43, respectively) provide a list of the 18 resulting sequences for the second experiment 15mer library panning.

FIGS. 7A and 7B (SEQ ID NOS 44 and 45, and 46 and 47, and 48 and 49, respectively) provide a list of the 17 resulting sequences for the first experiment 15mer library panning. SEQ ID NO designations are provided only for sequences not previously given a SEQ ID NO. Thus, the following identified nucleotide sequences all share the sequence listing designation of SEQ ID NO. 46: 52:29.15mer1-3/0; 53:32.15mer1-6/0; 62:13.15mer1-7/0; 63:14.15mer1-8/0; 64:15.15mer1-9/0; 65:16.15mer1-10/0; 56:17.15mer1-11/0; 57:20.15mer1-12/0; 58:29.15mer1-13/0; 59:20.15mer1-14/0; 70:21.15mer1-15/0; 72:23.15mer1-17/0; 73:24.15mer1-18/0; 74:25.15mer1-19/0; and 75:26.15mer1-20/0. The corresponding amino acid sequences all share the sequence listing designation of SEQ ID NO. 47.

FIG. 8 (SEQ ID NOS 50-67, respectively) provides a master list compiled from the common resulting peptide sequences from all the pannings.

FIGS. 11A and 11B (SEQ ID NOS 68-85, respectively) list the oligonucleotide primers used.

FIG. 12A (SEQ ID NOS 86 and 87) provides the final consensus DNA and amino acid sequence of the heavy chain variable region. FIG. 12B (SEQ ID NOS 88 and 89) provides the final consensus DNA and amino acid sequence of the light chain variable region.

The underlined portions indicate the complementarity determining regions (CDRs).

Figure 13:
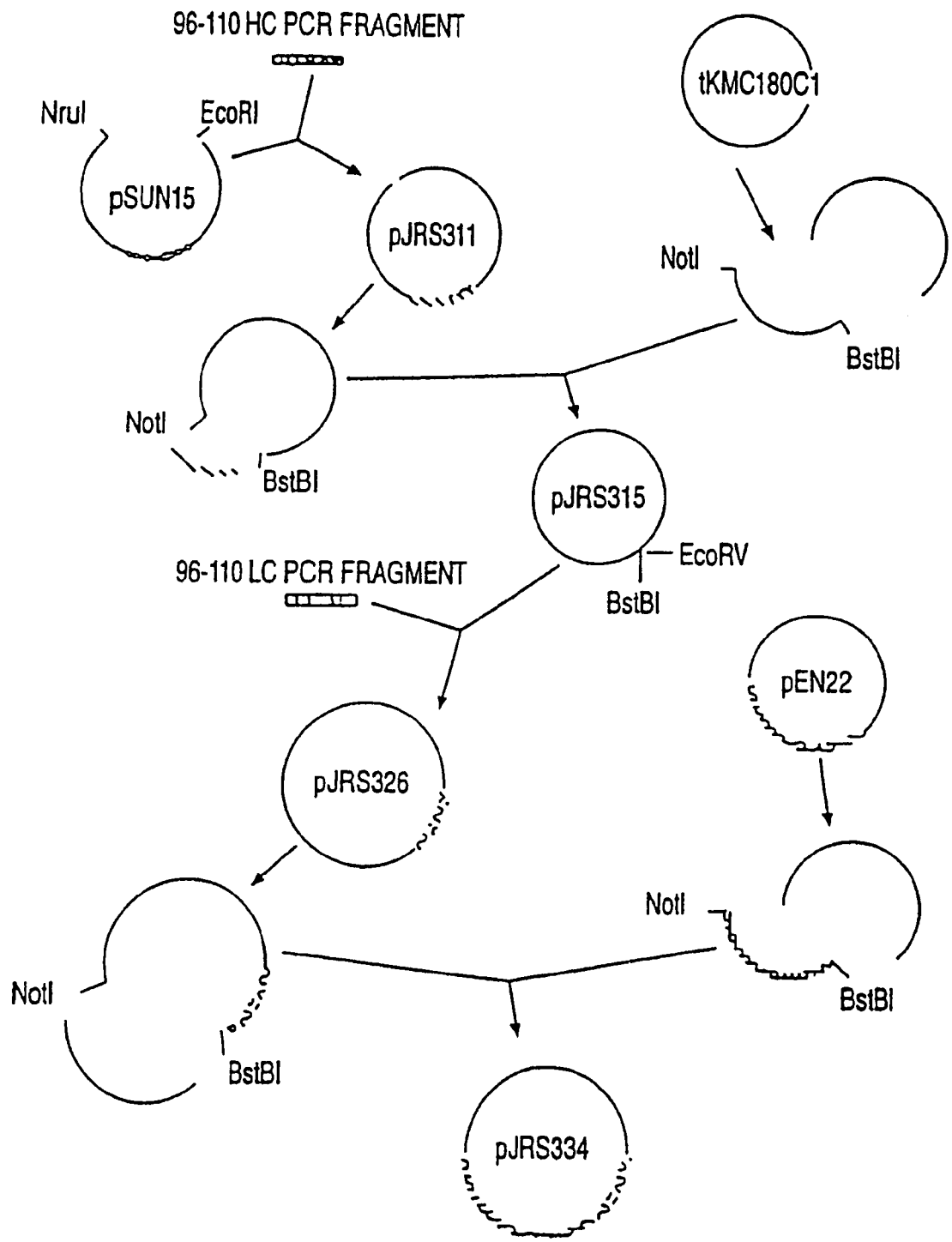

FIG. 13 demonstrates the re-amplification of the variable region gene fragments.

Figure 14:
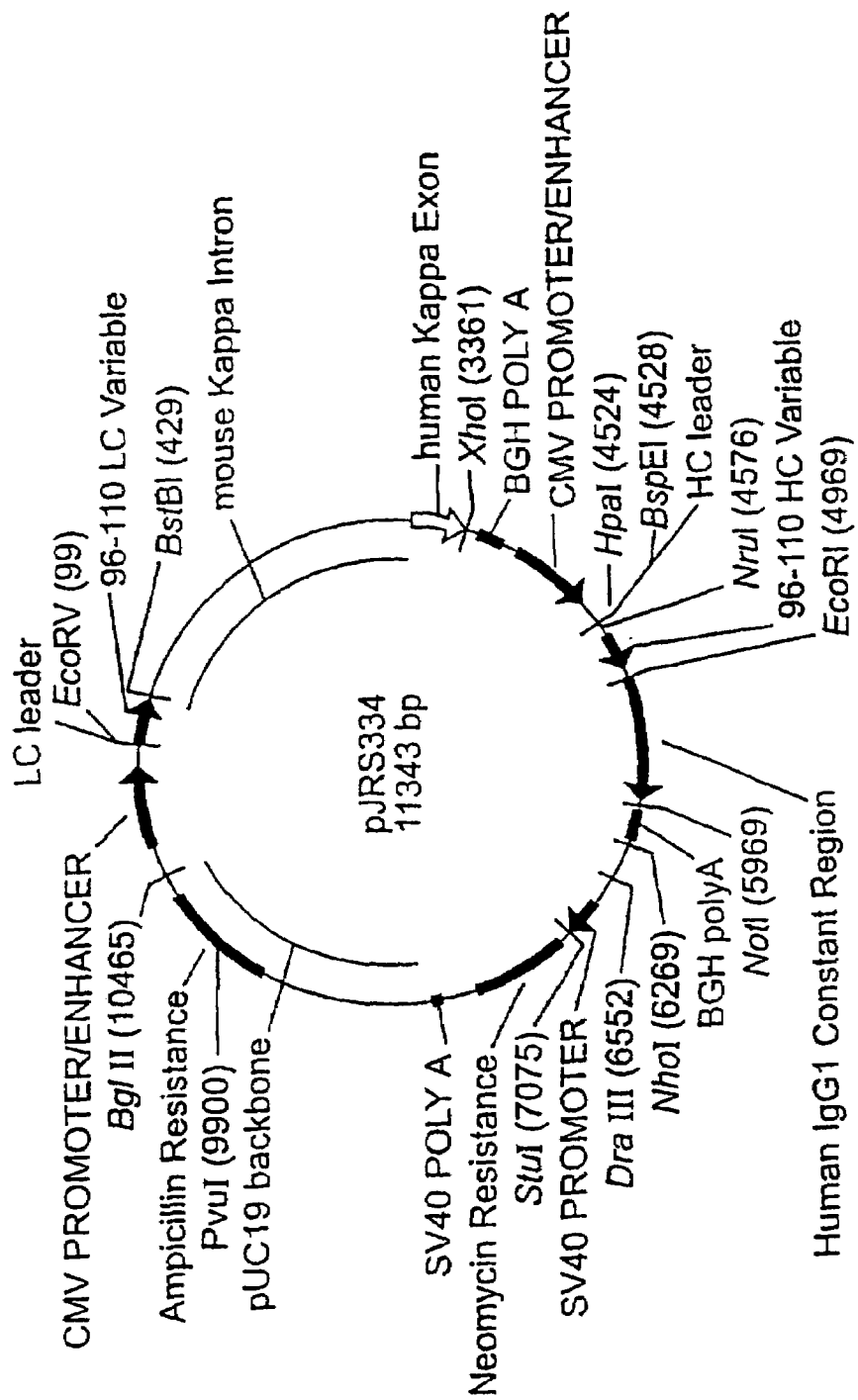

FIG. 14 sets forth the plasmid map for pJRS334.

Figure 15:
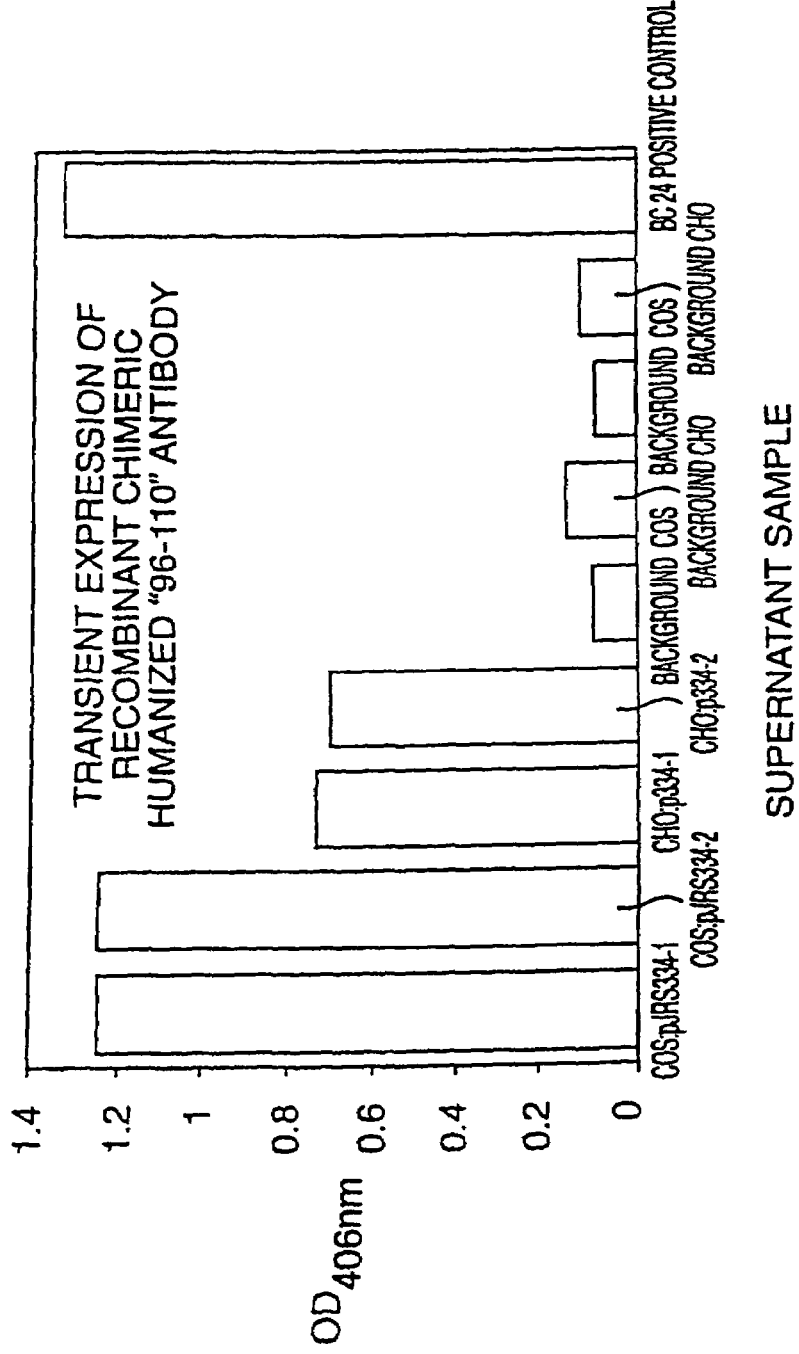

FIG. 15 provides the results of the antibody production assay, showing that the transfection of cells with the plasmid construct results in the production of a molecule containing both human IgG and kappa domains.

Figure 16:
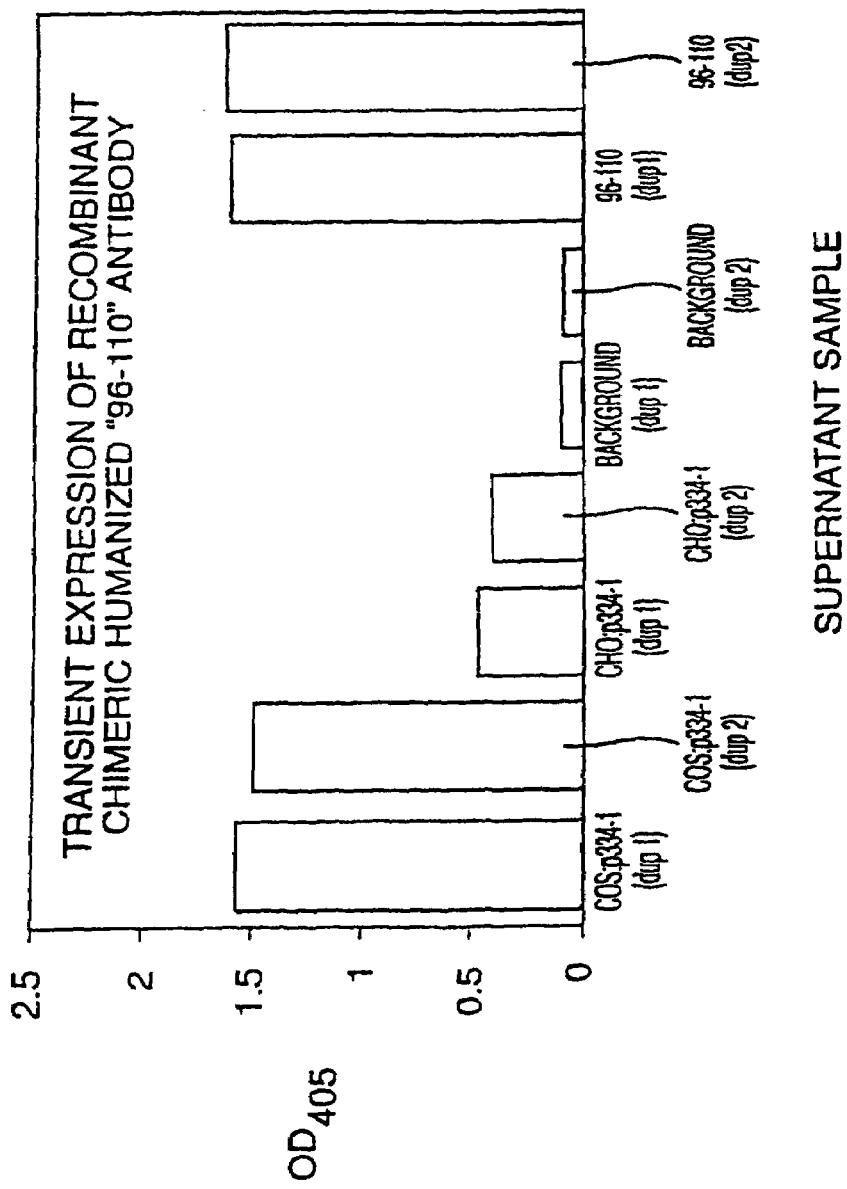

FIG. 16 provides the results of the activity assay, demonstrating that the transfection of cells with the plasmid construct results in the production of a molecule that binds to the Hay antigen.

Figure 17:
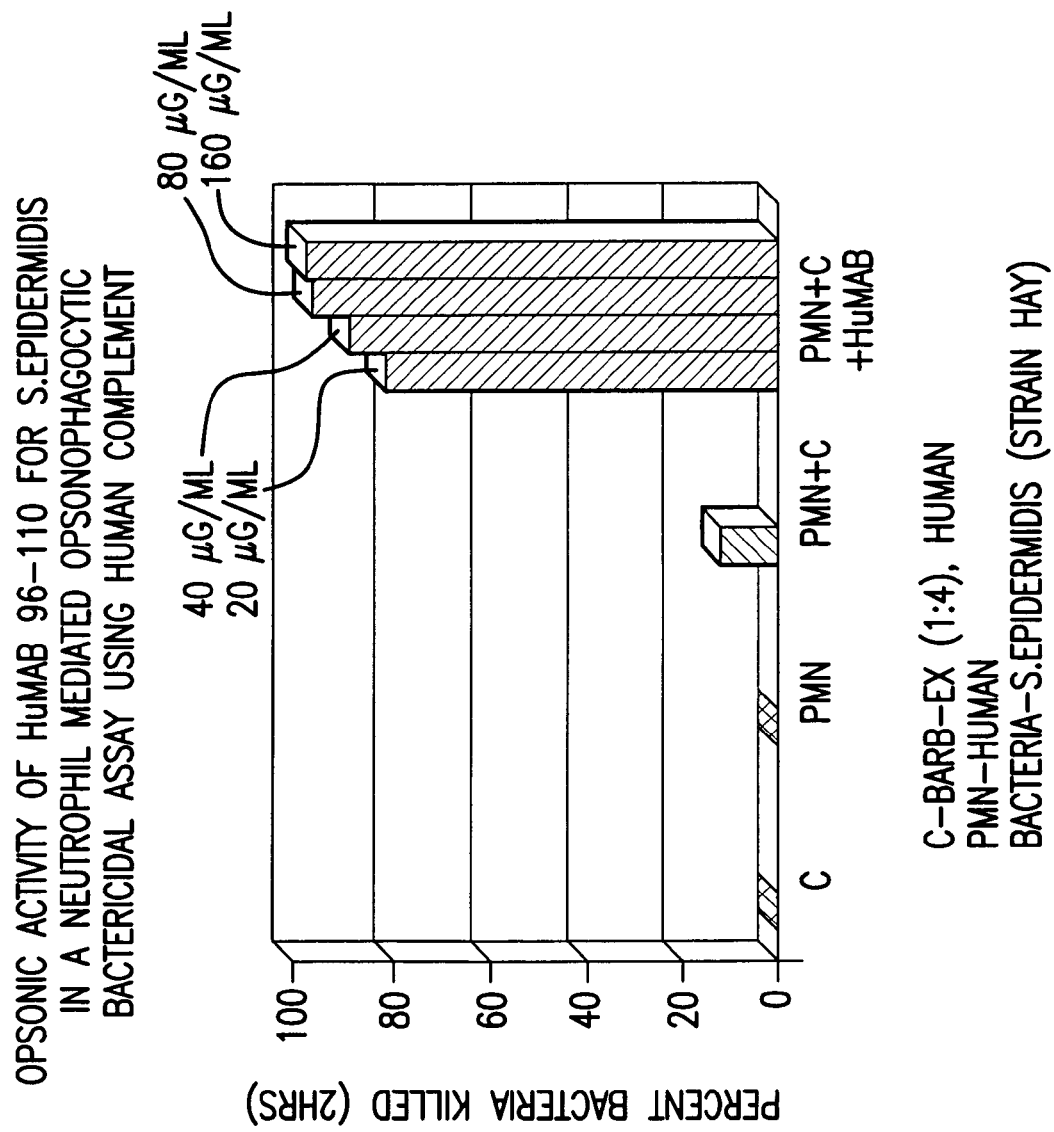

FIG. 17 depicts the opsonic activity of the chimeric monoclonal antibody 96-110 for *S. epidermidis* in a neutrophil mediated opsonophagocytic bactericidal assay.

Figure 18:
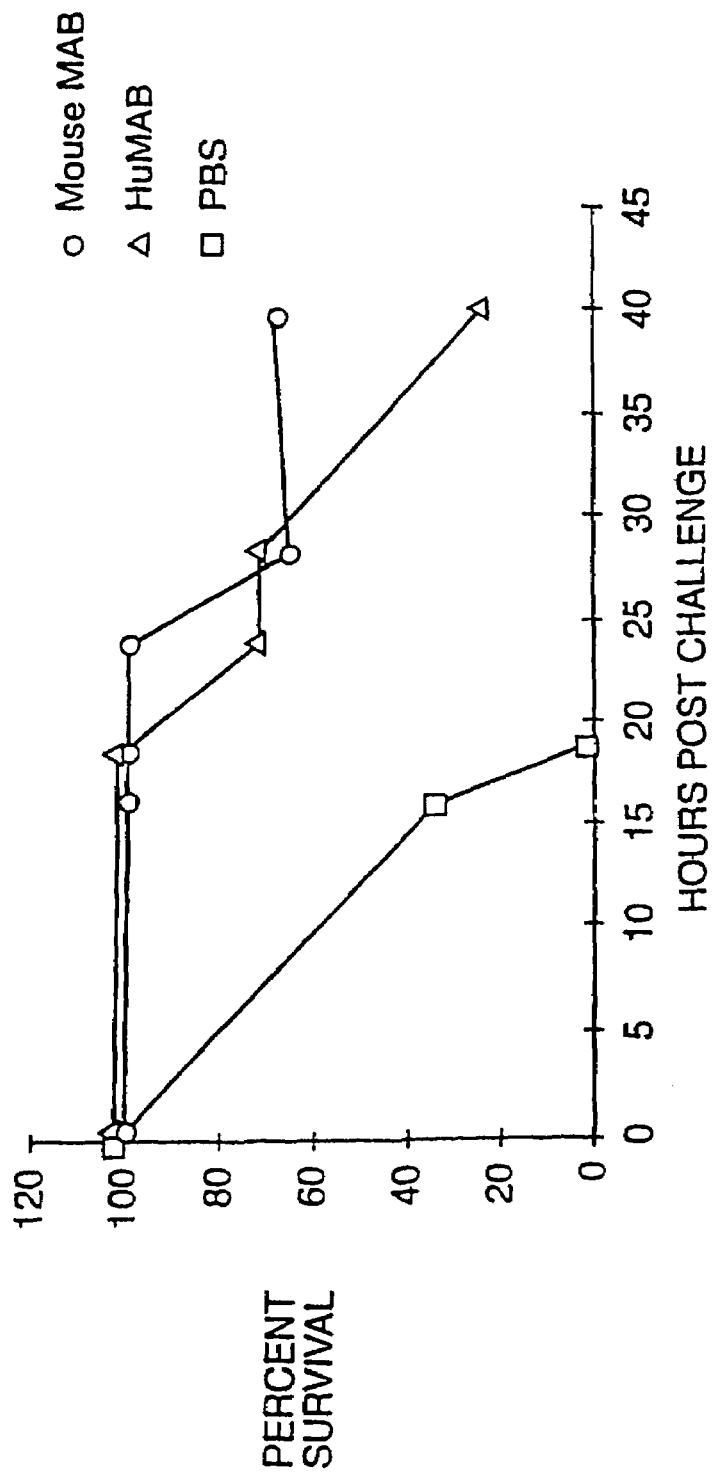

FIG. 18 demonstrates the enhancement of survival after administration of MAB 96-110 in a lethal model of *S. epidermidis* sepsis.

Figure 19:
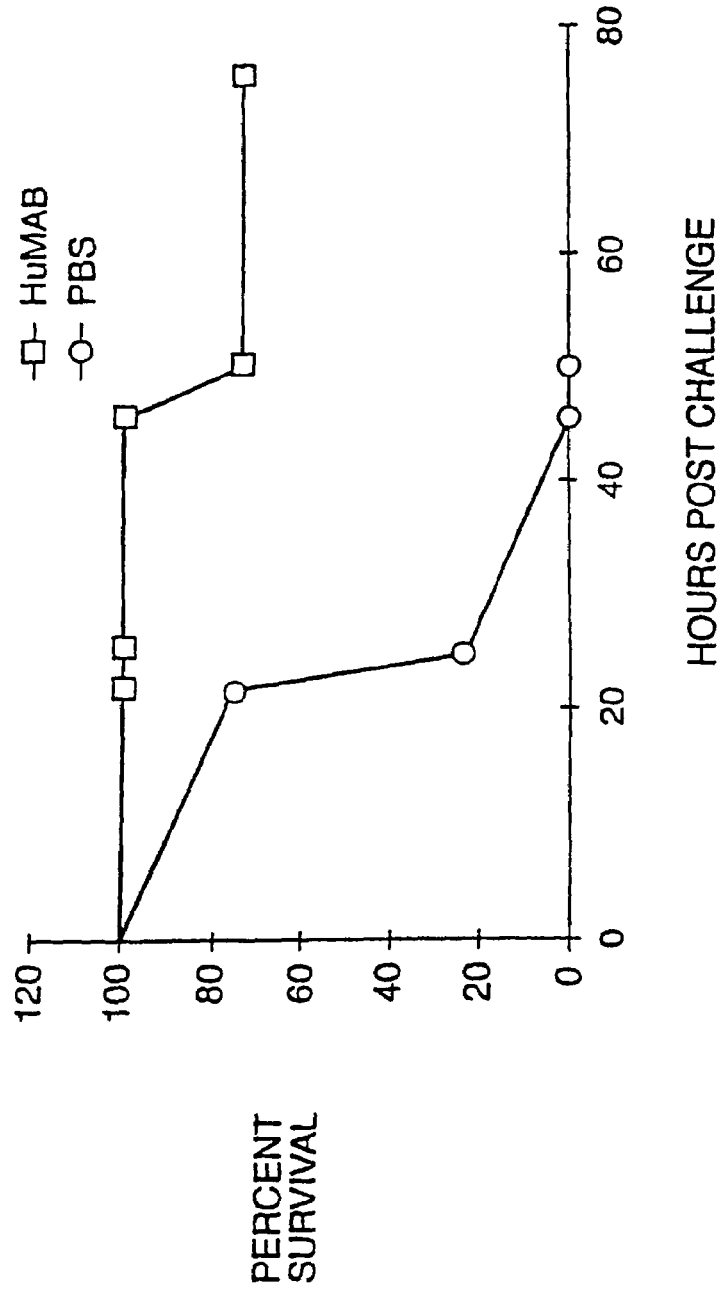

FIG. 19 depicts the effect of the chimeric monoclonal antibody 96-110 on the survival of adult mice after intraperitoneal challenge with *S. epidermidis*.

Figure 20:
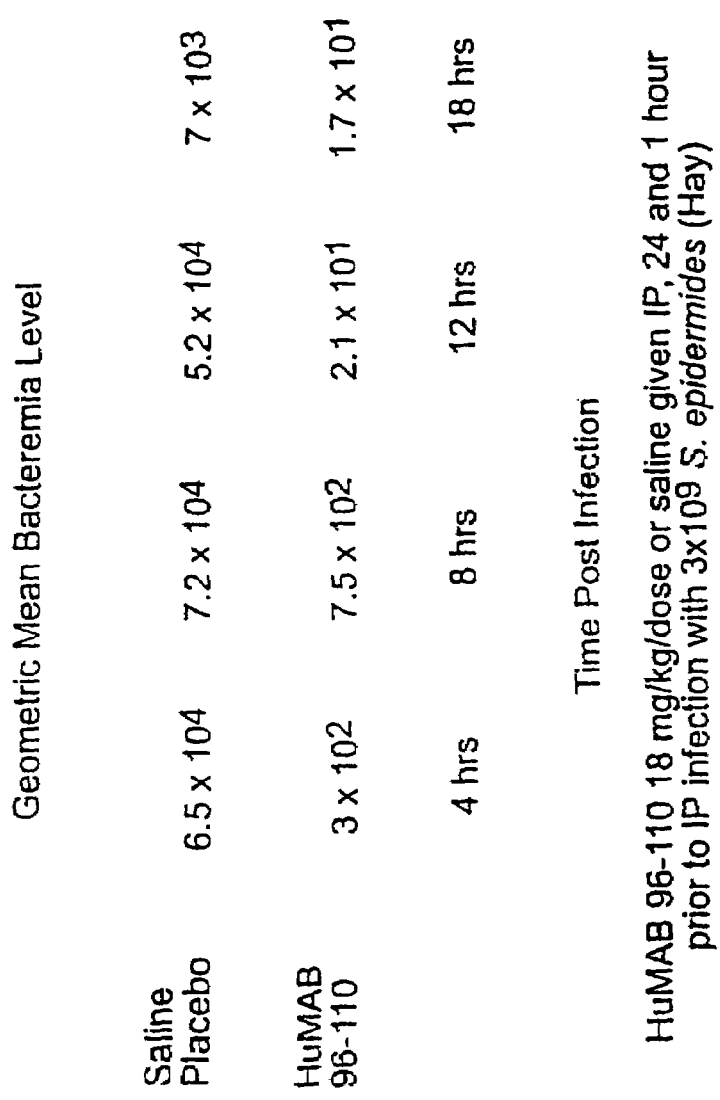

FIG. 20 sets forth the effect of the chimeric monoclonal antibody 96-110 on bacteremia in a lethal *S. epidermidis* model.

Figure 21:
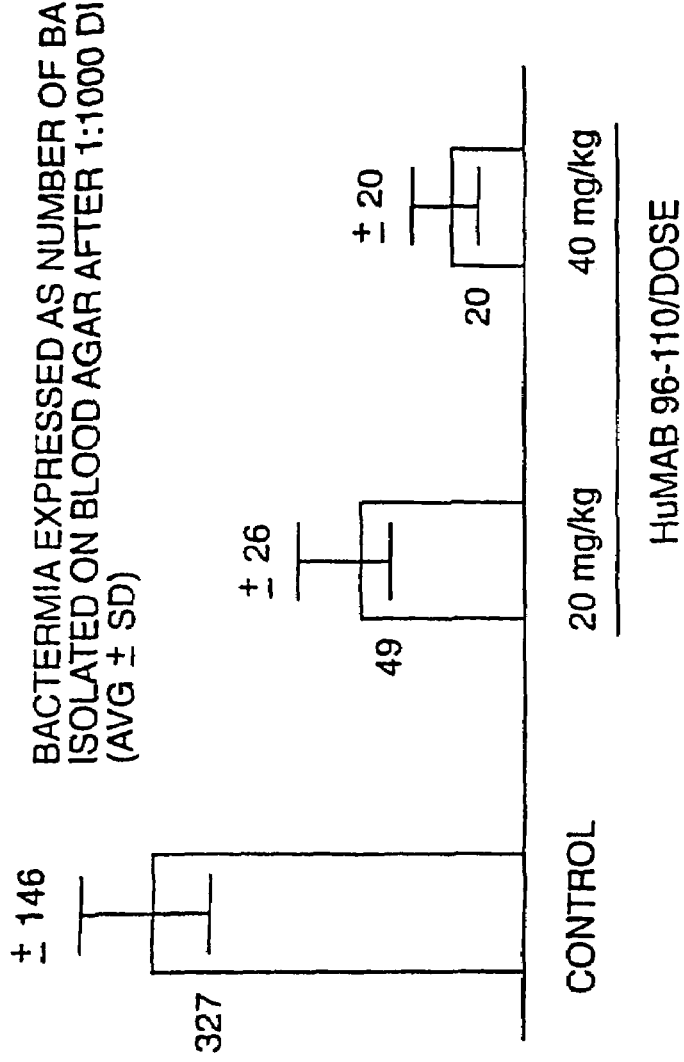

FIG. 21 depicts bacteremia levels four hours after infection with *S. epidermidis* at different doses of the chimeric monoclonal antibody 96-110.

Figure 22:
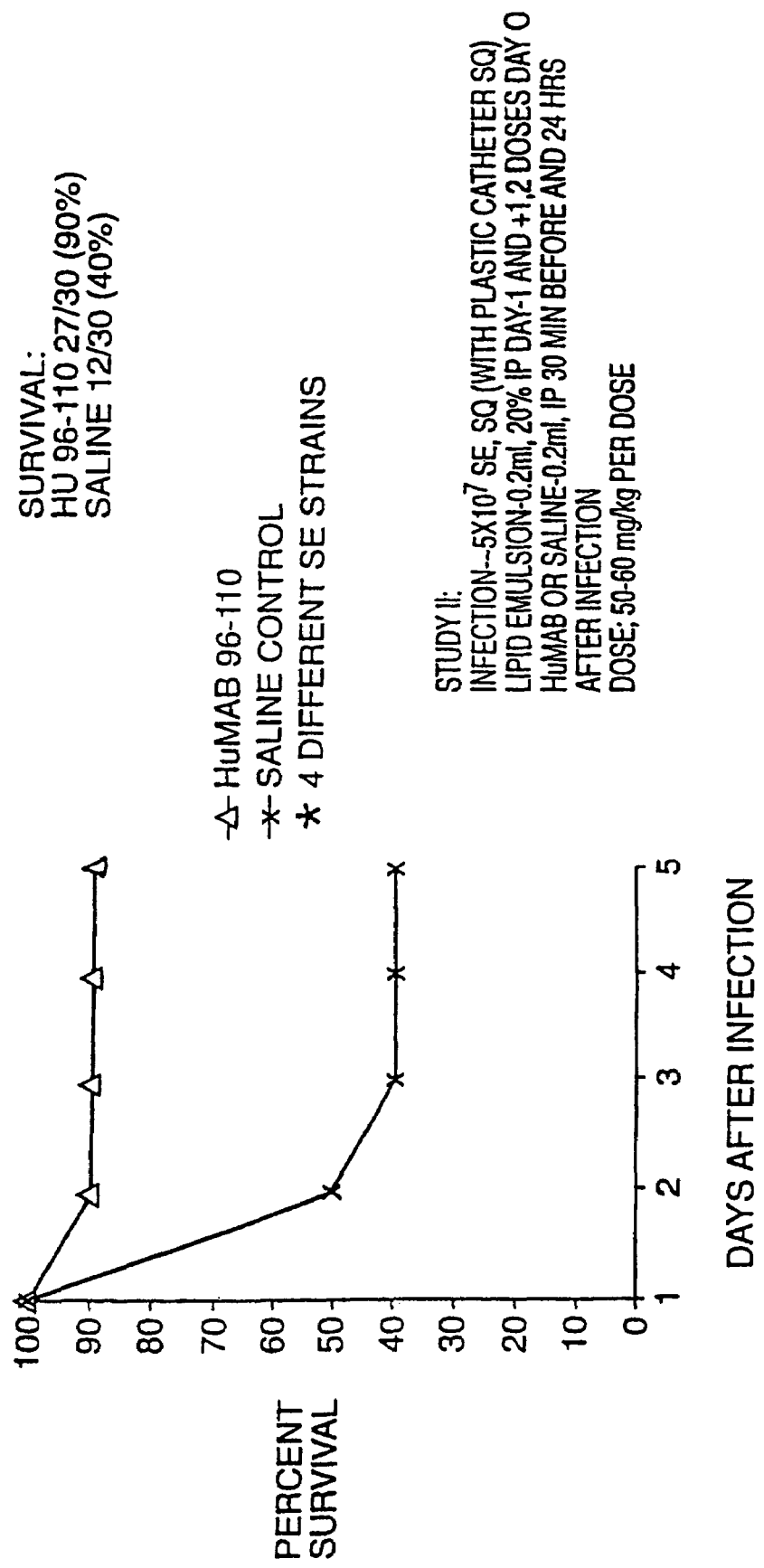

FIG. 22 sets forth the effect of the chimeric monoclonal antibody 96-110 on survival in a lethal neonatal *S. epidermidis* sepsis model.

DETAILED DESCRIPTION OF THE INVENTION

The present invention provides anti-lipoteichoic acid (LTA) murine antibodies (including monoclonal antibodies) and chimeric murine-human antibodies, and fragments, derivatives, and regions thereof, which bind to and opsonize whole Gram positive cocci such as *Staphylococcus* to thereby enhance phagocytosis and killing of such bacteria in vitro and which enhance protection from lethal infection of such bacteria in vivo. The antibodies, fragments, regions, and derivatives thereof of the invention preferably recognize and bind to an epitope of LTA that can block the binding of Gram positive bacteria to epithelial cells, such as human epithelial cells. Accordingly, the invention provides broadly reactive and opsonic antibodies for the diagnosis, prevention, and/or treatment of bacterial infections caused by Gram positive bacteria.

The antibodies of the invention are broadly reactive with Gram positive bacteria, meaning that they selectively recognize and bind to Gram positive bacteria and do not recognize or bind to Gram negative bacteria. Any conventional binding assay can be used to assess this binding, including for example, the enzyme linked immunosorbent assay described below. The basis of the binding is the presence of LTA exposed on the surface of the cell wall of Gram positive bacteria.

Figure 1:
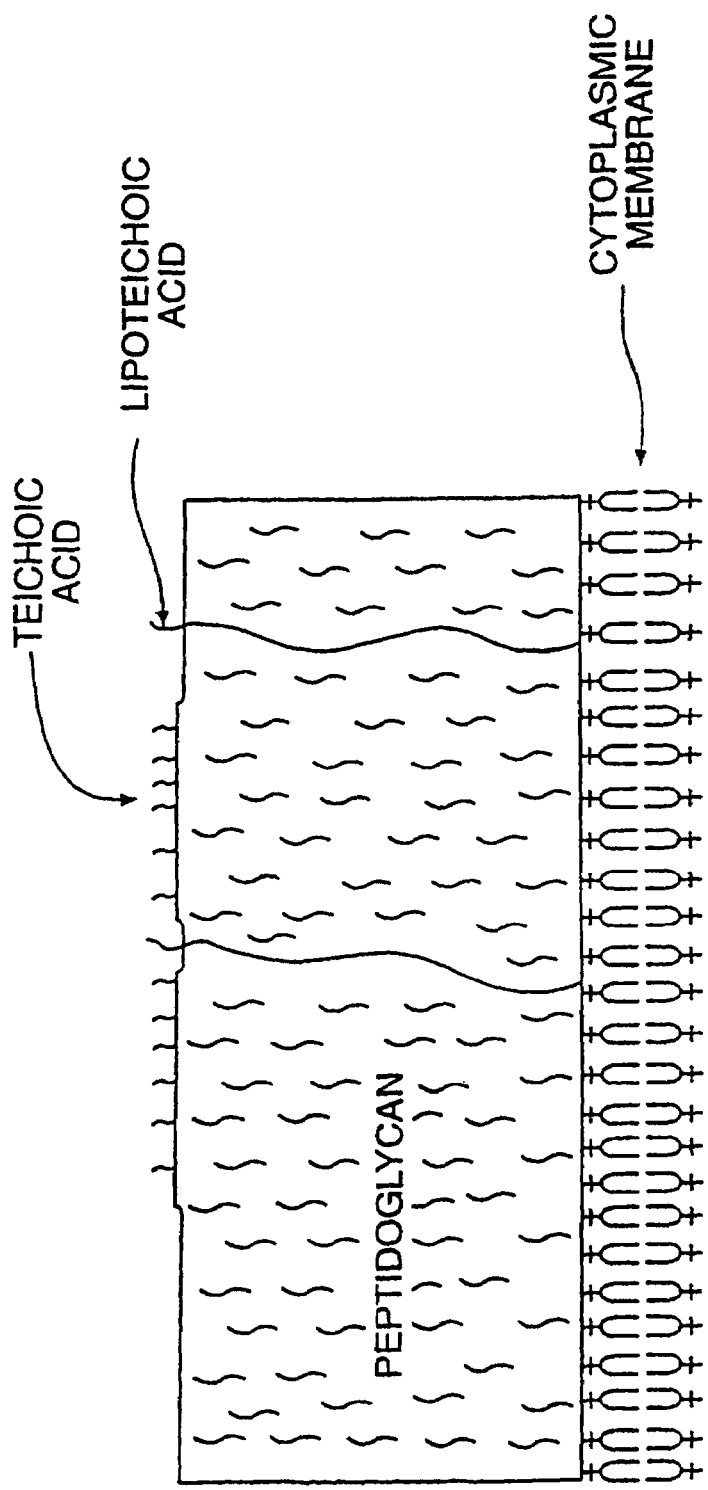
FIG. 1 provides a schematic representation of lipoteichoic acid (LTA) in the Gram positive bacterial cell wall.

As noted above, the cell walls of Gram positive bacteria characteristically contain peptidoglycans such as murein as well as teichoic acids. Teichoic acids are polymers of either glycerol phosphate or ribitol phosphate with various sugars, amino sugars, and amino acids as substituents. Although the lengths of the chains and the nature and location of the substituents vary from species to species and sometimes between species, in general teichoic acids make up a major part of the cell wall. The teichoic acids related to this invention are lipoteichoic acids which are teichoic acids made up of glycerol phosphate which is primarily linked to a glycolipid in the underlying cell membrane. Although the precise structure of LTA in the Gram positive bacterial cell wall is not known, a standard schematic representation commonly accepted in the art is set forth in FIG. 1. Accordingly, the antibodies of the claimed invention are broadly reactive because they recognize and bind to the lipoteichoic acids that are characteristically surface exposed on Gram positive bacteria.

The antibodies of the invention are also opsonic, or exhibit opsonic activity, for Gram positive bacteria. As those in the art recognize, "opsonic activity" refers to the ability of an opsonin (generally either an antibody or the serum factor C3b) to bind to an antigen to promote attachment of the antigen to the phagocyte and thereby enhance phagocytosis. Certain bacteria, especially encapsulated bacteria which resist phagocytosis due to the presence of the capsule, become extremely attractive to phagocytes such as neutrophils and macrophages when coated with an opsonic antibody and their rate of clearance from the bloodstream is strikingly enhanced. Opsonic activity may be measured in any conventional manner as described below.

The ability of the anti-LTA antibodies of the invention to bind to and opsonize Gram positive bacteria and thereby enhance phagocytosis and cell killing in vitro and to enhance protection in vivo is completely unexpected because anti-LTA antibodies have been reported to lack opsonic activity. Indeed, anti-LTA antibodies have been often used as controls.

For example, Fattom et al., J. Clin. Micro. 30(12):3270-3273 (1992) examined the opsonic activity of antibodies induced against type specific capsular polysaccharide of *S. epidermidis*, using as controls antibodies induced against techoic acids and against *S. hominus*. While type-specific antibodies were highly opsonic, anti-techoic acid antibodies were not different from the anti-*S. hominus* antibodies.

Similarly, in Kojima et al., J. Infect. Dis. 162:435-441 (1990), the authors assessed the protective effects of antibody to capsular polysaccharide/adhesion against catheter-related bacteremia due to coagulase negative Staphylococci and specifically used a strain of *S. epidermidis* that expresses teichoic acid as a control. See page 436, Materials and Methods, left column, first ¶; right column, third ¶. In a later study, the authors reached a more explicit conclusion against the utility of anti-techoic antibodies:

> Immunization protocols designed to elicit antibody to techoic acid but not to PS/A afforded no protection against bacteremia or endocarditis.

Takeda, et al., Circulation 86(6):2539-2546 (1991).

Contrary to the prevailing view in the field, the broadly reactive opsonic antibodies against the LTA of Gram positive bacteria, including *S. aureus* and *S. epidermidis*, of the invention satisfy a clear need in the art. As described in the background section, both *S. aureus* and *S. epidermidis* are common causes of post-operative wound infections; *S. epidermidis* has become a major cause of nosocomial infections in patients whose treatments include the placement of foreign objects; *S. epidermidis* has become a common cause of peritonitis in patients with continuous ambulatory peritoneal dialysis; and *S. epidermidis* is now recognized as a common cause of neonatal sepsis.

Indeed, our laboratory has recently focused tremendous efforts to find broadly opsonic antibodies as detailed in a recent series of four related applications and one issued patent, specifically:

U.S. Ser. No. 08/296,133, filed Aug. 26, 1994, of Gerald W. Fischer, entitled "Directed Human Immune Globulin for the Prevention of Staphylococcal Infections," now abandoned;

U.S. Pat. No. 5,571,511, issued Nov. 5, 1996 to Gerald W. Fischer, entitled "Broadly Reactive Opsonic Antibodies that React with Common Staphylococcal Antigens;"

U.S. Ser. No. 08/466,059, filed Jun. 6, 1995, of Gerald W. Fischer, entitled "In Vitro Methods for Identifying Pathogenic Staphylococcus, For Identifying Immunoglobulin Useful for the Treatment of Pathogenic Staphylococcus Infections, and In Vitro Methods Employing such Immunoglobulins," now abandoned;

U.S. Ser. No. 08/308,495, filed Sep. 21, 1994, of Gerald W. Fischer, entitled "Broadly Reactive Opsonic Antibodies that React with Common Staphylococcal Antigens," now abandoned.

all of which are specifically incorporated herein by reference.

This series of applications and the issued patent describe the search for broadly reactive opsonic antibodies particularly against Staphylococci. In rough chronological order, the "Directed Human Immune Globulin" application describes the selection and use of Directed Human Immune Globulin to prevent or treat infections caused by *S. epidermidis* which contains antibodies with the ability to bind to surface antigens of *S. epidermidis* in an ELISA and the exhibition of greater than 80% opsonophagocytic bactericidal activity against *S. epidermidis* in a particularly described in vitro assay. The issued patent claims describes for the first time a particular strain of *S. epidermidis* that identifies broadly reactive opsonic antibodies against both coagulase positive and coagulase negative Staphylococci and specifically claims an antigen preparation isolated from *S. epidermidis* strain Hay ATCC 55133, deposited on Dec. 19, 1990, which generates broadly reactive opsonic antibody which specifically reacts in an assay with *S. epidermidis* serotypes I, II and III, and which exhibits opsonic activity greater than 70%. The "In Vitro Methods" application describes the use of a Serotype II *S. epidermidis*, such as the Hay strain, that identifies pathogenic *Staphylococcus* infections. The fourth application in the chain describes a surface protein identified on the Hay strain that can induce broadly reactive opsonic antibodies.

Nonetheless, the search continued for antibodies, both polyclonal and monoclonal, that are broadly reactive and opsonic against all Gram positive bacteria and has culminated in the present invention. Having discovered the Hay strain and determined its unique ability to generate broadly opsonic antibodies against Staphylococci, it was used as the basis for this search.

As set forth in Example 1, mice were immunized with whole strain Hay *S. epidermidis* from which hybridomas were produced. In screening the hybridomas for antibodies, the antibodies of one clone (first designated 96-105CE11 IF6 and later designated 96-110 MAB) exhibited a strong IgG reaction (Tables 1 and 2) and, in further tests, was found to bind very strongly to Gram positive bacteria such as to strain Hay, to all three serotypes of *S. epidermidis*, to *S. hemolyticus*, *S. hominus*, and two serotypes of *S. aureus* (Tables 3-6) but not to the Gram negative control, *Haemophilus influenza*.

Similar to the antibodies described in the Fischer applications and patent set forth above, the antibody of the present invention exhibits very strong binding, i.e., O.D.s of around twice background in an enzyme-linked immunosorbent assay (described below), against strain Hay. In a preferred embodiment, the level of high binding is equal to or greater than five times background. In other embodiments, the level of high binding is equal to or greater than 10 times background. Of course, any meaningful increase over background (the level observed when all the reagents other than the antibody being tested) will be recognized by skilled persons in the art as high binding and therefor within the scope of the invention.

Also as described in the Fischer applications and patent, high binding has been found to correlate with opsonic activity. As set forth in Example 2, in a neutrophil mediated bactericidal assay (described below), the 96-110 MAB exhibited enhanced opsonization against the prototypic coagulase negative bacteria, *S. epidermidis*, and against the prototypic coagulase positive bacteria, *S. aureus*. With this level of opsonic activity, an antibody should enhance phagocytosis and cell killing of both coagulase negative and coagulase positive bacteria.

The term "enhanced" refers to activity that measurably exceeds background at a valuable level. The level deemed valuable may well vary depending on the specific circumstances of the infection, including the type of bacteria and the severity of the infection. For example, for enhanced opsonic or phagocytic activity, in a preferred embodiment, an enhanced response is equal to or greater than 75% over background. In another preferred embodiment, the enhanced response is equal to or greater than 80% over background. In yet another embodiment, the enhanced response is equal to or greater than 90% over background.

To confirm that the antibody, previously shown to be broadly reactive as well as opsonic, would be protective in vivo, MAB 96-110 was assessed in a lethal infection model in both neonatal rats and adult mice. As set forth in Example 3, survival in control animals given either no therapy, saline, or control MAB, ranged from 0 to less than 10%. However, MAB 96-110 enhanced the survival to 50% or greater.

Where, as here, the enhancement measured is of survival, the preferred increase over background may be more modest than above. Thus, an increase in survival of 25% may be an enhanced response. In other embodiments, enhanced survival may be greater than 50%. Again, the person of skill in the art would recognize other meaningful increases in survival as within the invention.

In view of the impressive opsonic activity in vitro as well as the protective activity in vivo of MAB 96-110, we sought the identity of the epitope of the antigen to which it bound. An "antigen" is a molecule or a portion of a molecule capable of being bound by an antibody and which is also capable of inducing an animal to produce antibody capable of binding to an epitope of that antigen. An antigen may have one or more epitopes. An "epitope" analogously means that portion of the molecule that is capable of being recognized by and bound by an antibody. In general, epitopes consist of chemically active surface groupings of molecules such as amino acids or sugar side chains that have specified three dimensional structural and specific charge characteristics.

In a series of panning experiments set forth in Examples 4-6, we identified peptide sequences to which MAB 96-110 bound strongly. These sequences provide at least peptide mimics of the epitope to which MAB 96-110 bound. Thus, one aspect of the present invention involves a peptide having the sequence

W R M Y F S H R H A H L R S P   (SEQ ID NO 1)

and another aspect of the invention involves a peptide having the sequence

W H W R H R I P L Q L A A G R.   (SEQ ID NO 2).

Of course, the epitope of the invention may be identical to one of these sequences or may be substantially homologous to these sequences such that the anti-LTA antibodies of the invention will bind to them. Alternatively, the substantially homologous sequences of the invention are those that are able to induce the anti-LTA antibodies of the invention. Other peptide epitope mimics within the invention may vary in length and sequence from these two peptides.

The present invention also encompasses recombinant epitopes, epitope mimics, and antigens. The DNA sequence of the gene coding for the isolated antigen can be identified, isolated, cloned, and transferred to a prokaryotic or eukaryotic cell for expression by procedures well-known in the art. For example, procedures are generally described in Sambrook et al., Molecular Cloning, A Laboratory Manual, 2nd Ed., Cold Springs Harbor Press, Cold Spring Harbor, N.Y. (1989) incorporated by reference.

To confirm the specificity of the peptides for the monoclonal antibody, it was tested in a competitive inhibition assay and found to inhibit binding of MAB 96-110 to strain Hay. See Example 6.

To determine the protein of which such sequences are a part, we compared the peptide sequences to the sequences of proteins but, as set forth in Example 7, failed to identify any known protein. Accordingly, we expanded our search of other antigen candidates. Because the peptide sequence was small and had successfully inhibited the binding of MAB 96-110 to strain Hay and because MAB 96-110 bound to and opsonized all three serotypes of *S. epidermidis* as well as to both coagulase negative and coagulase positive bacteria, we assessed the possibility that the peptide was part of a surface exposed lipoteichoic acid. To our surprise, as set forth in Example 7, we found that MAB 96-110 bound to the LTAs of several Gram positive bacteria such as S. mutans, S. aureus, S. faecalis, S. pyogenes (group A Streptococcus).

Thus, the present invention includes antibodies that are capable of binding to the LTA of Gram positive bacteria, including both coagulase negative and coagulase positive bacteria, and of enhancing the opsonization of such bacteria. These anti-LTA antibodies include polyclonal antibodies as well as monoclonal antibodies produced by the hybridomas of the invention, such as MAB 96-110 as well as other monoclonal antibodies, fragments and regions thereof, as well as derivatives thereof. As set forth above, the strength of the binding may range from twice above background, to five- and ten-times above background. In addition, the antibodies, fragments, regions, and derivatives of the present invention are capable of enhancing the opsonization of such bacteria, at rates ranging from 75% and up.

Figure 2:
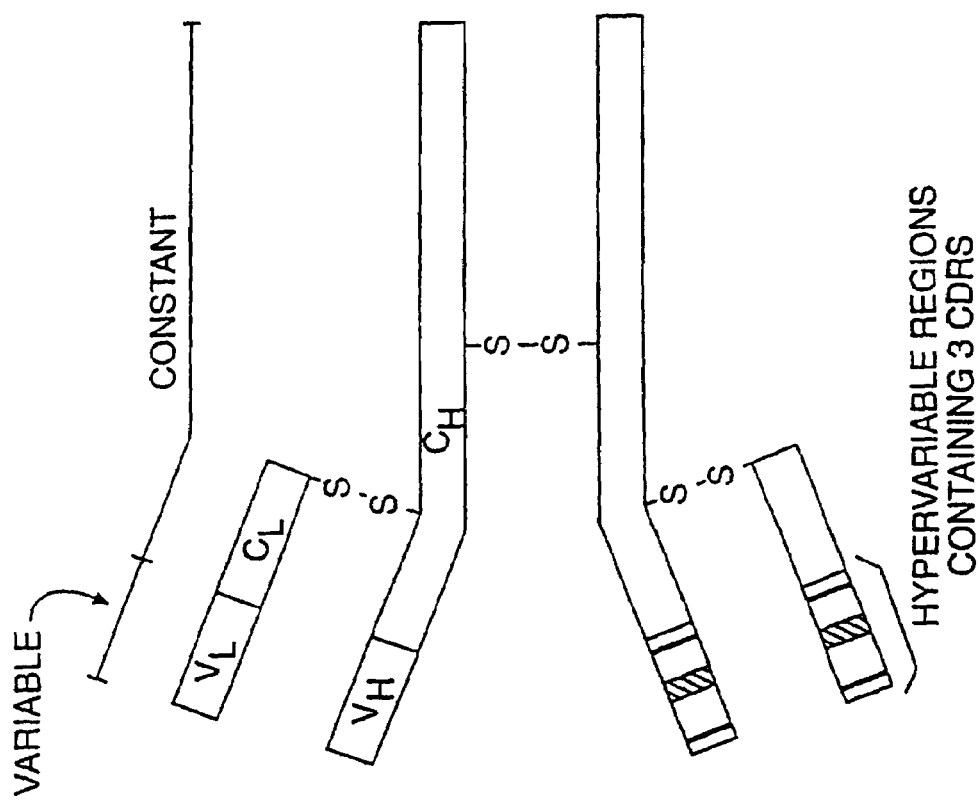
FIG. 2 depicts antibody regions, such as the heavy chain constant region ($C_H$), the heavy chain variable region ($V_H$), the light chain constant region ($C_L$), and the light chain variable region ($V_L$).

The "fragments" of the antibodies of the invention include, for example, Fab, Fab', F(ab')$_2$, and SFv. These fragments are produced from intact antibodies using methods well known in the art such as, for example, proteolytic cleavage with enzymes such as papain (to produce Fab fragments) or pepsin (to produce F(ab')$_2$). The "regions" of the antibodies of the present invention include a heavy chain constant region ($H_c$ or $C_H$), a heavy chain variable region ($H_v$ or $V_H$), a light chain constant region ($L_c$ or $C_L$), and a light chain variable region ($L_v$ or $V_L$) (FIG. 2). The light chains may be either a lambda or a kappa chain.

In a preferred aspect of the invention, the regions include at least one heavy chain variable region or a light chain variable region which binds a portion of LTA, including for example the specific antigen binding sites (that which binds to the epitope) of the two regions. In another embodiment, these two variable regions can be linked together as a single chain antibody. While a full length heavy chain may be critical for opsonic activity and enhance anti-cytokine (anti-inflammatory) activity, the antibody fragments encompassing the variable regions may be suitable for inhibition of bacterial binding to epithelial cells and may also be anti-inflammatory.

In a particularly preferred aspect of the invention, the antibody is a chimeric mouse/human antibody made up of regions from the anti-LTA antibodies of the invention together with regions of human antibodies. For example, a chimeric H chain can comprise the antigen binding region of the heavy chain variable region of the anti-LTA antibody of the invention linked to at least a portion of a human heavy chain constant region. This humanized or chimeric heavy chain may be combined with a chimeric L chain that comprises the antigen binding region of the light chain variable region of the anti-LTA antibody linked to at least a portion of the human light chain constant region.

The chimeric antibodies of the invention may be monovalent, divalent, or polyvalent immunoglobulins. For example, a monovalent chimeric antibody is a dimer (HL) formed by a chimeric H chain associated through disulfide bridges with a chimeric L chain, as noted above. A divalent chimeric antibody is a tetramer ($H_2 L_2$) formed by two HL dimers associated through at least one disulfide bridge. A polyvalent chimeric antibody is based on an aggregation of chains.

A particularly preferred chimeric antibody of the invention is described in Examples 8-10 which set forth in detail the preparation of a preferred chimeric IgG antibody (and in Examples 11-13 which describe the functional activity of this preferred chimeric anibody). Of course, other chimeric antibodies composed of different sections of the anti-LTA antibodies of the invention are within the invention. In particular, the heavy chain constant region can be an IgM or IgA antibody.

In addition to the protein fragments and regions of the antibodies, the present invention also encompasses the DNA sequence of the gene coding for the antibodies as well as the peptides encoded by the DNA. Particularly preferred DNA and peptide sequences are set forth in FIG. 12. That figure provides the variable regions of both the heavy and light chains of MAB 96-110, including the Complementarity Determining Regions ("CDR"), the hypervariable amino acid sequences within antibody variable regions which interact with amino acids on the complementary antigen. The invention includes these DNA and peptide sequences as well as DNA and peptide sequences that are homologous to these sequences. In a preferred embodiment, these sequences are 70% homologous although other preferred embodiments include sequences that are 75%, 80%, 85%, 90%, and 95% homologous. Determining these levels of homology for both the DNA and peptide sequence is well within the routine skill of those in the art.

The DNA sequences of the invention can be identified, isolated, cloned, and transferred to a prokaryotic or eukaryotic cell for expression by procedures well-known in the art. Such procedures are generally described in Sambrook et al., supra, as well as *Current Protocols in Molecular Biology* (Ausubel et al., eds., John Wiley & Sons, 1989), incorporated by reference. In one preferred embodiment, the CDR can be graphed onto any human antibody frame using techniques standard in the art, in such a manner that the CDR maintains the same binding specificity as in the intact antibody.

In addition, the DNA and peptide sequences of the antibodies of the invention, including both monoclonal and chimeric antibodies, may form the basis of antibody "derivatives," which include, for example, the proteins or peptides encoded by truncated or modified genes. Such proteins or peptides may function similarly to the antibodies of the invention. Other modifications, such as the addition of other sequences that may enhance the effector function, which includes phagocytosis and/or killing of the bacteria, are also within the present invention.

The present invention also discloses a pharmaceutical composition comprising the anti-LTA antibodies, whether polyclonal, monoclonal or chimeric, as well as fragments, regions, and derivatives thereof, together with a pharmaceutically acceptable carrier. The pharmaceutical compositions of the invention may alternatively comprise the isolated antigen, epitope, or portions thereof, together with a pharmaceutically acceptable carrier.

Pharmaceutically acceptable carriers can be sterile liquids, such as water, oils, including petroleum oil, animal oil, vegetable oil, peanut oil, soybean oil, mineral oil, sesame oil, and the like. With intravenous administration, water is a preferred carrier. Saline solutions, aqueous dextrose, and glycerol solutions can also be employed as liquid carriers, particularly for injectable solutions. Suitable pharmaceutical carriers are described in *Remington's Pharmaceutical Sciences*, 18th Edition (A. Gennaro, ed., Mack Pub., Easton, Pa., 1990), incorporated by reference.

Finally, the present invention provides methods for treating a patient infected with, or suspected of being infected with, a Gram positive bacteria such as a staphylococcal organism. The method comprises administering a therapeutically effective amount of a pharmaceutical composition comprising the anti-LTA immunoglobulin (whether polyclonal or monoclonal or chimeric, including fragments, regions, and derivatives thereof and a pharmaceutically acceptable carrier. A patient can be a human or other mammal, such as a dog, cat, cow, sheep, pig, or goat. The patient is preferably a human.

A therapeutically effective amount is an amount reasonably believed to provide some measure of relief or assistance in the treatment of the infection. Such therapy as above or as described below may be primary or supplemental to additional treatment, such as antibiotic therapy, for a staphylococcal infection, an infection caused by a different agent, or an unrelated disease. Indeed, combination therapy with other antibodies is expressly contemplated within the invention.

A further embodiment of the present invention is a method of preventing such infections, comprising administering a prophylactically effective amount of a pharmaceutical composition comprising the anti-LTA antibody (whether polyclonal or monoclonal or chimeric, including fragments, regions, and derivatives thereof and a pharmaceutically acceptable carrier.

A prophylactically effective amount is an amount reasonably believed to provide some measure of prevention of infection by Gram positive bacteria. Such therapy as above or as described below may be primary or supplemental to additional treatment, such as antibiotic therapy, for a staphylococcal infection, an infection caused by a different agent, or an unrelated disease. Indeed, combination therapy with other antibodies is expressly contemplated within the invention.

In another embodiment, the peptide which mimics the LTA epitope would be useful to prevent binding of Gram positive bacteria to epithelial cells and thereby inhibit colonization. For example, a pharmaceutical composition containing such a peptide may be administered intranasally to prevent an infection or to minimize a current infection.

Yet another preferred embodiment of the present invention is a vaccine comprising the epitope, epitope mimic, or other part of the LTA antigen and a pharmaceutically acceptable carrier. Upon introduction into a host, the vaccine generates an antibody broadly protective and opsonic against infection by Gram positive bacteria. The vaccine may include the epitope, an epitope mimic, any mixture of epitopes and epitope mimics, the antigen, different antigens, or any combination of epitopes, epitope mimics and antigens.

Vaccinations are particularly beneficial for individuals known to be or suspected of being at risk of infection by Gram positive bacteria. This includes patients receiving body implants, such as valves, patients with indwelling catheters, patients preparing to undergo surgery involving breakage or damage of skin or mucosal tissue, certain health care workers, and patients expected to develop impaired immune systems from some form of therapy, such as chemotherapy or radiation therapy.

Treatment comprises administering the pharmaceutical composition (including antibodies and vaccines) by intravenous, intraperitoneal, intracorporeal injection, intraarticular, intraventricular, intrathecal, intramuscular, subcutaneous, intranasally, intravaginally, orally, or by any other effective method of administration. The composition may also be given locally, such as by injection to the particular area infected, either intramuscularly or subcutaneously. Administration can comprise administering the pharmaceutical composition by swabbing, immersing, soaking, or wiping directly to a patient. The treatment can also be applied to objects to be placed within a patient, such as dwelling catheters, cardiac values, cerebrospinal fluid shunts, joint prostheses, other implants into the body, or any other objects, instruments, or appliances at risk of becoming infected with a Gram positive bacteria, or at risk of introducing such an infection into a patient.

As a particularly valuable corollary of treatment with the compositions of the invention (including all anti-LTA antibodies (whether polyclonal or monoclonal or chimeric, including fragments, regions, and derivatives thereof), all pharmaceutical compositions based on such antibodies, as well as on epitope, epitope mimics, or other part of the LTA antigen and vaccines based on such epitope or antigens) is the reduction in cytokine release that results from the introduction of the LTA of a Gram positive bacteria. As is now recognized in the art, LTA induces cytokines, including for example tumor necrosis factor alpha, Interleukin 6, and interferon gamma. See Takada et al., Infection and Immunity, 63 (1):57-65 (January 1995). Accordingly, the compositions of the invention may enhance protection at three levels: (1) by binding to LTA on the bacteria and thereby blocking the initial binding to epithelial cells and preventing subsequent invasion of the bacteria; (2) by enhancing opsonization of the bacteria and thereby enhancing clearance of the bacteria from tissues and blood; and/or (3) by binding to LTA and partially or fully blocking cytokine release and modulating the inflammatory responses to prevent shock and tissue destruction.

Having generally described the invention, it is clear that the invention overcomes some of the potentially serious problems described in the Background regarding the development of antibiotic resistant Gram positive bacteria. As set forth above, Staphylococci and streptococci (such as *S. faecalis*) have become increasingly resistant and, with the recent spread of vancomycin resistant strains, antibiotic therapy may become totally ineffective.

Particular aspects of the invention are now presented in the form of the following "Materials and Methods" as well as the specific Examples. Of course, these are included only for purposes of illustration and are not intended to be limiting of the present invention.

Materials and Methods

Bacteria

*S. epidermidis*, strain Hay, was deposited at the ATCC on Dec. 19, 1990 under Accession No. 55133.

Hybridoma

Hybridoma 96-110 was deposited at the ATCC on Jun. 13, 1997 under Accession No. HB-12368.

Isotype Determination Assay

Isotype was determined using an isotype kit obtained from Zymed Laboratories. The kit can be ordered under number 90-6550.

Binding Assays

In the binding assay of the invention, immunoglobulin is reacted with a preparation of a Staphylococcal organism. The binding assay is preferably an enzyme-linked immunosorbent assay (ELISA) or a radioimmunoassay (RIA), but may also be an agglutination assay, a coagglutination assay, a calorimetric assay, a fluorescent binding assay, or any other suitable binding assay that is known in the art. The assay can be performed by competitive or noncompetitive procedures with results determined directly or indirectly.

The *Staphylococcus* preparation may be fixed to a suitable solid support, such as a glass or plastic plate, well, bead, micro-bead, paddle, propeller, or stick. The solid support is preferably a titration plate. The fixed preparation is incubated with immunoglobulin, which is isolated or in a biological fluid such as ascites, and the amount of binding determined. A positive reaction occurs when the amount of binding observed for the test sample is greater than the amount of binding for a negative control. A negative control is any sample known not to contain antigen-specific immunoglobulin. Positive binding may be determined from a simple positive/negative reaction or from the calculation of a series of reactions. This series may include samples containing measured amounts of immunoglobulin that specifically bind to the fixed antigen, creating a standard curve from which the amount of antigen-specific immunoglobulin in an unknown sample can be determined. Alternatively, antibody can be fixed to a solid support and immunoglobulin identified by its ability to bind a bacterial preparation bound to the fixed antibodies.

The specific of the assays used in the Examples are set forth below:

Immunoassay on Methanol-Fixed Bacterial: Heat-killed bacteria were suspended in normal saline at an $OD_{650}$=0.600. Bacteria in 5 mls of the suspension were pelleted by centrifugation (approximately 1800×g, 15 minutes, 10-15° C.). The supernatant was discarded and the pellet resuspended into 12 mls of methanol (MeOH). One hundred microliters of the suspension in MeOH was distributed into each well of Nunc Maxisorp Stripwells. The MeOH was allowed to evaporate, fixing the bacteria to the plastic. The bacteria-coated stripwells were stored in plastic bags and used within 2 months of preparation.

For evaluation of antibodies, the bacteria-coated plates were washed once with PBS and non-specific reactive sites on the bacteria were blocked by the addition of 120 ul/well of a solution of 1% bovine serum albumin (BSA) in PBS. After a 30-60 minute incubation, the wells were washed four times with PBS containing 0.05% Tween-20 (PBS-T). Antibody, diluted in PBS-T, was then added to the wells. Supernatants were tested at a dilution of 1:2. Ascites and purified antibody were tested at dilutions indicated in the Tables. After addition of the antibody, the wells were incubated at room temperature for 30-60 minutes in a draft-free environment. The wells were again washed four times with PBS-T and each well received 95 ul of detection antibody: rabbit anti-mouse IgG, conjugated to horse radish peroxidase (HRP) and diluted 1:4000 in PBS-T. The detection antibodies were specific for mouse gamma, mu or alpha heavy chains (Zymed catalog numbers 61-6020, 61-6820 or 61-6720 respectively), as indicated in the Tables.

Following another 30-60 incubation at room temperature, the wells were washed four times with PBS-T and each well received 100 ul of one-component TMB substrate solution (Kirkegaard and Perry Labs catalog number 50-76-05). The wells were incubated in the dark at room temperature for 15 minutes. The reaction was stopped by the addition of 80 ul of TMB stop solution (Kirkegaard and Perry Labs catalog number 50-85-05) and the absorbance of each well at 450 nm was determined using a Molecular Devices Vmax plate reader.

Immunoassay on LTA's: Reactivity of MAB 96-110 was measured by immunoassay on wells coated with LTA's. LTA's were obtained from Sigma Chemical Company and diluted in PBS to 1 ug/ml. One hundred microliters of the 1 ug/ml solution was distributed into replicate Nunc Maxisorp Stripwells. The LTA was incubated in the wells overnight at room temperature. The unbound material was removed from the wells with four washes of PBS-T. The wells were not blocked with BSA or other proteins. Antibody, diluted in PBS-T, was then added to the wells and the assay continued as described above.

Competitive Inhibition of Antibody of LTA: In order to determine the ability of LTA to inhibit binding of MAB 96-110 to wells coated with MeOH-fixed Strain Hay, a competitive inhibition assay was performed. Wells were coated in MeOH with Strain Hay and blocked with BSA as described above. Fifty ul of LTA from *S. mutans, S. aureus* or *S. facecalis* were added to duplicate wells. Six different concentrations of each LTA were tested (from 0.04 to 9.0 ug/ml). LTA's were diluted in PBS-T to obtain the desired concentrations. Immediately after addition of the LTA, 50 ul of purified MAB 96-110 at 1 ug/ml was added to each well. The final dilution of the MAB 96-110 was therefore 0.5 ug/ml. Uninhibited control wells received only PBS-T and MAB without LTA.

Binding of MAB 96-110 to the LTA in the PBS-T solution resulted in a complex of MAB/LTA which was removed from the plate during the subsequent washing step. The interaction of the MAB 96-110 with the LTA inhibited the antibody from binding to the LTA on the surface of the bacteria and thus reduced the number of MAB 96-110 molecules bound to the MeOH-fixed strain Hay used to coat the wells. Because the number of MAB 96-110 molecules bound to the MeOH-fixed Strain Hay was reduced, the level of binding of the detection antibody (rabbit anti-mouse IgG-HPR) was therefore also decreased, leading to a reduction of color development when compared to wells in which no LTA was present.

Immunoassay with Protein A Method: In order to evaluate monoclonal antibody 96-110 for reactivity with *S. aureus* 5 and *S. aureus* 8, it was necessary to modify the immunoassay procedure described above. Both *S. aureus* strains express Protein A on their surfaces. Because Protein A binds strongly to the constant region of the heavy chains of gamma-globulins, it was possible that false positive results would be obtained due to non-specific binding of the 96-110 antibody to the Protein A molecule. In order to overcome this difficulty, the immunoassay wells were coated with bacteria as described above. However, prior to the addition of the 96-110 antibody to the bacteria-coated wells, the purified monoclonal antibody (MAb) was reacted with a solution of recombinant Protein A conjugated to HRP and diluted 1:500 in PBS-T. This reaction was allowed to proceed for 30 minutes. The wells were washed four times with PBS-T and 100 ul of the solution of Protein A-HRP-MAb was added to the wells. The presence of the Protein A-HRP from the pretreatment prevented the MAb from binding to the Protein A on the *S. aureus* 5 and 8. Furthermore, the binding of the Protein A-HRP to the constant region of the heavy chain did not interfere with the antibody binding site on the MAb, thereby allowing evaluation of the MAb on *S. aureus* and other bacteria.

The Protein A-HRP-MAb was allowed to react in the coated wells for 30-60 minutes at room temperature. The wells were then washed with PBS-T and TMB substrate solution was added and the assay completed as described above.

Opsonization Assays

An opsonization assay can be a calorimetric assay, a chemiluminescent assay, a fluorescent or radiolabel uptake assay, a cell-mediated bactericidal assay, or any other appropriate assay known in the art which measures the opsonic potential of a substance and identifies broadly reactive immunoglobulin. In an opsonization assay, the following are incubated together: an infectious agent, a eukaryotic cell, and the opsonizing substance to be tested, or an opsonizing substance plus a purported opsonizing enhancing substance. Preferably, the opsonization assay is a cell-mediated bactericidal assay. In this in vitro assay, the following are incubated together: an infectious agent, typically a bacterium, a phagocytic cell, and an opsonizing substance, such as immunoglobulin. Although any eukaryotic cell with phagocytic or binding ability may be used in a cell-mediated bactericidal assay, a macrophage, a monocyte, a neutrophil, or any combination of these cells, is preferred. Complement proteins may be included to promote opsonization by both the classical and alternate pathways.

The opsonic ability of immunoglobulin is determined from the amount or number of infectious agents remaining after incubation. In a cell-mediated bactericidal assay, this is accomplished by comparing the number of surviving bacteria between two similar assays, only one of which contains the purported opsonizing immunoglobulin. Alternatively, the opsonic ability is determined by measuring the numbers of viable organisms before and after incubation. A reduced number of bacteria after incubation in the presence of immunoglobulin indicates a positive opsonizing ability. In the cell-mediated bactericidal assay, positive opsonization is determined by culturing the incubation mixture under appropriate bacterial growth conditions. Any significant reduction in the number of viable bacteria comparing pre- and post-incubation samples, or between samples which contain immunoglobulin and those that do not, is a positive reaction.

Clearance/Protective Assays

Another preferred method of identifying agents for the treatment or prevention of a infection by Gram positive bacteria employs lethal models of sepsis that measure clearance and protection. Such agents can be immunoglobulin or other antimicrobial substances.

A particularly useful animal model comprises administering an antibody and a Gram positive organism to an immunocompromised (e.g., an immature) animal, followed by evaluating whether the antibody reduces mortality of the animal or enhances clearance of the organism from the animal. This assay may use any immature animal, including the rabbit, the guinea pig, the mouse, the rat, or any other suitable laboratory animal. The suckling rat lethal animal model is most preferred. Such a model can readily incorporate an infected foreign body, such as an infected catheter, to more closely mimic the clinical setting. An alternative model utilizes adult susceptible animals, such as CF1 mice.

Clearance is evaluated by determining whether the pharmaceutical composition enhances clearance of the infectious agent from the animal. This is typically determined from a sample of biological fluid, such as blood, peritoneal fluid, or cerebrospinal fluid. The infectious agent is cultured from the biological fluid in a manner suitable for growth or identification of the surviving infectious agent. From samples of fluid taken over a period of time after treatment, one skilled in the art can determine the effect of the pharmaceutical composition on the ability of the animal to clear the infectious agent. Further data may be obtained by measuring over a period of time, preferably a period of days, survival of animals to which the pharmaceutical composition is administered. Typically, both sets of data are utilized. Results are considered positive if the pharmaceutical composition enhances clearance or decreases mortality. In situations in which there is enhanced organism clearance, but the test animals still perish, a positive result is still indicated.

EXAMPLE 1

The Production of Hybridomas and Monoclonal Antibodies

To produce monoclonal antibodies that were directed against the surface proteins of *S. epidermidis* and were opsonic and protective for *S. epidermidis*, mice were immunized with whole *S. epidermidis*, Strain Hay.

A suspension of heat killed *S. epidermidis* was adjusted to an optical density (OD) of 0.137 at a wavelength of 650 nm when measured through a 1 centimeter light path. Bacteria from five mls of the suspension were pelleted by centrifugation (approximately 1800×g, 10 minutes, room temperature). The supernatant was discarded and the pellet resuspended in 0.6 mls of PBS, which was then mixed with 0.9 mls of complete Freund's adjuvant (CFA). The resulting emulsion was used as the immunogen.

Adult, female BALB/c mice, obtained from Harlan Sprague Dawley (Indianapolis, Ind.) were immunized subcutaneously with 0.2 mls of the immunogen described above. The mice received a booster immunization approximately two and ½ months later with antigen prepared as described above, except that incomplete Freund's adjuvant (IFA) was used as the adjuvant instead of CFA. A final, prefusion boost was given approximately two months after that. This boost consisted of 1 ml of *S. epidermidis* suspension ($OD_{650}$=0.137). Mice 8159 and 8160 each received an intraperitoneal injection of 0.5 mls of the suspension. Five days later, the spleen from mouse 8159 was removed and used for hybridoma formation.

Hybridomas were prepared by the general methods of Shulman, Wilde and Kohler Nature 276:269-270 (1978) and Bartal and Hirshaut "Current Methods in Hybridoma Formation in *Methods of Hybridoma Formation*, Bartal and Heishaut, eds., Humana Press, Clifton, N.J. (1987). A total of $2.135 \times 10^8$ spleenocytes from mouse 8159 were mixed with $2.35 \times 10^7$ SP2/0 mouse myeloma cells (ATCC Catalog number CRL1581) and pelleted by centrifugation (400×g, 10 minutes at room temperature) and washed in serum free medium. The supernatant was removed to near-dryness and fusion of the cell mixture was accomplished in a sterile 50 ml centrifuge conical by the addition of 1 ml of polyethylene glycol (PEG; mw 1400; Boehringer Mannheim) over a period of 60-90 seconds. The PEG was diluted by slow addition of serum-free medium in successive volumes of 1, 2, 4, 8, 16 and 19 mls. The hybridoma cell suspension was gently resuspended into the medium and the cells pelleted by centrifugation (500×g, 10 minutes at room temperature). The supernatant was removed and the cells resuspended in medium RPMI 1640, supplemented with 10% heat-inactivated fetal bovine serum, 0.05 mM hypoxanthine and 16 uM thymidine (HT medium). One hundred ul of the hybridoma cells were planted into 760 wells of 96-well tissue culture plates. Eight wells (column 1 of plate A) received approximately $2.5 \times 10^4$ SP2/0 cells in 100 ul. The SP2/0 cells served as a control for killing by the selection medium added 24 hours later.

Twenty four hours after preparation of the hybridomas, 100 ul of RPMI 1640, supplemented with 10% heat-inactivated fetal bovine serums, 0.1 mM hypoxanthine, 0.8 uM aminopterin and 32 uM thymidine (HAT medium) was added to each well.

Ninety six hours after the preparation of the hybridomas, the SP2/0 cells in plate A, column 1 appeared to be dead, indicating that the HAT selection medium had successfully killed the unfused SP2/0 cells.

Eleven days after the preparation of the hybridomas, supernatants from all wells were tested by ELISA for the presence of antibodies reactive with methanol-fixed S. epidermidis. Based on the results of this preliminary assay, cells from 20 wells were transferred to a 24-well culture dish. Four days later, supernatant from these cultures were retested by ELISA for the presence of antibodies reactive with methanol-fixed S. epidermidis. Of these supernatants, one (from colony 96-105CE11) was a strongly reactive IgG (Table 1). Two colonies (96-105FD4 and 96-105 GB5) were very weakly reactive IgG's and one colony 96-105HB10 was a weakly reactive IgM. Antibodies of the IgM isotype are not as desirable as IgG's and culture 96-105HB10 was cryopreserved and not further examined.

Cultures 96-105 CE11, FD4 and GB5 were reanalyzed several days later and only CE11 showed a strong response (Table 2). No response was obtained with the other cell cultures, and no further experimental work was done with them.

To further test the specificity of this antibody for S. epidermidis, a whole cell ELISA with several bacteria was performed (Table 3). The antibodies from this colony bound strongly to S. epidermidis (Hay) O.D. 1.090 and to a lesser degree to Group B streptococcus (GBS), but not to H. influenzae (HIB+, with type b capsule; HIB− without typable capsule) or type 14, pneumococcus (Pn 14).

A clone from 96-105CE11 IF6 was isolated and retested and was an IgG-1 that reacted strongly with S. epidermidis (Strain Hay) in the whole cell ELISA (Table 4). This clone was then designated 96-110. To determine if 96-110 had the broad binding characteristics we sought and would be consistent with binding to the surface protein on S. epidermidis (Strain Hay) that bound broadly opsonic antibody, we ran a whole cell ELISA against several coagulase negative staphylococci (Table 5). Using 96-110 in Ascites fluid, strong binding at several dilutions was detected for S. epidermidis type 1, 11, 111, S. hemolyticus and S. hominus.

In addition, 96-110 MAB was purified over a protein G column (Pharmacia). Using a modification of the whole cell ELISA, peroxidase labeled protein A was mixed with the purified 96-110 MAB and then reacted with S. aureus type 5 (SA5) and S. aureus type 8 (SA8) obtained from ATCC at Accession Nos. 12602 and 12605, respectively. Both S. aureus serotypes reacted strongly with the 96-110 MAB (Table 6). Since, in our previous studies, we found that absorption with S. epidermidis (Strain Hay) could decrease IgG opsonic activity and opsonic antibodies raised against Hay reacted with a surface protein of Hay, we felt that this was still consistent with a MAB to the surface protein we were trying to characterize. This finding was also important since types 5 & 8, S. aureus are serotypes commonly associated with human infections. Using this protein A assay, MAB to type 14 pneumococcus did not demonstrate binding to S. aureus.

Therefore, we have identified a mouse $IgG_1$ MAB raised against S. epidermidis (Strain Hay) that binds to the surface of both coagulase negative and coagulase positive Staphylococci of Gram positive bacteria. Such an antibody would be valuable to prevent or treat infections of Gram positive cocci by preventing attachment of bacteria to epithelial cells or foreign bodies, by enhancing opsonization and protection from infection and by reducing (down modulating) the inflammatory response.

TABLE 1

Immunoassay Results, 96-105 Supernatants on Methanol-Fixed S. Hay

| Colony | Detection Specific For: | | |
|---|---|---|---|
| ID | G | A | M |
| PBS-F | 0.070 | 0.080 | 0.050 |
| CE11 | 0.788 | 0.065 | 0.056 |
| EB5 | 0.079 | 0.065 | 0.053 |
| EE5 | 0.084 | 0.069 | 0.055 |
| FD4 | 0.089 | 0.067 | 0.059 |
| FG4 | 0.087 | 0.065 | 0.065 |
| FG8 | 0.090 | 0.060 | 0.062 |
| FF9 | 0.095 | 0.062 | 0.059 |
| GE4 | 0.074 | 0.067 | 0.059 |
| GB5 | 0.155 | 0.077 | 0.078 |
| GB6 | 0.073 | 0.062 | 0.053 |
| GC6 | 0.069 | 0.062 | 0.052 |
| GC9 | 0.076 | 0.062 | 0.053 |
| GB10 | 0.075 | 0.064 | 0.102 |
| HG2 | 0.195 | 0.067 | 0.059 |
| HG3 | 0.079 | 0.066 | 0.060 |
| HE4 | 0.076 | 0.073 | 0.065 |
| HG4 | 0.077 | 0.101 | 0.061 |
| HG5 | 0.077 | 0.062 | 0.058 |
| HC8 | 0.083 | 0.064 | 0.057 |
| HB10 | 0.070 | 0.064 | 0.223 |
| AC4 IID10* | 0.065 | 0.066 | 0.069 |

*Monoclonal antibody reactive with Hib protein D.

TABLE 2

Immunoassay Results, 96-105 Supernatants on Methanol-Fixed S. Hay

| Colony | Detection Specific For: | | |
|---|---|---|---|
| ID | G | A | M |
| Buffer | 0.052 | 0.045 | 0.045 |
| CE11 | 0.933 | 0.049 | 0.046 |
| FD4 | 0.073 | 0.054 | 0.051 |
| GB5 | 0.050 | 0.040 | 0.036 |

TABLE 3

Immunoassay Results, 96-105 Supernatants on Methanol-Fixed Bacteria

| Colony ID | Detection Antibody | Hay | Hib+ | Hib− | GBS | Pn14 |
|---|---|---|---|---|---|---|
| CE11 | gamma-specific | 1.090 | 0.106 | 0.068 | 0.304 | 0.063 |
| FE11 | gamma-specific | 0.167 | 0.084 | 0.068 | 0.112 | 0.053 |
| Buffer | gamma-specific | 0.048 | 0.075 | 0.056 | 0.070 | 0.053 |

Several colonies from 96-105 not cloned.

TABLE 4

Assay of 96-105 CE11 IF6 on Various Bacteria

| Antibody | Antigen | Dilution | Isotype | Hay | Pn14 |
|---|---|---|---|---|---|
| PBS-T | | | | 0.072 | 0.064 |
| 96-105CE11-IF6 | Hay | 2 | IgG-1, k | 1.608 | 0.099 |
| | | 4 | | 1.184 | 0.087 |
| | | 8 | | 0.846 | 0.069 |
| | | 16 | | 0.466 | 0.074 |

TABLE 5

Detection of Bacteria of Anti-Hay Monoclonal* in Whole Cell ELISA

| Antibody | Dilution | Staph. Hay | Staph. Epi I | Staph. Epi II | Staph. Epi III | Staph. Hemmolyt. | Staph. Hominus |
|---|---|---|---|---|---|---|---|
| Buffer | | 0.056 | 0.063 | 0.066 | 0.055 | 0.058 | 0.074 |
| 96-110 Ascites | 100 | 1.448 | 2.334 | 1.524 | 1.241 | 1.197 | 0.868 |
| | 400 | 1.325 | 2.542 | 0.746 | 0.425 | 0.830 | 0.422 |
| | 1600 | 1.087 | 2.452 | 0.369 | 0.176 | 0.680 | 0.185 |
| | 6400 | 0.930 | 2.430 | 0.195 | 0.089 | 0.602 | 0.110 |
| | 25600 | 0.674 | 1.672 | 0.113 | 0.069 | 0.647 | 0.081 |

*Anti-Hay Monoclonal from unpurified ascites fluid

TABLE 6

Detection of Methanol-Fixed SA5, SA8 and S. Hay
By Purified Monoclonal Anti-Hay Using Protein A

| Anti-Hay Dilution | ATCC SA5 | ATCC SA8 | USU Hay |
|---|---|---|---|
| 500 | 1.329 | 3.345 | 3.017 |
| 1000 | 1.275 | 2.141 | 2.266 |
| 2000 | 0.873 | 1.016 | 1.487 |
| 4000 | 0.333 | 0.491 | 0.951 |
| 8000 | 0.159 | 0.232 | 0.490 |
| 16000 | 0.132 | 0.149 | 0.331 |
| Normal Mouse 1000 | 0.101 | 0.090 | 0.082 |
| Buffer | 0.102 | 0.113 | 0.152 |

Purified anti-Hay stock = 1.63 mg/ml

EXAMPLE 2

The Opsonic Activity of the Monoclonal Antibody

Antibodies which bind to an antigen may not necessarily enhance opsonization or enhance protection from infection. Therefore, a neutrophil mediated bactericidal assay was used to determine the functional activity of antibody to *S. epidermidis*. Neutrophils were isolated from adult venous blood by dextran sedimentation and ficoll-hypaque density centrifugation. Washed neutrophils were added to round-bottomed wells of microtiter plates (approximately $10^6$ cells per well) with approximately $3 \times 10^4$ mid-log phase bacteria (*S. epidermidis* Hay, ATCC 55133). Newborn lamb serum (10 uls), screened to assure absence of antibody to *S. epidermidis*, was used as a source of active complement.

Forty microliters of immunoglobulin (or serum) were added at various dilutions and the plates were incubated at 37° C. with constant, vigorous shaking. Samples of 10 uls were taken from each well at zero time and after 2 hours of incubation. Each was diluted, vigorously vortexed to disperse the bacteria, and cultured on blood agar plates overnight at 37° C. to quantitate the number of viable bacteria. Results are presented as percent reduction in numbers of bacterial colonies observed compared to control samples.

Since the 96-110 MAB bound to both coagulase negative and coagulase positive Staphylococci, opsonic studies were performed to determine if the MAB enhanced phagocytosis and killing of both groups of staphylococci. At a 1:80 dilution, the MAB enhanced opsonization and killing of coagulase negative *Staphylococcus* (*S. epidermidis*) to 100%, compared with 49.5% with C' and PMN alone (Table 7). The coagulase positive *Staphylococcus* also showed enhanced phagocytosis at 1:10 and 1:40 dilution (83.3% and 78.9% respectively) compared with 53.7 percent with C' and PMN alone. At 1:80 dilution, the opsonic activity against *S. aureus* was decreased to 61%.

These data show that not only does the MAB bind to the surface of both coagulase negative and coagulase positive Staphylococci, but that it has functional activity and can enhance phagocytosis and killing of these bacteria. Such an antibody would be capable of promoting clearance of Staphylococci that have invaded a host and would be useful therapeutic agent.

TABLE 7

Opsonic Assay
Antibody: Purified M X Hay, 96-110

| Group Description | Ab Dilution | % Killed S. epidermidis | % Killed S. aureus |
|---|---|---|---|
| C' only | | 0.0 | 0.0 |
| PMN only | | 0.0 | 0.0 |
| PMN + C' No Ab | | 49.5 | 53.7 |
| PMN + Ab + C' | 10 | — | 83.3 |
| | 40 | — | 78.9 |
| | 80 | 100.0 | 61.0 |

EXAMPLE 3

In vivo Protective Efficacy

Opsonic antibody correlates with enhanced protection from staphylococcal infections, as set forth in the recent series of Fischer applications and issued patent described and incorporated by reference above. To further demonstrate that the MAB can enhance survival to infections with both coagulase positive and coagulase negative Staphylococci, studies were conducted using lethal infection models.

Two day old Wistar rats were injected with ~$10^6$ *S. aureus* (type 5, ATCC 12605) subcutaneously just cephalad to the tail. Approximately 30 minutes before and 24 and 48 hours after infection, 0.2 ml MAB 96-110 (~320 ug) was given IP. Control animals were given an equal volume of saline or a control MAB not directed against Staphylococci. All animals were observed daily for five days to determine survival.

Figure 3:
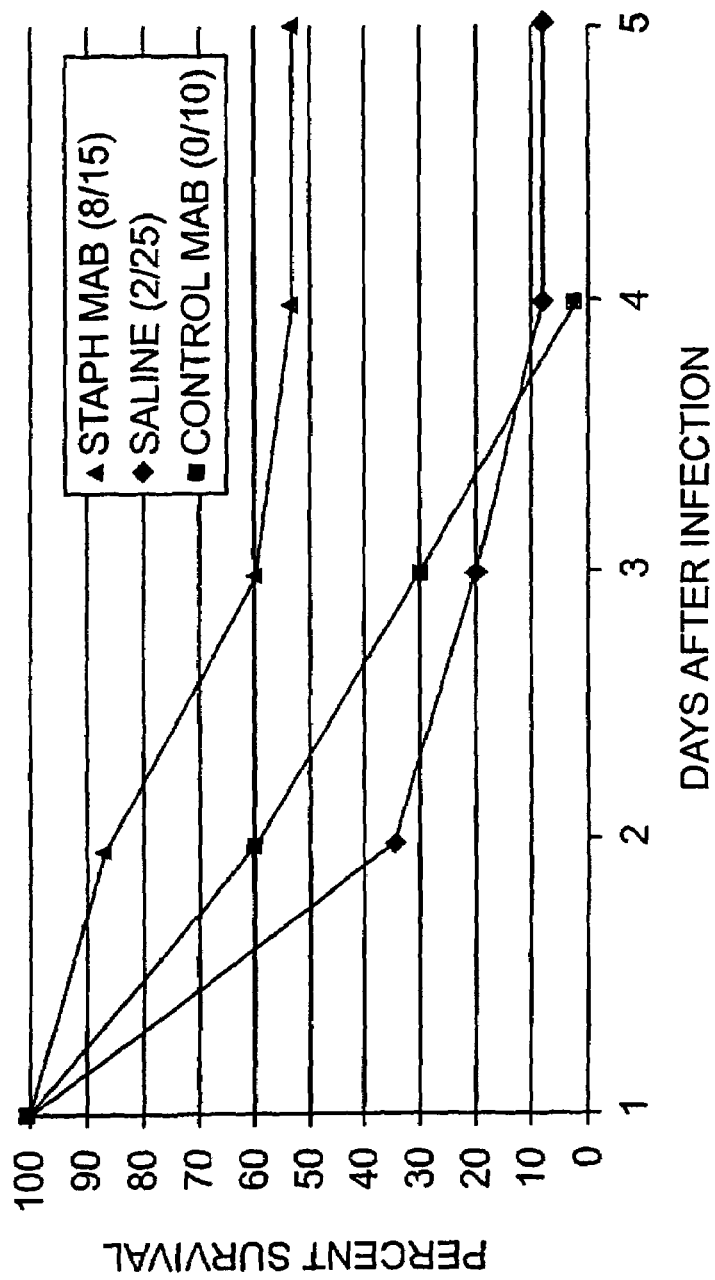
FIG. 3 demonstrates the enhancement of survival after administration of MAB 96-110 in a lethal neonatal model of coagulase positive *staphylococcus* sepsis.

MAB 96-110 enhanced survival in this lethal neonatal model of coagulase positive *staphylococcus* sepsis (FIG. 3): 8/15 survived after treatment with MAB 96-110, and 0/10 survived with Control MAB or 2/25 with saline treatment.

Figure 4:
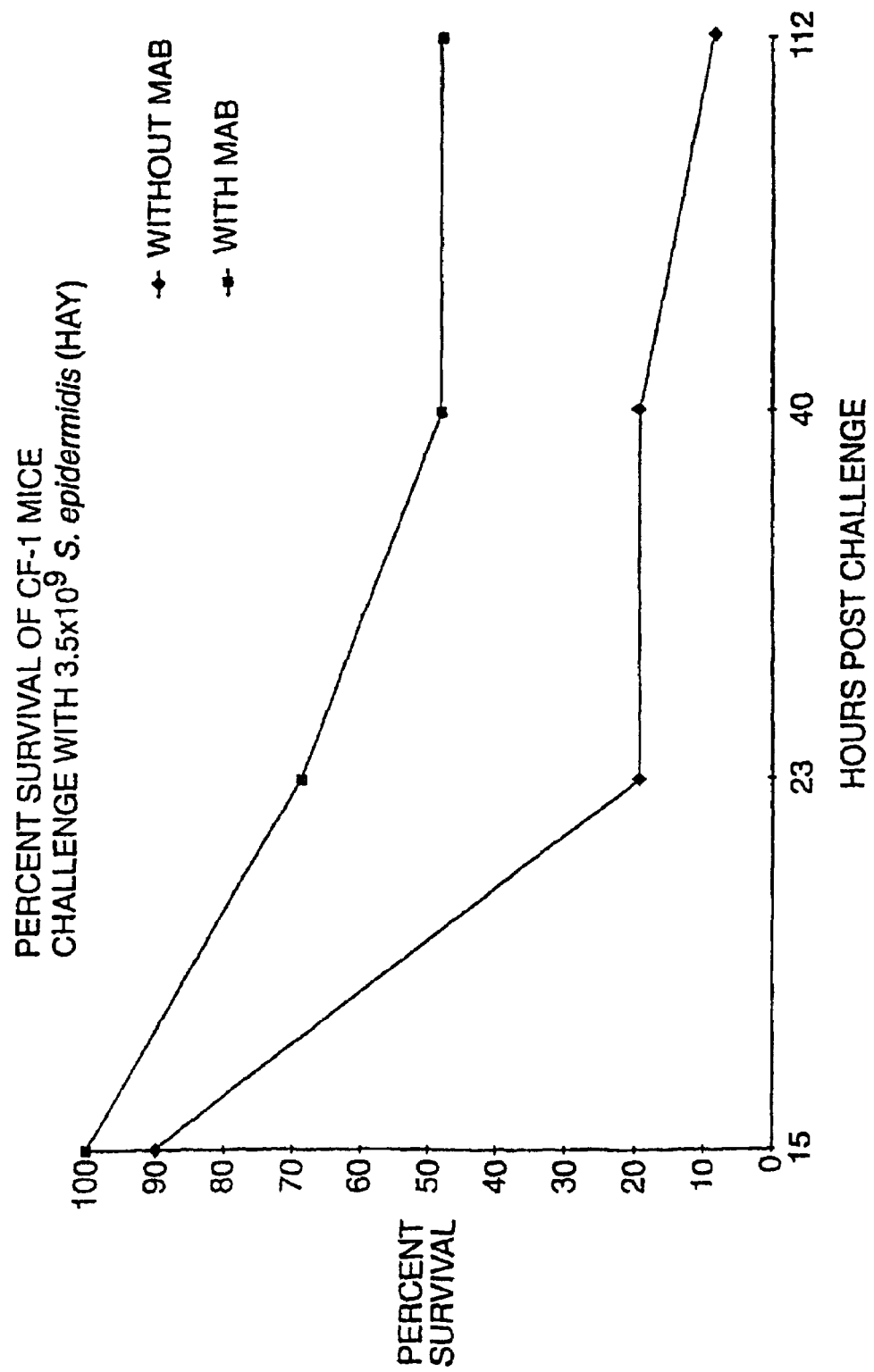
FIG. 4 demonstrates enhancement of survival in adult mice infected with coagulase negative staphylococci after administration of MAB 96-110. Approximately 23 hours after infection, 70% of the animals treated with MAB 96-110 were alive compared with 20% of animals not given antibody.

In a similar manner MAB 96-110 enhanced survival in adult mice infected with coagulase negative staphylococci. Adult CF1 mice were given 0.5 ml *S. epidermidis* (Hay) IP (3.5×10⁹ bacteria). About 24 hrs and 2 hrs before and 24 hrs post-infection, 320 ug of MAB 96-110 were given to one group of mice and compared with a second group infected in the same manner, but not treated with antibody. All animals were followed 5 days to determine survival. Approximately 23 hours after infection, 70% of the animals treated with MAB 96-110 were alive compared with 20% of animals not given antibody (FIG. 4). When the study was terminated 50% of the MAB animals remained alive compared to only 10% of controls.

Thus, MAB 96-110 could enhance survival in lethal coagulase positive and coagulase negative staphylococcal infections. This enhancement occurred in an adult model and an immunocompromised model (immature neonatal immune system).

EXAMPLE 4

Peptide selection Panning random 6mer and 15mer fd-tet phage libraries

Amplified random 6mer and 15mer fd-tet phage libraries were panned against the 96-110 antibody to yield populations of 6 and 15 amino acid length peptides which cross react with the 96-110 antibody. The original libraries were acquired from George P. Smith, Division of Biological Sciences, University of Missouri, Columbia, Mo., In order to be used for panning, the 96-110 antibody was crosslinked to Biotin using the Sulfo-NHS-biotin ester crosslinking kit following the manufacturers protocol (Pierce Chemical Co.).

For the first round of panning, 35 mm polystyrene petri dishes (Costar) were coated with streptavidin by incubating the plates overnight at 4° C. rocking with 100 mM NaHCO$_3$ and 10 ug streptavidin. Streptavidin was then discarded and plates were filled with blocking solution (0.1M NaHCO$_3$, 5 mg/ml dialyzed BSA, 0.1 ug/ml streptavidin) and incubated for 1 hr at 4° C. The following protocol was then followed: Wash dishes six times with TBS/Tween (50 mM Tris-HCl pH 7.5, 150 mM NaCl, 0.5% v/v Tween 20). Incubate dishes overnight at 4° C. rocking with 400 ul TBS/Tween containing 1 mg/ml dialyzed BSA and 10 ug biotinylated 96-110 antibody. Add 4 ul 10 mM biotin and allow to incubate 1 hr at 4° C. rocking. Wash dishes six times as previously stated. Add 400 ul TBS/Tween into each dish, add 4 ul 10 mM biotin and add approximately 5 ul of either the 6mer or 15mer amplified fd-tet phage library (at 1×10¹⁴ vir/ml). Rock dishes 4 hrs at 4° C. Pour out phage and wash ten times with TBS/Tween. Incubate plates at room temp with 400 ul elution buffer (0.1N HCl, pH adjusted to 2.2 with glycine, 1 mg/ml BSA) for 10 min with rocking. Remove eluate to a Centricon 30 (Amicon) concentrator and buffer exchange with TBS (50 mM Tris-HCl pH 7.5, 150 mM NaCl) and concentrate to a volume of about 100 ul. Amplify eluate by mixing 100 ul eluate with 100 ul K91 terrific broth cells and allowing phage to infect cells for 10-30 min. Pipette infection mixture into 20 ml pre-warmed NZY medium (10 g NZ amine A, 5 g yeast extract, 5 g NaCl, 1 liter water, adjust to pH 7.5, autoclave) containing 0.2 ug/ml tetracycline. Shake vigorously at 37° C. for 30-60 min. Add 20 ul of 20 mg/ml tetracycline stock to the flask. Remove a small sample for titering on plates and allow flask to shake vigorously overnight at 37° C. Calculate yield from biopanning using the number of colonies counted on the titering plates from amplification infection and the number of input phage at the beginning of panning. This number should amount to at least approximately 10⁻⁵%. Centrifuge 20 ml culture for 10 min at 5,000 rpm, then for 10 min at 10,000 rpm; pour the doubly cleared supernatant into a fresh tube containing 3 ml PEG/NaCl (16.7% PEG 8000, 3.3M NaCl). Mix well and allow to incubate overnight at 4° C. Centrifuge tube 15 min at 10,000 rpm, discard supernatant and redissolve phage pellet in 1 ml TBS. Collect resuspended phage into a 1.5 ml eppendorf tube, clarify the suspension by centrifugation, and add 150 ul PEG/NaCl. Allow to incubate on ice for 1 hr. Microfuge the tube 10 min, discard supernatant, and redissolve phage in 200 ul TBS.

The second and third round of panning are carried out the same way. The eluted, amplified phage (100 ul) from the previous panning is preincubated with biotinylated 96-110 antibody (100 nM for the second round; 0.1 nM for the third round) overnight at 4° C. 400 ul TBS/Tween is added to the mixture and it is pipetted onto streptavidin coated plates (prepared as previously stated) and then incubated with rocking gentle at room temperature for 10 min. The plates are then washed, eluted, and amplified as previously stated. The input and resultant phage are titered to determine yield from biopanning.

EXAMPLE 5

Sequencing Resulting Phage Populations to Identify Consensus Sequences

Figure 7:
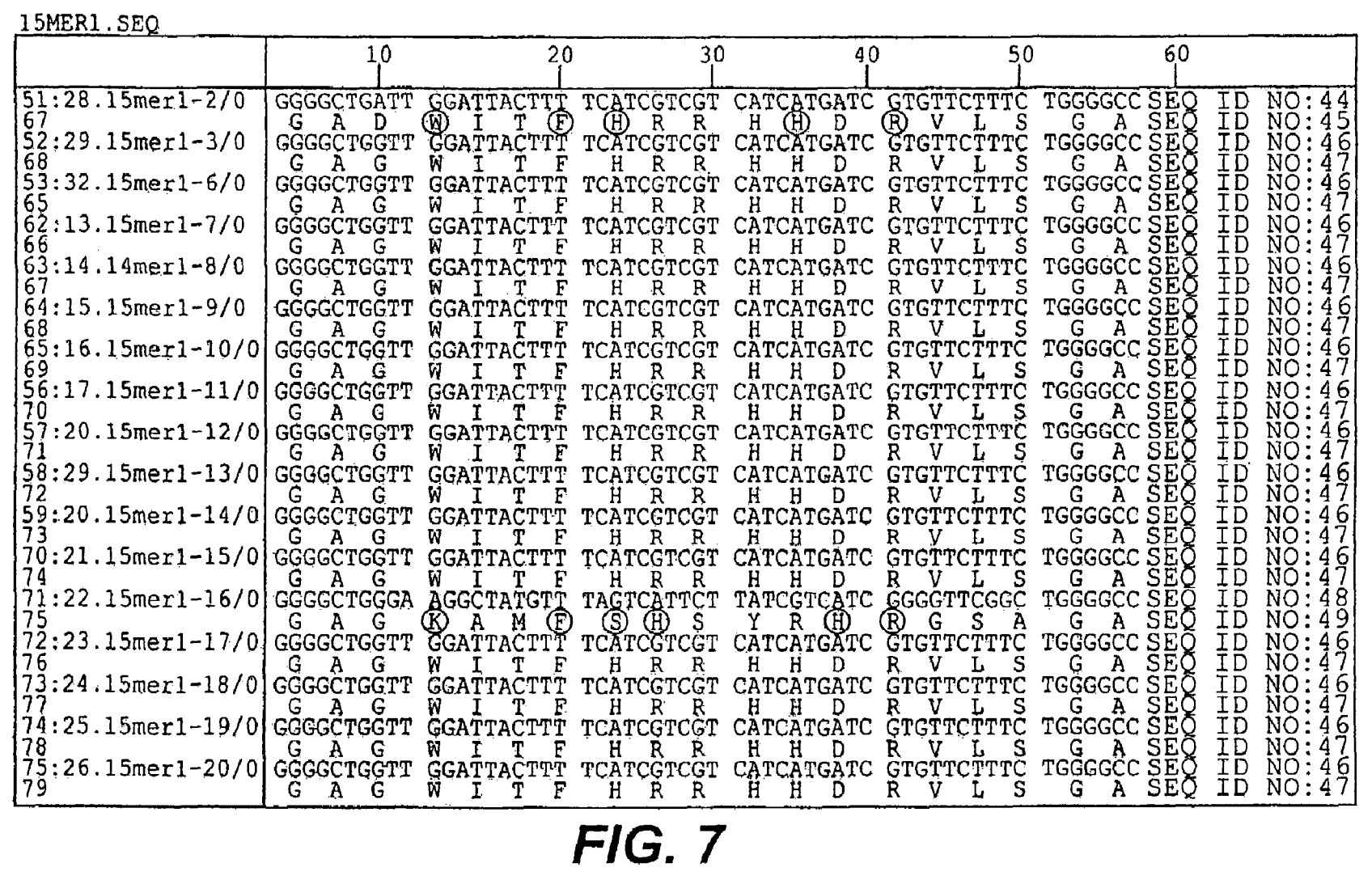

After the third round of panning, the titered infection plates are used to pick 20 single isolated colonies for each library. The colonies are grown overnight in 5 ml NZY medium containing 40 ug/ml tetracycline. Replicative form DNA is extracted from each culture using Qiaplasmid quick prep kit (Qiagen Inc.) following the manufacturer's protocol. Media supernatants are saved for phage stock to be used in Example 4. 2.5 ul of each RF DNA sample is added to a reaction containing 3.5 pmole CLC502 primer (5'-TGAATTTTCTG-TATGAGGTTT-3') (SEQ ID NO 3), 8 UI Prizm sequencing mix (ABI Inc.), QS to 20 ul with water and amplified following manufacturers protocol. Successful sequences are translated and aligned. 18 resulting sequences for the 6mer library panning are listed in FIG. 5. 18 resulting sequences for the second experiment 15mer library panning are listed in FIG. 6. 17 resulting sequences for the first experiment 15mer library panning are listed in FIG. 7. A master list was compiled of the common resulting peptide sequences from all the pannings (FIG. 8) with the frequency of occurrence listed to the right of each sequence. Consensus portions of the sequences are marked on the master list (FIG. 8).

EXAMPLE 6

Phage EIA Comparing 3rd Round Phage Isolates Crossreactivity to 96-110 Antibody

Figure 9:
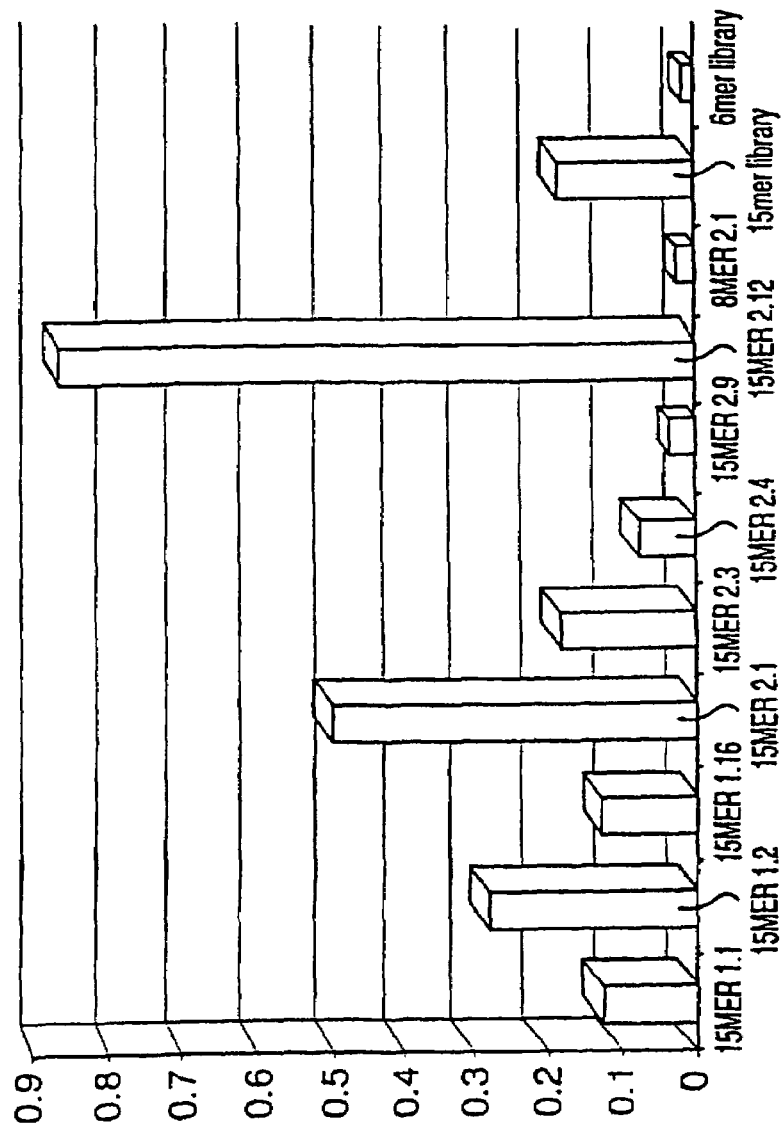
FIG. 9 sets forth a comparison of the optical density signals of each phage isolate at $6.25 \times 10^{11}$ vir/ml.

The saved media phage stocks for each of the common resulting peptide sequences were amplified as previously stated. Amplified phage preparations were quantitated by Abs$_{269}$ and diluted to 1×10¹³ vir/ml and serially diluted 1.2 seven times. A 96-well polystyrene plate was coated with 2 ug/ml streptavidin in 0.1M NaHCO$_3$ overnight at 4° C. Plates were emptied and blocked for 1 hr at room temperature with phage blocking solution, 100 ul/well. The following protocol was then followed. Wash wells three times with TBS/Tween. Incubate overnight at 4° C. with 0.2 ug/ml biotinylated 96110 in phage blocking solution, 100 ul/well. Wash wells three times with TBS/Tween. Incubate overnight at 4° C. with serially diluted phage, 100 ul/well. Wash wells three times with TBS/Tween. Incubate 1 hr at room temperature with 1:5000 goat polyclonal anti-phage-HRP. Wash wells three times with TBS/Tween. Develop with 100 ul ABTS substrate (Kirkegaard Perry) for 10-15 min and read absorbance (402 nm) on spectrophotometer according to manufacturer's protocol. Optical density signals of each phage isolate at 6.25× $10^{11}$ vir/ml are compared in FIG. 9. The two isolates yielding the greatest signals are:

```
15mer 2.12
W R M Y F S H R H A H L R S P    (SEQ ID NO:1)

15mer 2.1
W H W R H R I P L Q L A A G R    (SEQ ID NO:2)
```

EXAMPLE 7

Antibodies Against Lipoteichoic Acid (LTA)

As set forth above, we identified two peptides that reacted with 96-110 MAB. However, after identifying the peptides, the sequences did not correspond to any known proteins. Thus we began to consider other possible antigen candidates. We were surprised to find that MAB 96-110 bound strongly to LTA from several gram positive bacteria such as *S. mutans, S. aureus* and *S. faecalis* (Table 8). In addition, in an ELISA, when the wells coated with *S. epidermidis* (Strain Hay) were reacted with MAB 96-110 inhibited by varying concentrations of LTA (from *S. mutans, S. aureus* and *S. faecalis*), reduction in MAB binding occurred (Table 9). The inhibition of MAB 96-110 binding was greatest at the highest concentration of LTA inhibitor (9 ug/ml for each LTA) and varied according to which bacterial LTA was used (52% inhibition with *S. mutans*, 40.6% with *S. aureus* and 38.2% with *S. faecalis*).

The MAB 96-110 was also analyzed for binding to LTA from *S. pyogenes* (group A *streptococcus*) and various group A streptococcal M types. The MAB showed strong binding to the LTA and also bound to the different M types with strongest binding to M1 and M3 (Table 10).

We were surprised to find an antibody that bound to LTA and enhanced opsonization for both coagulase positive and coagulase negative staphylococci in vitro and enhanced survival in lethal models of staphylococcal (coagulase negative and coagulase positive) sepsis, in vivo. This is particularly surprising because the bacteria in each model were injected systemically (SQ or IP) and by-passed the epithelial barriers (skin or mucous membranes) where LTA is thought to possibly act as an adherence factor for the bacteria to epithelial cells.

In addition, this strong anti-LTA reactivity will provide a method to block the binding of LTA bearing bacteria to epithelial cells and prevent colonization of important pathogens such as staphylococci, group A streptococci, *S. faecalis* (enterococci) and *S. mutans*. Since LTA induces proinflammatory cytokines such as TNF, IL-6 and Interferon gamma, MABs with strong anti-LTA binding will also have an anti-inflammatory action and modulate cytokine production secondary to LTA bearing bacteria. Anti-LTA antibodies or vaccines could be designed and produced to modulate cytokine production and inflammation in tissues and prevent the adverse effects of these proinflammatory cytokines.

TABLE 8

Reactivity of Anti-Hay MAB 96-110 on wells Coated with Several LTA's

| Antibody ID | Concentration or Dilution | LTA from *S. mutans* | LTA from *S. aureus* | LTA from *S. faecalis* |
|---|---|---|---|---|
| Buffer | — | 0.145 | 0.172 | 0.140 |
| Anti-Hay | 0.9 ug/ml | 3.899 | 3.253 | 3.153 |
| MAB 96-110 | 0.3 ug/ml | 3.523 | 2.824 | 2.769 |
|  | 0.1 ug/ml | 2.023 | 2.421 | 2.133 |
|  | 0.033 ug/ml | 2.143 | 1.590 | 1.539 |
|  | 0.011 ug/ml | 1.396 | 0.998 | 0.832 |

TABLE 9

Inhibition of Anti-Hay MAB 96-110 with LTA From Different Gram Positive Bacteria

| LTA Inhibitor (ug/ml) | LTA *S. mutans* | LTA *S. aureus* | LTA *S. faecalis* |
|---|---|---|---|
| 9 | 0.298 | 0.360 | 0.140 |
| 3 | 0.449 | 0.434 | 0.496 |
| 1 | 0.549 | 0.538 | 0.545 |
| 0.37 | 0.558 | 0.526 | 0.549 |
| 0.12 | 0.509 | 0.735 | 0.582 |
| 0.04 | 0.574 | 0.614 | 0.671 |
| 0 | 0.621 | 0.607 | 0.648 |

NOTES:
1. Wells were coated with methanol-fixed Hay.
2. Wells were blocked with 1% BSA in PBS.
3. Monoclonal anti-Hay was used at a final concentration of 0.5 ug/ml and reacted with inhibitors at the concentrations indicated in the Table.
4. Detection was with a gamma-specific Rabbit anti-Mouse.
5. Substrate was TMB.

TABLE 10

Reactivity of MAB 96-110 on Whole Methanol Fixed Group A *Strep*

| Antibody ID | Dilution or Conc. | GAS* Type 1 #12344 | GAS Type 3 #21546 | GAS Type 18 #12357 | GAS Type 24 #10782 | Response on pyogenes LTA |
|---|---|---|---|---|---|---|
| Buffer |  | 0.511 | 0.161 | 0.234 | 0.148 | 0.075 |
| Anti-Hay MAb | 0.3 ug/ml | 1.377 | 1.113 | 0.844 | 0.566 | — |
| Anti-Hay Mab | 0.1 ug/ml | 1.016 | 0.553 | 0.555 | 0.402 | 2.228 |

*All Group A *Streptococcus* (GAS) from ATCC (accession numbers noted above); plates were coated with MeoH-fixed bacteria and read at 15 minutes.

EXAMPLE 8

Humanization of the Anti-*Staph* Antibody 96-110
Cloning of the 96-110 Variable Region cDNAs The hybridoma cell producing the 96-110 antibody was obtained as described above. A vial of cells was thawed, washed with serum free medium and then resuspended in IMDM (Mediatech) complete media supplemented with 10% FBS (Irvine). Total RNA was isolated from 1×10⁸ 96-110 cells using the Midi RNA Isolation kit (Qiagen) following the manufacturer's procedure. The RNA was dissolved in 10 mM Tris, 0.1 mM EDTA (pH8.4) containing 0.03 U/μg Prime RNase Inhibitor (5'-3') to a final concentration of 0.25 μg/μl.

Figure 10:
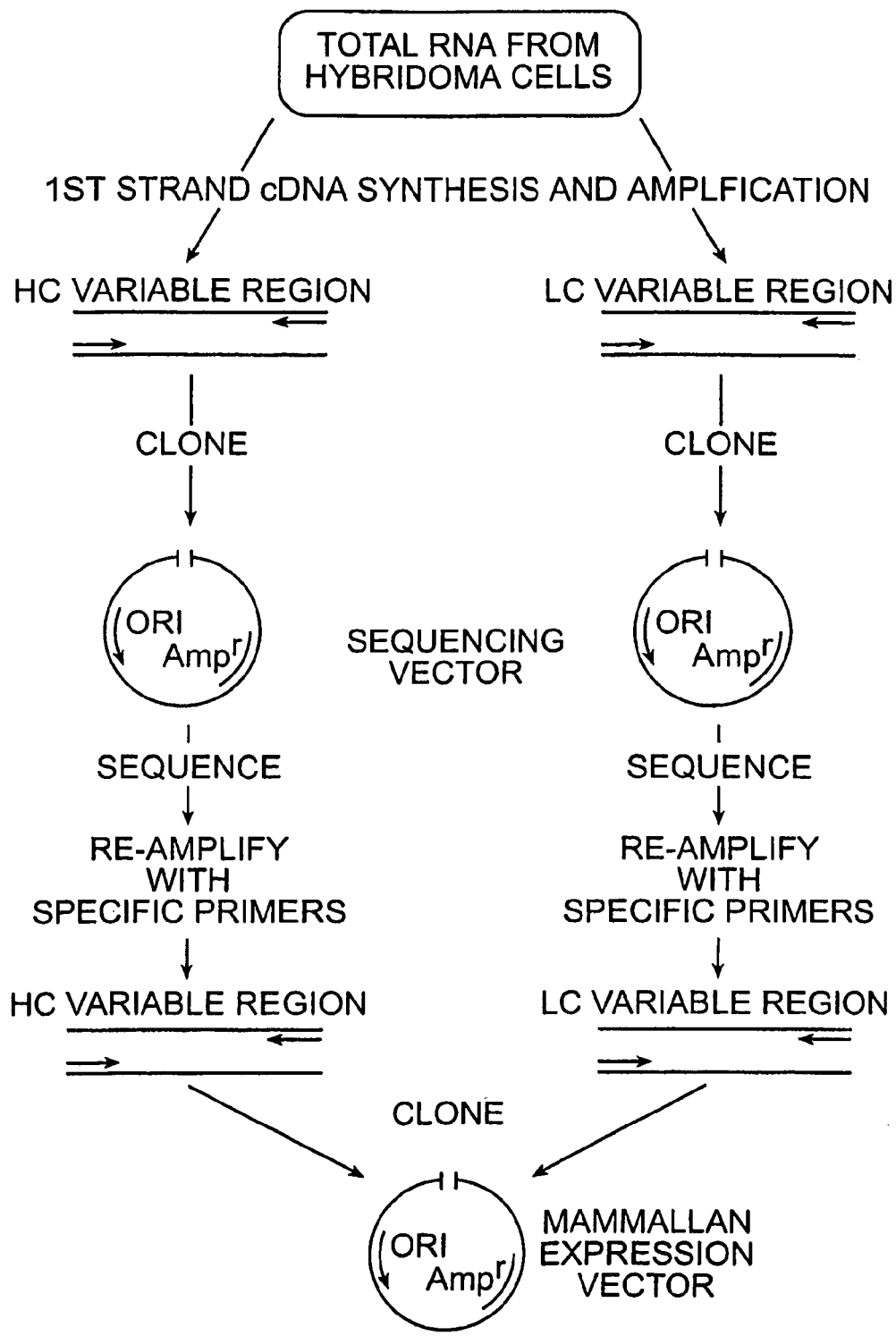
FIG. 10 shows the strategy for cloning the variable region gene fragments.

FIG. 10 shows the strategy for cloning the variable region gene fragments and FIG. 11 lists the oligonucleotides primers used. The 96-110 total RNA (2 μg) was converted to cDNA by using Superscript II-MMLV Reverse transcriptase (Life Technologies) and mouse kappa (OKA57) and mouse heavy chain (JS160-162)-specific priming according of manufacturer's procedures. The first strand cDNA synthesis products were then purified using a Centricon-30 concentrator device (Amicon). Of the 40 μl of cDNA recovered, 5 μl was used as template DNA for PCR. Typical PCR amplification reactions (100 μl) contained template DNA, 50 pmoles of the appropriate primers (PMC12-15,55 and OKA57 for tight chains, JSS1-4,8 and JS 160-162 for heavy chains), 2.5 units of Ex Taq polymerase (PanVera), 1× Ex Taq reaction buffer, 200 μM dNTP, 1 mM MgCl₂. The template was denatured by an initial incubation at 96° C. for 5 min. The products were amplified by 15 thermal cycles of 55° C. for 30 sec., 70° C. for 30 sec, then 96° C. for 1 min. followed by 25 step cycles of 70° C. for 1 min., then 96° C. for 1 min. The PCR products from the successful reactions were purified using the Wizard PCR Purification system (Promega) as per manufacturer's procedure.

The heavy chain PCR products (approximately 400 bp) were then cloned into a bacterial vector for DNA sequence determination. Ligations of the PCR fragments were carried out into the PCR2.1 (invitrogen) T/A style cloning vector following the manufacturer's procedures using a 3:1 insert to vector molar ratio. One half (5 ul) of the ligation reactions were used to transform Ultracompetent XL2Blue cells (Stratagene) as per the manufacturer's procedure. Plasmid clones containing DNA inserts were identified using diagnostic restriction enzyme digestions with NcoI (New England Biolabs). The DNA sequence of plasmids (pJRS308) containing inserts of the appropriate size (400 bp) was then determined. The final consensus DNA sequence of the heavy chain variable regions is shown in FIG. 12.

The light chain PCR products were treated differently. The hybridoma cell line that expresses the 96-110 antibody was made by fusing mouse spleenocytes with the SP20 myeloma cell line. The SP20 cell line transcribes a pseudogene for the kappa light chain. In addition, the hybridoma cell line that expresses the 96-110 antibody transcribes a second pseudogene product for a kappa light chain that apparently arose from the spleenocyte partner of the hybridoma fusion event. This second pseudogene transcript can be expressed from an expression vector transfected into mammalian cells, but this recombinant antibody product does not bind to heat-killed Staph HAY cells in an ELISA (see Example 9). Both of these pseudogene transcripts, when converted to cDNA by RT-PCR, contain an Af/III restriction site. For this reason, the PCR products synthesized for the light chain variable region was digested with Af/III and those products that did not cut were then cloned into the pGEM T-Easy (Promega) T/A style cloning vector using the manufacturer's procedures. Light chain candidate (pJRS319) clones were digested with EcoRI (New England Biolabs) using the manufacturer's procedures to identify clones containing inserts of the appropriate size (350 bp). The final consensus DNA sequence of the light chain variable regions is shown in FIG. 12. The amino acids encoded by these sequences match the N-terminal amino acid analyses of the heavy and light chain peptide fragments produced by the hybridoma cell line.

The heavy and light chain variable regions were then subcloned into a mammalian expression plasmid vector pSUN 15 for production of recombinant chimeric antibody molecules. The creation of the expression vector was an extensive process of DNA fragment ligations and site directed mutagenesis steps. The result was a vector that expresses both antibody chains with CMV promoter driven transcription. Neomycin resistance serves as a dominant selectable marker for transfection of mammalian cells. In addition, it has been designed to allow convenient cloning of any light chain variable region as EcoRVI BstBI fragment, any heavy chain variable region as a NruI/EcoRI fragment, and any heavy chain constant domain as an EcoRIINotI fragment. These restriction sites were chosen because they occur rarely (if ever) in human and mouse variable regions. There is a mouse J region/kappa intron fragment fused to a human kappa exon so that after post transcriptional splicing a mouse human chimeric kappa light chain is produced.

The backbone of the vector was the plasmid pcDNA3 (Invitrogen). This plasmid was cut with HindIII/XhoI and a "light chain polylinker" DNA fragment was inserted to create the stated "light chain vector." This linker contained the restriction sites HindIII, KpnI, Cla/, Pm/I, EcoRV Xmal, BamHI and XhoI to facilitate subsequent cloning steps to create the plasmid pcDNA3.LCPL. A SmaI/BclI DNA fragment containing a light chain leader, anti-CKMB kappa light chain genomic fragment, and 3' UTR was cloned into the EcoRV/BamHI sites of pcDNA3.LCPL. The mouse kappa intron, exon and 3' UTR in this fragment was derived from LCPXK2 received from Dr. Richard Near (Near, RI et al, 1990, Mol Immunol. 27:901-909). Mutagenesis was then performed to eliminate an NruI (209), MluI (229). and BstBI (2962) and to introduce an NheI (1229) and a BamHI (1214) site to create pcDNA3mut.LCPL.LCVK.

A second "heavy chain vector" was constructed from the pcDNA3mut. LCPL.LCVK plasmid by replacing the light chain expression region (HindIII/XhoI) with a "heavy chain polylinker" consisting of restriction sites HpaI, BspEI, EcoRV, KpnI, and XhoI. A Small KpnI DNA fragment contains a heavy chain leader, antiCKMB IgG2b chain genomic fragment. A KpnI/SalI oligo nucleotide fragment containing a 3' UTR and a NotI upstream of the SalI site was subsequently cloned into the KpnI/XhoI digested plasmid, (knocking out the XhoI site) to create the plasmid pcDNA3mut.HCPL.HCV2b. From this point two vectors were created that did not have any of the anti-CKMB variable or constant domain DNA sequences. This was done by cutting the plasmid pcDNA3mut.LCPL.LCVK with EcoRV/XhoI and inserting a linker oligonucleotide fragment containing EcoRV, BstBI, and XhoI sites to create pSUN9. In a similar way, the anti-CKMB fragment in pcDNA3mut.HCPL.HCV2b (NruI/NotI) was replaced by a linker oligonucleotide fragment containing NruI, EcoRI and NotI sites to create pSUN1O. A human kappa light chain constant domain was then cloned into pSUN9 as a BstB/XhoI fragment, and a human IgG1 constant domain was cloned into pSUN10 as a EcoRI/NotI fragment. A BgIII/NheI fragment from the human heavy chain vector was then cloned into the human light chain vector cut with BamHI/NheI to create pSUNI5. This vector results in the production of recombinant antibody molecules under the control of the CMV transcriptional promoters. The heavy chain molecules are direct cDNA constructs that fuse the variable region sequence directly into the human IgG1 constant domain. The light chain molecules, on the other hand, have a mouse kappa intron region 3' of the variable region coding fragment. After splicing the variable region becomes fused to a human kappa constant region exon. The selectable marker for the vector in mammalian coils is Neomycin (G418).

The variable region gene fragments were re-amplified by PCR using primers that adapted the fragments for cloning into the expression vector (see FIGS. 12 and 14). The heavy chain front primer (96110HF2) includes a 5' tail that encodes the C-terminus of the heavy chain leader and an NruI restriction site for cloning, while the heavy chain reverse primer (96110HB) adds a 3' EcoRI restriction site for cloning. The light chain front primer (96110 bLF) converts the first amino acid of the 96-110 light chain variable region sequence from glutamine (Q) to aspartic acid (D) via the introduction of an EcoRV restriction site at the N-terminus of the light chain variable region for cloning, while the light chain reverse primer (96-110bLB) adds a 3' DNA sequence for the joining region-kappa exon splice junction followed by a BstBI restriction site for cloning. Because the last amino acid of the light chain variable region is an arginine (R) which is a very rare amino acid at this position, the reverse primer introduces a point mutation in the codon for amino acid 106 that converts it to the much more common lysine (L). This was done because the splice junction in the expression vector for the kappa chain was derived from a J region that encoded a lysine at this position. Neither mutation in the recombinant form of the antibody would be anticipated to alter the antibodies binding characteristics. The amino acid sequence of this version of Hu96-110 is set forth as SEQ ID NO:90.

PCRs were performed as described above except 10 ng of plasmid template was used in each case. Following a 5 min. incubation at 96° C., the PCR perimeters were 35 thermal cycles of 58° C. for 30 sec., 70° C. for 30 sec., and 96° C. for 1 min. The 96-110 heavy chain PCR product (approximately 400 bp) was digested with NruI and EcoRI (New England Biolabs), purified using a Qiaquick PCR Purification column (Qiagen), as described by the manufacturer, and ligated into NruI/EcoRI digested and gel-purified pSUN15, resulting in plasmid pJRS311 (see FIG. 13).

At this point a BstBI/NotI (New England Biolabs) DNA fragment containing a mouse kappa J-kappa intron fragment fused to a human kappa exon fragment was digested and gel-purified from the vector tKMC180C1. This fragment was ligated into the backbone of pJRS311 digested with BstBI/NotI and gel-purified resulting in the plasmid pJRS315 (see FIG. 13).

This was the plasmid into which was cloned the 96-110 light chain variable region. The 96-110 light chain PCR product (approximately 350 bp) was digested with EcoRV and BstBI (New England Biolabs), purified using a Qiaquick PCR Purification column (Qiagen), as described by the manufacturer, and ligated into EcoRV/Bs/BI digested and gel-purified pJRS315, resulting in plasmid pJRS326 (see FIG. 13).

It was determined that during this cloning process, a deletion of approximately 200 bp occurred at the intron exon junction of the kappa light chain. To repair this, an identical DNA fragment (also a BstBI/NotI restriction fragment) was gel-purified from digested pEN22 and ligated into BstBI/NotI digested and gel-purified pJRS326, resulting in the final expression plasmid construct pJRS334 (see FIGS. 13 and 14).

The sequence of the variable regions and leader and other junctions was verified prior to mammalian cell transfection.

EXAMPLE 9

Transient Production of Recombinant Chimeric Mouse/Human 96-110 Antibody

Two individual clones of the plasmid pJRS334 (pJRS334-1, -2) were transfected into COS and CHO cells using Superfectant (Qiagen) in 6 well tissue culture cells as described by the manufacturer. After three days the supernatant was assayed for the production of "humanized" antibody and for the capability for the expressed antibody to bind to the heat-killed Staph antigen.

Antibody production assays were preformed in 8-well strips from 96-well microtiter plates (Maxisorp F8; Nunc, Inc.) coated at a 1:500 dilution with Goat anti-Human IgG antibody (Pierce) using a bicarbonate coating buffer, pH 8.5. The plates are covered with pressure sensitive film (Falcon, Becton Dickinson) and incubated overnight at 4° C. Plates are then washed once with Wash solution (Imadazole/NaCl/0.4% Tween-20). 100 microliters of culture supernatant was then applied to duplicate wells and allowed to incubate for 30 minutes on plate rotator at room temperatures. The plates were washed five times with Wash solution. A Goat anti Human kappa-HRP (Southern Biotechnologies) conjugate was diluted 1:800 in the sample/conjugate diluent. 100 microliters was added to the samples, then incubated on a plate rotator for 30 minutes at room temperature. The samples were washed as above and then incubated with 100 µL/well of ABTS developing substrate (Kirkgaard & Perry Laboratories) for 10-15 minutes on a plate rotator at room temperature. The reaction was stopped with 100 µL/well of Quench buffer (Kirkgaard & Perry Laboratories) and the absorbance value at 405 nm was determined using an automated microtiter plate ELISA reader (Ceres UV900HI, Bioteck, Winooski, Vt.). As a positive control, a humanized mouse/human chimeric antibody BC24 was used. This assay (see FIG. 15) demonstrates that the transfection of cells with this plasmid construct to results in the cells producing a molecule containing both human IgG and kappa domains. The supernatants were then assayed for the ability of the expressed antibodies to bind to heat-killed *Staph*. The activity assays were preformed in 8-well strips from 96-well microtiter plates (Maxisorp F8; Nunc, Inc.) coated at 0.09 OD/well with heat-killed *Staph* Hay cell material suspended in MeOH. The plates are left uncovered and incubated overnight at 4° C. Plates are then washed once PBS. 100 microliters of culture supernatant was then applied to duplicate wells and allowed to incubate for 60 minutes on plate rotator at room temperature. The plates were washed five times with Wash solution. The goat anti Human kappa-HRP was diluted 1:800 in the sample/conjugate diluent. 100 microliters was added to the samples, then incubated on a plate rotator for 30 minutes at room temperatures. The samples were washed as above and then incubated with 100 µL/well of ABTS developing substrate (Kirkgaard & Perry Laboratories) for 10-15 minutes on a plate rotator at room temperature. The reaction was stopped with 100 µL/well of Quench buffer (Kirkgaard & Perry Laboratories) and the absorbance value at 405 nm was determined using an automated microtiter plate ELISA reader (Ceres UV900HI, Bioteck, Winooski, Vt.). As a positive control, the original mouse monoclonal antibody 96-110 was used, and assayed with a Goat anti-Mouse Fc-HRP conjugate @ 1:2000 dilution. This assay (see FIG. 16) demonstrates that the transfection of cells with this plasmid construct to results in the cells producing a molecule that binds to the *Staph* Hay cellular antigen.

EXAMPLE 10

Stable Production of Recombinant Chimeric Mouse/Human 96-110 Antibody

The plasmid pJRS334-1 was transfected into NS/0 cells (obtainable from Baxter International) and CHO cells using electroporation. The plasmid was linearized with PvuI restriction digestion. 25 micrograms of digested plasmid DNA was mixed with $1\times10^7$ cells in a total volume of 800 microliters in a 4 centimeter cuvette and subjected to a pulse of 250 mA, 9600 microF. The cells were plated out after 24 hours in 10 ml non-selective media. The cells were then diluted out into 96-well microtiter plates. As colonies appeared, the supernatants were assayed for the production of "humanized" antibody and for the capability for the expressed antibody to bind to the heat-killed *Staph* antigen. Antibody production and activity assays for the stable transfectants were performed as described above. These assays demonstrate that the transfection of cells with this plasmid construct can result in the production of a stable cell line that produces a humanized chimeric version of the 96-110 mouse hybridoma antibody.

EXAMPLE 11

Opsonic Activity

Having produced a chimeric anti-LTA MAB for staphylococci, we tested its functional activity using *S. epidermidis* as a representative staphylococcal organism. Using the neutrophil mediated opsonophagocytic assay described generally in the Material and Methods section, we assessed the MAB's opsonic activity by evaluating the percent of bacteria killed after two hours of incubation.

Neutrophils, specifically polymorphonuclear neutrophils, were isolated from adult venous blood by dextran sedimentation and ficoll-hypaque density centrifugation. Washed neutrophils were added to round-bottomed wells of microtiter plates (approximately $10^6$ cells per well) with approximately $3\times10^4$ mid-log phase bacteria (*S. epidermidis* Hay, ATCC 55133). Human sera (10 uls), screened to assure absence of antibody to *S. epidermidis*, was used as a source of active complement (C-Barb-Ex (1:4)).

Forty microliters of immunoglobulin were added at various concentrations (20 ug/ml, 40 ug/ml, 80 ug/ml, and 160 ug/ml) and the plates were incubated at 37° C. with constant, vigorous shaking. Samples of 10 uls were taken from each well at zero time and after 2 hours of incubation. Each was diluted, vigorously vortexed to disperse the bacteria, and cultured on blood agar plates overnight at 37° C. to quantitate the number of viable bacteria. Results are presented in FIG. 17 as percent reduction in numbers of bacterial colonies observed compared to control samples. Compared to PMN alone or PMN plus complement, the addition of the MAB markedly enhanced opsonic activity for *staphylococcus* at 20-160 ug/ml). These data demonstrate that the MAB has functional activity and can enhance the phagocytosis and killing of staphylococcal organisms, as represented by *S. epidermidis*.

EXAMPLE 12

In vivo Protective Efficacy

Using the lethal staphylococcal sepsis in adult mice assay (described in Example 3), we compared protection between the original mouse MAB and the chimeric HuMAB. Adult CF1 mice were given 0.5 ml *S. epidermidis* (Hay) IP ($3.5\times10^9$ bacteria). About 24 hrs and 1 hr before infection, 14 mg/kg of each MAB was given to a group of mice, with a third group of mice given only PBS. All animals were followed for 40 hours after challenge to determine survival.

As set forth in FIG. 18, approximately 18 hours after infection, all the control animals died while both treatment groups exhibited 100% survival. At 30 hours after infection, both MAB treatment groups exhibited 70% survival. At the end of the study, the group that received the mouse MAB exhibited greater survival than the group receiving the chimeric MAB, but both MAB enhanced survival over the PBS controls.

We conducted further studies with the chimeric MAB at a dose of 18 mg/kg/dose 2 doses given IP 24 and 1 hour prior to infection ($3\times10^9$ IP *S. epidermidis*, Hay). As set forth in FIG. 19, the chimeric MAB enhanced survival.

We also assessed the effect of the chimeric MAB on bacteremia in the lethal *S. epidermidis* sepsis model. CF-1 mice were twice infected IP with strain Hay and the chimeric MAB. Bacteremia is expressed as the number of bacteria isolated on blood agar after a 1:1000 dilutions. As set forth in FIG. 20, the chimeric MAB reduced bacterial levels by over 2 logs. Additional studies demonstrated that bacteremia was reduced to a greater degree using 40 mg/kg/dose compared to 20 mg/kg/dose even if survival was comparable. See FIG. 21.

These data indicate that increasing the amount of antibody resulted in increased bacterial clearance in vivo. Such a response is similar to the observed enhanced opsonic activity in vitro as seen when antibody was increased from 20 ug/mg to 160 ug/ml in the neutrophil mediated opsonophagocytic assay (FIG. 17).

EXAMPLE 13

In vivo Protective Efficacy

The effect of the chimeric MAB 96-110 was then analyzed in a neonatal staphylococcal model using suckling rats with a foreign body infection. Two day old Wistar rats were treated with lipid emulsion (as is standard in newborn care for nutritional purposes) 0.2 ml, 20% IP on day −1 and again on day +1 and +2 to induce further compromise of the immuno system. In two studies, we injected approximately $5\times10^7$ of four different strains of *S. epidermidis*, identified below in Table 11 SQ through a plastic catheter and the catheter was left in place under the skin. Saline, 0.2 ml, or MAB 96-110, 0.2 ml (dose of 50-60 mg/kg), was given IP 30 min before and 24 hours after infection. The animals were followed for 5 days.

As set forth in Table 11, in study 1, survival for animals receiving MAB ranged from 67% to 83%, with an average of 76%, in contrast to saline treatment, which ranged from 33% to 50%, with an average of 39%. Study II showed even more impressive results. Survival for animals treated with MAB ranged from 83% to 100%, with 90% average, compared to the saline controls at 33% to 50%, with an average of 40%. The complied data for study 11 are shown in FIG. 22.

TABLE 11

The Effect of Hu96-110 on Survival in a Lethal Neonatal *S. epidermidis* Sepsis Model

| Litter Number | *S. epidermidis* strain | Monoclonal Antibody | | Saline Control | |
|---|---|---|---|---|---|
| | | Treated | Survived (%) | Treated | Survived (%) |
| *Study I* | | | | | |
| 31 | Haywood (type II) (clinical) | 6 | 4 (67%) | 6 | 2 (33%) |
| 32 | 35984 (type I) (Prototype) | 5 | 4 (80%) | 4 | 2 (50%) |
| 33 | Summer (48357) (clinical) | 6 | 4 (67%) | 6 | 2 (33%) |
| 34 | SE-360 (type III) (Prototype) | 6 | 5 (83%) | 6 | 2 (33%) |
| 35 | Haywood (type II) (clinical) | 6 | 5 (83%) | 6 | 3 (50%) |
| TOTAL | | 29 | 22 (76%) | 28 | 11 (39%) |
| *Study II* | | | | | |
| 36 | Haywood (type II) (clinical) | 6 | 6 (100%) | 6 | 3 (50%) |
| 37 | 35984 (type I) (Prototype) | 6 | 5 (83%) | 6 | 2 (33%) |
| 38 | Summer (48357) (clinical) | 6 | 6 (100%) | 6 | 2 (33%) |
| 39 | SE-360 (type III) (Prototype) | 6 | 5 (83%) | 6 | 2 (33%) |
| 40 | Haywood (type II) (clinical) | 6 | 5 (83%) | 6 | 3 (50%) |
| TOTAL | | 30 | 27 (90%) | 30 | 12 (40%) |
| TOTAL OF BOTH STUDIES | | 59 | 49 (88%) | 58 | 23 (40%) |

These data demonstrate that the chimeric human antibody directed against LTA is opsonic and enhances survival against staphylococci. In addition, the antibody promotes clearance of the staphylococci form the blood. Thus antibody to LTA provides prophylactic and therapeutic capabilities against staphylococcal infections and vaccines using LTA or peptide mimeotopes of LTA that induce anti-LTA antibodies would also have prophylactic capabilities.

Having now fully described the invention, it will be appreciated by those skilled in the art that the invention can be performed within a range of equivalents and conditions without departing from the spirit and scope of the invention and without undue experimentation. In addition, while the invention has been described in light of certain embodiments and examples, the inventors believe that it is capable of further modifications. This application is intended to cover any variations, uses, or adaptions of the invention which follow the general principles set forth above.

The specification includes recitation to the literature and those literature references are herein specifically incorporated by reference.

The specification and examples are exemplary only with the particulars of the claimed invention set forth as follows:

```
                         SEQUENCE LISTING (1) GENERAL INFORMATION:

(iii) NUMBER OF SEQUENCES: 89

(2) INFORMATION FOR SEQ ID NO: 1:

(i) SEQUENCE CHARACTERISTICS:
          (A) LENGTH: 15 amino acids
          (B) TYPE: amino acid
          (C) STRANDEDNESS: <Unknown>
          (D) TOPOLOGY: linear (ii) MOLECULE TYPE: peptide (xi) SEQUENCE DESCRIPTION: SEQ ID NO: 1:

Trp Arg Met Tyr Phe Ser His Arg His Ala His Leu Arg Ser Pro
1               5                   10                  15

(2) INFORMATION FOR SEQ ID NO: 2:

(i) SEQUENCE CHARACTERISTICS:
          (A) LENGTH: 15 amino acids
          (B) TYPE: amino acid
          (C) STRANDEDNESS: <Unknown>
          (D) TOPOLOGY: linear (ii) MOLECULE TYPE: peptide
```

(xi) SEQUENCE DESCRIPTION: SEQ ID NO: 2:

Trp His Trp Arg His Arg Ile Pro Leu Gln Leu Ala Ala Gly Arg
 1               5                  10                  15

(2) INFORMATION FOR SEQ ID NO: 3:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 3:

TGAATTTTCT GTATGAGGTT T                                              21

(2) INFORMATION FOR SEQ ID NO: 4:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..30

(xi) SEQUENCE DESCRIPTION: SEQ ID NO: 4:

GGG GCT CAT GCG GAT AGG GTT TAT GGG GCC                              30
Gly Ala His Ala Asp Arg Val Tyr Gly Ala
 1               5                  10

(2) INFORMATION FOR SEQ ID NO: 5:

(i) SEQUENCE CHARACTERISTICS:
        (A) LENGTH: 10 amino acids
        (B) TYPE: amino acid
        (D) TOPOLOGY: linear (ii) MOLECULE TYPE: protein (xi) SEQUENCE DESCRIPTION: SEQ ID NO: 5:

Gly Ala His Ala Asp Arg Val Tyr Gly Ala
 1               5                  10

(2) INFORMATION FOR SEQ ID NO: 6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..30

(xi) SEQUENCE DESCRIPTION: SEQ ID NO: 6:

GGG ANT CAT GCG GAT AGG GTT TAT GGG GCC                              30
Gly Xaa His Ala Asp Arg Val Tyr Gly Ala
 1               5                  10

(2) INFORMATION FOR SEQ ID NO: 7:

(i) SEQUENCE CHARACTERISTICS:
        (A) LENGTH: 10 amino acids
        (B) TYPE: amino acid
        (D) TOPOLOGY: linear (ii) MOLECULE TYPE: protein (xi) SEQUENCE DESCRIPTION: SEQ ID NO: 7:

```
Gly Xaa His Ala Asp Arg Val Tyr Gly Ala
 1               5                  10
```

(2) INFORMATION FOR SEQ ID NO: 8:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..57

(xi) SEQUENCE DESCRIPTION: SEQ ID NO: 8:

```
GGG GCT TGG CAT TGG CGT CAT CGT ATT CCT CTT CAG CTT GCT GCT GGT      48
Gly Ala Trp His Trp Arg His Arg Ile Pro Leu Gln Leu Ala Ala Gly
 1               5                  10                  15

CGT GGG GCC                                                          57
Arg Gly Ala
```

(2) INFORMATION FOR SEQ ID NO: 9:

(i) SEQUENCE CHARACTERISTICS:
        (A) LENGTH: 19 amino acids
        (B) TYPE: amino acid
        (D) TOPOLOGY: linear (ii) MOLECULE TYPE: protein (xi) SEQUENCE DESCRIPTION: SEQ ID NO: 9:

```
Gly Ala Trp His Trp Arg His Arg Ile Pro Leu Gln Leu Ala Ala Gly
 1               5                  10                  15

Arg Gly Ala
```

(2) INFORMATION FOR SEQ ID NO: 10:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..57

(xi) SEQUENCE DESCRIPTION: SEQ ID NO: 10:

```
GGG GCT CGT CGG CAT GGT AAT TTT TCT CAT TTT TTT CAT CGG TCG TTG      48
Gly Ala Arg Arg His Gly Asn Phe Ser His Phe Phe His Arg Ser Leu
 1               5                  10                  15

ATT GGG GCC                                                          57
Ile Gly Ala
```

(2) INFORMATION FOR SEQ ID NO: 11:

(i) SEQUENCE CHARACTERISTICS:
        (A) LENGTH: 19 amino acids
        (B) TYPE: amino acid
        (D) TOPOLOGY: linear (ii) MOLECULE TYPE: protein (xi) SEQUENCE DESCRIPTION: SEQ ID NO: 11:

```
Gly Ala Arg Arg His Gly Asn Phe Ser His Phe Phe His Arg Ser Leu
 1               5                  10                  15

Ile Gly Ala
```

(2) INFORMATION FOR SEQ ID NO: 12:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..57

(xi) SEQUENCE DESCRIPTION: SEQ ID NO: 12:

```
GGG GCT TGG AAG GCT TTG TTT AGT CAT TCT TAT CGT CCT CGG GGT TCG      48
Gly Ala Trp Lys Ala Leu Phe Ser His Ser Tyr Arg Pro Arg Gly Ser
 1               5                  10                  15

GCT GGG GCC                                                          57
Ala Gly Ala
```

(2) INFORMATION FOR SEQ ID NO: 13:

(i) SEQUENCE CHARACTERISTICS:
        (A) LENGTH: 19 amino acids
        (B) TYPE: amino acid
        (D) TOPOLOGY: linear (ii) MOLECULE TYPE: protein (xi) SEQUENCE DESCRIPTION: SEQ ID NO: 13:

```
Gly Ala Trp Lys Ala Leu Phe Ser His Ser Tyr Arg Pro Arg Gly Ser
 1               5                  10                  15

Ala Gly Ala
```

(2) INFORMATION FOR SEQ ID NO: 14:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..57

(xi) SEQUENCE DESCRIPTION: SEQ ID NO: 14:

```
GGG GCT AGG CAT TGG CGT CAT CGT ATT CCT CTT CAG CTT GCT GCT GGT      48
Gly Ala Arg His Trp Arg His Arg Ile Pro Leu Gln Leu Ala Ala Gly
 1               5                  10                  15
```

```
CGT GGG GCC                                                    57
Arg Gly Ala (2) INFORMATION FOR SEQ ID NO: 15:

(i) SEQUENCE CHARACTERISTICS:
        (A) LENGTH: 19 amino acids
        (B) TYPE: amino acid
        (D) TOPOLOGY: linear (ii) MOLECULE TYPE: protein (xi) SEQUENCE DESCRIPTION: SEQ ID NO: 15:

Gly Ala Arg His Trp Arg His Arg Ile Pro Leu Gln Leu Ala Ala Gly
  1               5                  10                  15

Arg Gly Ala (2) INFORMATION FOR SEQ ID NO: 16:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..57

(xi) SEQUENCE DESCRIPTION: SEQ ID NO: 16:

GGG GCT TGG CAT TGG CGT CAT CGT ATT CCT CTT CAG CTT GCT GCT GGT     48
Gly Ala Trp His Trp Arg His Arg Ile Pro Leu Gln Leu Ala Ala Gly
  1               5                  10                  15

CGT GGG GCC                                                    57
Arg Gly Ala (2) INFORMATION FOR SEQ ID NO: 17:

(i) SEQUENCE CHARACTERISTICS:
        (A) LENGTH: 19 amino acids
        (B) TYPE: amino acid
        (D) TOPOLOGY: linear (ii) MOLECULE TYPE: protein (xi) SEQUENCE DESCRIPTION: SEQ ID NO: 17:

Gly Ala Trp His Trp Arg His Arg Ile Pro Leu Gln Leu Ala Ala Gly
  1               5                  10                  15

Arg Gly Ala (2) INFORMATION FOR SEQ ID NO: 18:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..57

(xi) SEQUENCE DESCRIPTION: SEQ ID NO: 18:

GGG GCT TGG CAT TGG CGT CAT CGT ATT CCT CTT CAG CTT GCT GCT GGT     48
```

```
Gly Ala Trp His Trp Arg His Arg Ile Pro Leu Gln Leu Ala Ala Gly
 1               5                  10                  15

CGT GGG GCC                                                          57
Arg Gly Ala
```

(2) INFORMATION FOR SEQ ID NO: 19:

(i) SEQUENCE CHARACTERISTICS:
        (A) LENGTH: 19 amino acids
        (B) TYPE: amino acid
        (D) TOPOLOGY: linear (ii) MOLECULE TYPE: protein (xi) SEQUENCE DESCRIPTION: SEQ ID NO: 19:

```
Gly Ala Trp His Trp Arg His Arg Ile Pro Leu Gln Leu Ala Ala Gly
 1               5                  10                  15

Arg Gly Ala
```

(2) INFORMATION FOR SEQ ID NO: 20:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..57

(xi) SEQUENCE DESCRIPTION: SEQ ID NO: 20:

```
GGG GCT CAG GTG GCT GTT TTG TAT CCT CCT TTG GCT GAT GCT ACT GAG    48
Gly Ala Gln Val Ala Val Leu Tyr Pro Pro Leu Ala Asp Ala Thr Glu
 1               5                  10                  15

CTT GGG GCC                                                          57
Leu Gly Ala
```

(2) INFORMATION FOR SEQ ID NO: 21:

(i) SEQUENCE CHARACTERISTICS:
        (A) LENGTH: 19 amino acids
        (B) TYPE: amino acid
        (D) TOPOLOGY: linear (ii) MOLECULE TYPE: protein (xi) SEQUENCE DESCRIPTION: SEQ ID NO: 21:

```
Gly Ala Gln Val Ala Val Leu Tyr Pro Pro Leu Ala Asp Ala Thr Glu
 1               5                  10                  15

Leu Gly Ala
```

(2) INFORMATION FOR SEQ ID NO: 22:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..57

(xi) SEQUENCE DESCRIPTION: SEQ ID NO: 22:

```
GGG GCT CGT CGG CAT GGT AAT TTT TCT CAT TTT TTT CAT CGG TCG TTG      48
Gly Ala Arg Arg His Gly Asn Phe Ser His Phe Phe His Arg Ser Leu
 1               5                  10                  15

ATT GGG GCC                                                          57
Ile Gly Ala
```

(2) INFORMATION FOR SEQ ID NO: 23:

(i) SEQUENCE CHARACTERISTICS:
        (A) LENGTH: 19 amino acids
        (B) TYPE: amino acid
        (D) TOPOLOGY: linear (ii) MOLECULE TYPE: protein (xi) SEQUENCE DESCRIPTION: SEQ ID NO: 23:

```
Gly Ala Arg Arg His Gly Asn Phe Ser His Phe Phe His Arg Ser Leu
 1               5                  10                  15

Ile Gly Ala
```

(2) INFORMATION FOR SEQ ID NO: 24:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..57

(xi) SEQUENCE DESCRIPTION: SEQ ID NO: 24:

```
GGG GCT CGT CGG CAT GGT AAT TTT TCT CAT TTT TTT CAT CGG TCG TTG      48
Gly Ala Arg Arg His Gly Asn Phe Ser His Phe Phe His Arg Ser Leu
 1               5                  10                  15

ATT GGG GCC                                                          57
Ile Gly Ala
```

(2) INFORMATION FOR SEQ ID NO: 25:

(i) SEQUENCE CHARACTERISTICS:
        (A) LENGTH: 19 amino acids
        (B) TYPE: amino acid
        (D) TOPOLOGY: linear (ii) MOLECULE TYPE: protein (xi) SEQUENCE DESCRIPTION: SEQ ID NO: 25:

```
Gly Ala Arg Arg His Gly Asn Phe Ser His Phe Phe His Arg Ser Leu
 1               5                  10                  15

Ile Gly Ala
```

(2) INFORMATION FOR SEQ ID NO: 26:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: cDNA (ix) FEATURE:

(A) NAME/KEY: CDS
        (B) LOCATION: 1..57

(xi) SEQUENCE DESCRIPTION: SEQ ID NO: 26:

GGG GCT TGG CGT ATG TAT TTT TCT CAT CGT CAT GCG CAT CTT CGT AGT    48
Gly Ala Trp Arg Met Tyr Phe Ser His Arg His Ala His Leu Arg Ser
 1               5                  10                  15

CCT GGG GCC                                                        57
Pro Gly Ala (2) INFORMATION FOR SEQ ID NO: 27:

(i) SEQUENCE CHARACTERISTICS:
        (A) LENGTH: 19 amino acids
        (B) TYPE: amino acid
        (D) TOPOLOGY: linear (ii) MOLECULE TYPE: protein (xi) SEQUENCE DESCRIPTION: SEQ ID NO: 27:

Gly Ala Trp Arg Met Tyr Phe Ser His Arg His Ala His Leu Arg Ser
 1               5                  10                  15

Pro Gly Ala (2) INFORMATION FOR SEQ ID NO: 28:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..57

(xi) SEQUENCE DESCRIPTION: SEQ ID NO: 28:

GGG GCT TGG CGT ATG TAT TTT TCT CAT CGT CAT GCG CAT CTT CGT AGT    48
Gly Ala Trp Arg Met Tyr Phe Ser His Arg His Ala His Leu Arg Ser
 1               5                  10                  15

CCT GGG GCC                                                        57
Pro Gly Ala (2) INFORMATION FOR SEQ ID NO: 29:

(i) SEQUENCE CHARACTERISTICS:
        (A) LENGTH: 19 amino acids
        (B) TYPE: amino acid
        (D) TOPOLOGY: linear (ii) MOLECULE TYPE: protein (xi) SEQUENCE DESCRIPTION: SEQ ID NO: 29:

Gly Ala Trp Arg Met Tyr Phe Ser His Arg His Ala His Leu Arg Ser
 1               5                  10                  15

Pro Gly Ala (2) INFORMATION FOR SEQ ID NO: 30:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: cDNA (ix) FEATURE:
             (A) NAME/KEY: CDS
             (B) LOCATION: 1..57

(xi) SEQUENCE DESCRIPTION: SEQ ID NO: 30:

```
GGG GCT TGG CGG AAG TAT TTT TCT TAT CAT CAT GCG CAT CTT TGT AGT         48
Gly Ala Trp Arg Lys Tyr Phe Ser Tyr His His Ala His Leu Cys Ser
 1               5                  10                  15

CCT GGG GCC                                                             57
Pro Gly Ala
```

(2) INFORMATION FOR SEQ ID NO: 31:

(i) SEQUENCE CHARACTERISTICS:
             (A) LENGTH: 19 amino acids
             (B) TYPE: amino acid
             (D) TOPOLOGY: linear (ii) MOLECULE TYPE: protein (xi) SEQUENCE DESCRIPTION: SEQ ID NO: 31:

```
Gly Ala Trp Arg Lys Tyr Phe Ser Tyr His His Ala His Leu Cys Ser
 1               5                  10                  15

Pro Gly Ala
```

(2) INFORMATION FOR SEQ ID NO: 32:

(i) SEQUENCE CHARACTERISTICS:
             (A) LENGTH: 57 base pairs
             (B) TYPE: nucleic acid
             (C) STRANDEDNESS: single
             (D) TOPOLOGY: linear (ii) MOLECULE TYPE: cDNA (ix) FEATURE:
             (A) NAME/KEY: CDS
             (B) LOCATION: 1..57

(xi) SEQUENCE DESCRIPTION: SEQ ID NO: 32:

```
GGG GCT TGG CGT ATG TAT TTT TCT CAT CGT CAT GCG CAT CTT CGT AGT         48
Gly Ala Trp Arg Met Tyr Phe Ser His Arg His Ala His Leu Arg Ser
 1               5                  10                  15

CCT GGG GCC                                                             57
Pro Gly Ala
```

(2) INFORMATION FOR SEQ ID NO: 33:

(i) SEQUENCE CHARACTERISTICS:
             (A) LENGTH: 19 amino acids
             (B) TYPE: amino acid
             (D) TOPOLOGY: linear (ii) MOLECULE TYPE: protein (xi) SEQUENCE DESCRIPTION: SEQ ID NO: 33:

```
Gly Ala Trp Arg Met Tyr Phe Ser His Arg His Ala His Leu Arg Ser
 1               5                  10                  15

Pro Gly Ala
```

(2) INFORMATION FOR SEQ ID NO: 34:

(i) SEQUENCE CHARACTERISTICS:
             (A) LENGTH: 57 base pairs
             (B) TYPE: nucleic acid

```
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..57

(xi) SEQUENCE DESCRIPTION: SEQ ID NO: 34:

GGG GCT TGG CGT ATG TAT TTT TCT CAT CGT CAT GCG CAT CTT CGT AGT        48
Gly Ala Trp Arg Met Tyr Phe Ser His Arg His Ala His Leu Arg Ser
 1               5                  10                  15

CCT GGG GCC                                                            57
Pro Gly Ala (2) INFORMATION FOR SEQ ID NO: 35:

(i) SEQUENCE CHARACTERISTICS:
        (A) LENGTH: 19 amino acids
        (B) TYPE: amino acid
        (D) TOPOLOGY: linear (ii) MOLECULE TYPE: protein (xi) SEQUENCE DESCRIPTION: SEQ ID NO: 35:

Gly Ala Trp Arg Met Tyr Phe Ser His Arg His Ala His Leu Arg Ser
 1               5                  10                  15

Pro Gly Ala (2) INFORMATION FOR SEQ ID NO: 36:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..57

(xi) SEQUENCE DESCRIPTION: SEQ ID NO: 36:

GGG GCT TGG CGT ATG TAT TTT TCT CAT CGT CAT GCG CAT CTT CGT AGT        48
Gly Ala Trp Arg Met Tyr Phe Ser His Arg His Ala His Leu Arg Ser
 1               5                  10                  15

CCT GGG GCC                                                            57
Pro Gly Ala (2) INFORMATION FOR SEQ ID NO: 37:

(i) SEQUENCE CHARACTERISTICS:
        (A) LENGTH: 19 amino acids
        (B) TYPE: amino acid
        (D) TOPOLOGY: linear (ii) MOLECULE TYPE: protein (xi) SEQUENCE DESCRIPTION: SEQ ID NO: 37:

Gly Ala Trp Arg Met Tyr Phe Ser His Arg His Ala His Leu Arg Ser
 1               5                  10                  15

Pro Gly Ala (2) INFORMATION FOR SEQ ID NO: 38:
```

(i) SEQUENCE CHARACTERISTICS:
            (A) LENGTH: 57 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: CDS
            (B) LOCATION: 1..57

(xi) SEQUENCE DESCRIPTION: SEQ ID NO: 38:

```
GGG GCT CGT CGG CAT GGT AAT TTT TCT CAT TTT TTT CAT CGG TCG TTG       48
Gly Ala Arg Arg His Gly Asn Phe Ser His Phe Phe His Arg Ser Leu
 1               5                  10                  15

ATT GGG GCC                                                           57
Ile Gly Ala
```

(2) INFORMATION FOR SEQ ID NO: 39:

(i) SEQUENCE CHARACTERISTICS:
            (A) LENGTH: 19 amino acids
            (B) TYPE: amino acid
            (D) TOPOLOGY: linear (ii) MOLECULE TYPE: protein (xi) SEQUENCE DESCRIPTION: SEQ ID NO: 39:

```
Gly Ala Arg Arg His Gly Asn Phe Ser His Phe Phe His Arg Ser Leu
 1               5                  10                  15

Ile Gly Ala
```

(2) INFORMATION FOR SEQ ID NO: 40:

(i) SEQUENCE CHARACTERISTICS:
            (A) LENGTH: 57 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: CDS
            (B) LOCATION: 1..57

(xi) SEQUENCE DESCRIPTION: SEQ ID NO: 40:

```
GGG GCT TGG CAT TGG CGT CAT CGT ATT CCT CTT CAG CTT GCT GCT GGT       48
Gly Ala Trp His Trp Arg His Arg Ile Pro Leu Gln Leu Ala Ala Gly
 1               5                  10                  15

CGT GGG GCC                                                           57
Arg Gly Ala
```

(2) INFORMATION FOR SEQ ID NO: 41:

(i) SEQUENCE CHARACTERISTICS:
            (A) LENGTH: 19 amino acids
            (B) TYPE: amino acid
            (D) TOPOLOGY: linear (ii) MOLECULE TYPE: protein (xi) SEQUENCE DESCRIPTION: SEQ ID NO: 41:

```
Gly Ala Trp His Trp Arg His Arg Ile Pro Leu Gln Leu Ala Ala Gly
 1               5                  10                  15

Arg Gly Ala
```

(2) INFORMATION FOR SEQ ID NO: 42:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..57

(xi) SEQUENCE DESCRIPTION: SEQ ID NO: 42:

```
GGG GCT CGT CGG CAT GGT AAT TTT TCT CAT TTT TTT CAT CGG TCG TTG    48
Gly Ala Arg Arg His Gly Asn Phe Ser His Phe Phe His Arg Ser Leu
  1               5                  10                  15

ATT GGG GCC                                                       57
Ile Gly Ala
```

(2) INFORMATION FOR SEQ ID NO: 43:

(i) SEQUENCE CHARACTERISTICS:
        (A) LENGTH: 19 amino acids
        (B) TYPE: amino acid
        (D) TOPOLOGY: linear (ii) MOLECULE TYPE: protein (xi) SEQUENCE DESCRIPTION: SEQ ID NO: 43:

```
Gly Ala Arg Arg His Gly Asn Phe Ser His Phe Phe His Arg Ser Leu
  1               5                  10                  15

Ile Gly Ala
```

(2) INFORMATION FOR SEQ ID NO: 44:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..57

(xi) SEQUENCE DESCRIPTION: SEQ ID NO: 44:

```
GGG GCT GAT TGG ATT ACT TTT CAT CGT CGT CAT CAT GAT CGT GTT CTT    48
Gly Ala Asp Trp Ile Thr Phe His Arg Arg His His Asp Arg Val Leu
  1               5                  10                  15

TCT GGG GCC                                                       57
Ser Gly Ala
```

(2) INFORMATION FOR SEQ ID NO: 45:

(i) SEQUENCE CHARACTERISTICS:
        (A) LENGTH: 19 amino acids
        (B) TYPE: amino acid
        (D) TOPOLOGY: linear (ii) MOLECULE TYPE: protein (xi) SEQUENCE DESCRIPTION: SEQ ID NO: 45:

```
Gly Ala Asp Trp Ile Thr Phe His Arg Arg His His Asp Arg Val Leu
  1               5                  10                  15
```

Ser Gly Ala (2) INFORMATION FOR SEQ ID NO: 46:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..57

(xi) SEQUENCE DESCRIPTION: SEQ ID NO: 46:

```
GGG GCT GGT TGG ATT ACT TTT CAT CGT CGT CAT CAT GAT CGT GTT CTT      48
Gly Ala Gly Trp Ile Thr Phe His Arg Arg His His Asp Arg Val Leu
 1               5                  10                  15

TCT GGG GCC                                                          57
Ser Gly Ala
```

(2) INFORMATION FOR SEQ ID NO: 47:

(i) SEQUENCE CHARACTERISTICS:
        (A) LENGTH: 19 amino acids
        (B) TYPE: amino acid
        (D) TOPOLOGY: linear (ii) MOLECULE TYPE: protein (xi) SEQUENCE DESCRIPTION: SEQ ID NO: 47:

```
Gly Ala Gly Trp Ile Thr Phe His Arg Arg His His Asp Arg Val Leu
 1               5                  10                  15

Ser Gly Ala
```

(2) INFORMATION FOR SEQ ID NO: 48:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..57

(xi) SEQUENCE DESCRIPTION: SEQ ID NO: 48:

```
GGG GCT GGG AAG GCT ATG TTT AGT CAT TCT TAT CGT CAT CGG GGT TCG      48
Gly Ala Gly Lys Ala Met Phe Ser His Ser Tyr Arg His Arg Gly Ser
 1               5                  10                  15

GCT GGG GCC                                                          57
Ala Gly Ala
```

(2) INFORMATION FOR SEQ ID NO: 49:

(i) SEQUENCE CHARACTERISTICS:
        (A) LENGTH: 19 amino acids
        (B) TYPE: amino acid
        (D) TOPOLOGY: linear (ii) MOLECULE TYPE: protein (xi) SEQUENCE DESCRIPTION: SEQ ID NO: 49:

```
Gly Ala Gly Lys Ala Met Phe Ser His Ser Tyr Arg His Arg Gly Ser
 1               5                  10                  15

Ala Gly Ala
```

(2) INFORMATION FOR SEQ ID NO: 50:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..57

(xi) SEQUENCE DESCRIPTION: SEQ ID NO: 50:

```
GGG GCT GAT TGG ATT ACT TTT CAT CGT CGT CAT CAT GAT CGT GTT CTT          48
Gly Ala Asp Trp Ile Thr Phe His Arg Arg His His Asp Arg Val Leu
 1               5                  10                  15

TCT GGG GCC                                                              57
Ser Gly Ala
```

(2) INFORMATION FOR SEQ ID NO: 51:

(i) SEQUENCE CHARACTERISTICS:
        (A) LENGTH: 19 amino acids
        (B) TYPE: amino acid
        (D) TOPOLOGY: linear (ii) MOLECULE TYPE: protein (xi) SEQUENCE DESCRIPTION: SEQ ID NO: 51:

```
Gly Ala Asp Trp Ile Thr Phe His Arg Arg His His Asp Arg Val Leu
 1               5                  10                  15

Ser Gly Ala
```

(2) INFORMATION FOR SEQ ID NO: 52:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..57

(xi) SEQUENCE DESCRIPTION: SEQ ID NO: 52:

```
GGG GCT AGT CGT CAT ATG CTT GCT CGG TGG TCG CGT TTG CTT GCT GTT          48
Gly Ala Ser Arg His Met Leu Ala Arg Trp Ser Arg Leu Leu Ala Val
 1               5                  10                  15

CCT GGG GCC                                                              57
Pro Gly Ala
```

(2) INFORMATION FOR SEQ ID NO: 53:

(i) SEQUENCE CHARACTERISTICS:
        (A) LENGTH: 19 amino acids
        (B) TYPE: amino acid
        (D) TOPOLOGY: linear -continued (ii) MOLECULE TYPE: protein (xi) SEQUENCE DESCRIPTION: SEQ ID NO: 53:

Gly Ala Ser Arg His Met Leu Ala Arg Trp Ser Arg Leu Leu Ala Val
 1               5                  10                  15

Pro Gly Ala (2) INFORMATION FOR SEQ ID NO: 54:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..57

(xi) SEQUENCE DESCRIPTION: SEQ ID NO: 54:

GGG GCT GGG AAG GCT ATG TTT AGT CAT TCT TAT CGT CAT CGG GGT TCG        48
Gly Ala Gly Lys Ala Met Phe Ser His Ser Tyr Arg His Arg Gly Ser
 1               5                  10                  15

GCT GGG GCC                                                            57
Ala Gly Ala (2) INFORMATION FOR SEQ ID NO: 55:

(i) SEQUENCE CHARACTERISTICS:
        (A) LENGTH: 19 amino acids
        (B) TYPE: amino acid
        (D) TOPOLOGY: linear (ii) MOLECULE TYPE: protein (xi) SEQUENCE DESCRIPTION: SEQ ID NO: 55:

Gly Ala Gly Lys Ala Met Phe Ser His Ser Tyr Arg His Arg Gly Ser
 1               5                  10                  15

Ala Gly Ala (2) INFORMATION FOR SEQ ID NO: 56:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..57

(xi) SEQUENCE DESCRIPTION: SEQ ID NO: 56:

GGG GCT TGG CAT TGG CGT CAT CGT ATT CCT CTT CAG CTT GCT GCT GGT        48
Gly Ala Trp His Trp Arg His Arg Ile Pro Leu Gln Leu Ala Ala Gly
 1               5                  10                  15

CGT GGG GCC                                                            57
Arg Gly Ala (2) INFORMATION FOR SEQ ID NO: 57:

(i) SEQUENCE CHARACTERISTICS:
        (A) LENGTH: 19 amino acids (B) TYPE: amino acid
        (D) TOPOLOGY: linear (ii) MOLECULE TYPE: protein (xi) SEQUENCE DESCRIPTION: SEQ ID NO: 57:

Gly Ala Trp His Trp Arg His Arg Ile Pro Leu Gln Leu Ala Ala Gly
 1               5                  10                  15

Arg Gly Ala (2) INFORMATION FOR SEQ ID NO: 58:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..57

(xi) SEQUENCE DESCRIPTION: SEQ ID NO: 58:

GGG GCT CGT CGG CAT GGT AAT TTT TCT CAT TTT TTT CAT CGG TCG TTG     48
Gly Ala Arg Arg His Gly Asn Phe Ser His Phe Phe His Arg Ser Leu
 1               5                  10                  15

ATT GGG GCC                                                         57
Ile Gly Ala (2) INFORMATION FOR SEQ ID NO: 59:

(i) SEQUENCE CHARACTERISTICS:
        (A) LENGTH: 19 amino acids
        (B) TYPE: amino acid
        (D) TOPOLOGY: linear (ii) MOLECULE TYPE: protein (xi) SEQUENCE DESCRIPTION: SEQ ID NO: 59:

Gly Ala Arg Arg His Gly Asn Phe Ser His Phe Phe His Arg Ser Leu
 1               5                  10                  15

Ile Gly Ala (2) INFORMATION FOR SEQ ID NO: 60:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..57

(xi) SEQUENCE DESCRIPTION: SEQ ID NO: 60:

GGG GCT TGG AAG GCT TTG TTT AGT CAT TCT TAT CGT CCT CGG GGT TCG     48
Gly Ala Trp Lys Ala Leu Phe Ser His Ser Tyr Arg Pro Arg Gly Ser
 1               5                  10                  15

GCT GGG GCC                                                         57
Ala Gly Ala (2) INFORMATION FOR SEQ ID NO: 61:

(i) SEQUENCE CHARACTERISTICS:
        (A) LENGTH: 19 amino acids
        (B) TYPE: amino acid
        (D) TOPOLOGY: linear (ii) MOLECULE TYPE: protein (xi) SEQUENCE DESCRIPTION: SEQ ID NO: 61:

Gly Ala Trp Lys Ala Leu Phe Ser His Ser Tyr Arg Pro Arg Gly Ser
1               5                   10                  15

Ala Gly Ala (2) INFORMATION FOR SEQ ID NO: 62:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..57

(xi) SEQUENCE DESCRIPTION: SEQ ID NO: 62:

GGG GCT CAG GTG GCT GTT TTG TAT CCT CCT TTG GCT GAT GCT ACT GAG       48
Gly Ala Gln Val Ala Val Leu Tyr Pro Pro Leu Ala Asp Ala Thr Glu
1               5                   10                  15

CTT GGG GCC                                                           57
Leu Gly Ala (2) INFORMATION FOR SEQ ID NO: 63:

(i) SEQUENCE CHARACTERISTICS:
        (A) LENGTH: 19 amino acids
        (B) TYPE: amino acid
        (D) TOPOLOGY: linear (ii) MOLECULE TYPE: protein (xi) SEQUENCE DESCRIPTION: SEQ ID NO: 63:

Gly Ala Gln Val Ala Val Leu Tyr Pro Pro Leu Ala Asp Ala Thr Glu
1               5                   10                  15

Leu Gly Ala (2) INFORMATION FOR SEQ ID NO: 64:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..57

(xi) SEQUENCE DESCRIPTION: SEQ ID NO: 64:

GGG GCT TGG CGT ATG TAT TTT TCT CAT CGT CAT GCG CAT CTT CGT AGT       48
Gly Ala Trp Arg Met Tyr Phe Ser His Arg His Ala His Leu Arg Ser
1               5                   10                  15

CCT GGG GCC                                                           57
Pro Gly Ala (2) INFORMATION FOR SEQ ID NO: 65:

(i) SEQUENCE CHARACTERISTICS:
        (A) LENGTH: 19 amino acids
        (B) TYPE: amino acid
        (D) TOPOLOGY: linear (ii) MOLECULE TYPE: protein (xi) SEQUENCE DESCRIPTION: SEQ ID NO: 65:

```
Gly Ala Trp Arg Met Tyr Phe Ser His Arg His Ala His Leu Arg Ser
 1               5                  10                  15
Pro Gly Ala
```

(2) INFORMATION FOR SEQ ID NO: 66:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..30

(xi) SEQUENCE DESCRIPTION: SEQ ID NO: 66:

```
GGG GCT CAT GCG GAT AGG GTT TAT GGG GCC                        30
Gly Ala His Ala Asp Arg Val Tyr Gly Ala
 1               5                  10
```

(2) INFORMATION FOR SEQ ID NO: 67:

(i) SEQUENCE CHARACTERISTICS:
        (A) LENGTH: 10 amino acids
        (B) TYPE: amino acid
        (D) TOPOLOGY: linear (ii) MOLECULE TYPE: protein (xi) SEQUENCE DESCRIPTION: SEQ ID NO: 67:

```
Gly Ala His Ala Asp Arg Val Tyr Gly Ala
 1               5                  10
```

(2) INFORMATION FOR SEQ ID NO: 68:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 68:

```
ATTTCAGGCC CAGCCGGCCA TGGCCGARGT RMAGCTKSAK GAGWC            45
```

(2) INFORMATION FOR SEQ ID NO: 69:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: other nucleic acid
            (A) DESCRIPTION: /desc = "primer"

(xi) SEQUENCE DESCRIPTION: SEQ ID NO: 69:

ATTTCAGGCC CAGCCGGCCA TGGCCGARGT YCARCTKCAR CARYC                45

(2) INFORMATION FOR SEQ ID NO: 70:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 70:

ATTTCAGGCC CAGCCGGCCA TGGCCCAGGT GAAGCTKSTS GARTC                45

(2) INFORMATION FOR SEQ ID NO: 71:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 71:

ATTTCAGGCC CAGCCGGCCA TGGCCGAVGT GMWGCTKGTG GAGWC                45

(2) INFORMATION FOR SEQ ID NO: 72:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 72:

ATTTCAGGCC CAGCCGGCCA TGGCCCAGGT BCARCTKMAR SARTC                45

(2) INFORMATION FOR SEQ ID NO: 73:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 73:

GCTGCCACCG CCACCTGMRG AGACDGTGAS TGARG                           35

(2) INFORMATION FOR SEQ ID NO: 74:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
            (A) DESCRIPTION: /desc = "primer"

(xi) SEQUENCE DESCRIPTION: SEQ ID NO: 74:

GCTGCCACCG CCACCTGMRG AGACDGTGAS MGTRG                                    35

(2) INFORMATION FOR SEQ ID NO: 75:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(xi) SEQUENCE DESCRIPTION: SEQ ID NO: 75:

GCTGCCACCG CCACCTGMRG AGACDGTGAS CAGRG                                    35

(2) INFORMATION FOR SEQ ID NO: 76:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(xi) SEQUENCE DESCRIPTION: SEQ ID NO: 76:

CCCGGGCCAC CATGGAGACA GACACACTCC TG                                       32

(2) INFORMATION FOR SEQ ID NO: 77:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(xi) SEQUENCE DESCRIPTION: SEQ ID NO: 77:

CCCGGGCCAC CATGGATTTT CAAGTGCAGA TTTTC                                    35

(2) INFORMATION FOR SEQ ID NO: 78:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(xi) SEQUENCE DESCRIPTION: SEQ ID NO: 78:

CCCGGGCCAC CATGGAGWCA CAKWCTCAGG TC                                       32

(2) INFORMATION FOR SEQ ID NO: 79:

(i) SEQUENCE CHARACTERISTICS:
            (A) LENGTH: 33 base pairs
            (B) TYPE: nucleic acid
            (C) STRANDEDNESS: single (D) TOPOLOGY: linear (ii) MOLECULE TYPE: other nucleic acid
       (A) DESCRIPTION: /desc = "primer"

(xi) SEQUENCE DESCRIPTION: SEQ ID NO: 79:

CCCGGGCCAC CATGKCCCCW RCTCAGYTTC TKG					33

(2) INFORMATION FOR SEQ ID NO: 80:

(i) SEQUENCE CHARACTERISTICS:
       (A) LENGTH: 31 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "primer"

(xi) SEQUENCE DESCRIPTION: SEQ ID NO: 80:

CCCGGGCACC ATGAAGTTGC CTGTTAGGCT G					31

(2) INFORMATION FOR SEQ ID NO: 81:

(i) SEQUENCE CHARACTERISTICS:
       (A) LENGTH: 23 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "primer"

(xi) SEQUENCE DESCRIPTION: SEQ ID NO: 81:

GCACCTCCAG ATGTTAACTG CTC					23

(2) INFORMATION FOR SEQ ID NO: 82:

(i) SEQUENCE CHARACTERISTICS:
       (A) LENGTH: 54 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "primer"

(xi) SEQUENCE DESCRIPTION: SEQ ID NO: 82:

TAATATCGCG ACAGCTACAG GTGTCCACTC CCGAAGTGAT GCTGGTGGAG WCTG					54

(2) INFORMATION FOR SEQ ID NO: 83:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "primer"

(xi) SEQUENCE DESCRIPTION: SEQ ID NO: 83:

TTATAGAATT CTGAGGAGAC GGTGAGTGAG					30

(2) INFORMATION FOR SEQ ID NO: 84:

(i) SEQUENCE CHARACTERISTICS:
       (A) LENGTH: 29 base pairs
       (B) TYPE: nucleic acid (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 84:

TTAGGCGATA TCGTTCTCTC CCAGTCTCC                                                      29

(2) INFORMATION FOR SEQ ID NO: 85:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 85:

GTAACCGTTC GAAAAGTGTA CTTACGTTTT ATTTCCAGCA TGGTCC                                   46

(2) INFORMATION FOR SEQ ID NO: 86:

(i) SEQUENCE CHARACTERISTICS:
        (A) LENGTH: 369 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..369

(xi) SEQUENCE DESCRIPTION: SEQ ID NO: 86:

GAA GTG ATG CTG GTG GAG TCT GGT GGA GGA TTG GTG CAG CCT AAA GGG              48
Glu Val Met Leu Val Glu Ser Gly Gly Gly Leu Val Gln Pro Lys Gly
 1               5                  10                  15

TCA TTG AAA CTC TCA TGT GCA GCC TCT GGA TTC ACC TTC AAT AAC TAC              96
Ser Leu Lys Leu Ser Cys Ala Ala Ser Gly Phe Thr Phe Asn Asn Tyr
            20                  25                  30

GCC ATG AAT TGG GTC CGC CAG GCT CCA GGA AAG GGT TTG GAA TGG GTT             144
Ala Met Asn Trp Val Arg Gln Ala Pro Gly Lys Gly Leu Glu Trp Val
        35                  40                  45

GCT CGC ATA AGA AGT AAA AGT AAT AAT TAT GCA ACA TTT TAT GCC GAT             192
Ala Arg Ile Arg Ser Lys Ser Asn Asn Tyr Ala Thr Phe Tyr Ala Asp
    50                  55                  60

TCA GTG AAA GAC AGG TTC ACC ATC TCC AGA GAT GAT TCA CAA AGC ATG             240
Ser Val Lys Asp Arg Phe Thr Ile Ser Arg Asp Asp Ser Gln Ser Met
65                  70                  75                  80

CTC TAT CTG CAA ATG AAC AAC TTG AAA ACT GAG GAC ACA GCC ATG TAT             288
Leu Tyr Leu Gln Met Asn Asn Leu Lys Thr Glu Asp Thr Ala Met Tyr
                85                  90                  95

TAC TGT GTG AGA CGG GGG GCT TCA GGG ATT GAC TAT GCT ATG GAC TAC             336
Tyr Cys Val Arg Arg Gly Ala Ser Gly Ile Asp Tyr Ala Met Asp Tyr
            100                 105                 110

TGG GGT CAA GGA ACC TCA CTC ACC GTC TCC TCA                                 369
Trp Gly Gln Gly Thr Ser Leu Thr Val Ser Ser
        115                 120

(2) INFORMATION FOR SEQ ID NO: 87:

(i) SEQUENCE CHARACTERISTICS:

(A) LENGTH: 123 amino acids
        (B) TYPE: amino acid
        (D) TOPOLOGY: linear (ii) MOLECULE TYPE: protein (xi) SEQUENCE DESCRIPTION: SEQ ID NO: 87:

Glu Val Met Leu Val Glu Ser Gly Gly Gly Leu Val Gln Pro Lys Gly
 1               5                  10                  15

Ser Leu Lys Leu Ser Cys Ala Ala Ser Gly Phe Thr Phe Asn Asn Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Phe Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Arg Gly Ala Ser Gly Ile Asp Tyr Ala Met Asp Tyr
            100                 105                 110

Trp Gly Gln Gly Thr Ser Leu Thr Val Ser Ser
        115                 120

(2) INFORMATION FOR SEQ ID NO: 88:

(i) SEQUENCE CHARACTERISTICS:
        (A) LENGTH: 318 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..318

(xi) SEQUENCE DESCRIPTION: SEQ ID NO: 88:

CAA ATT GTT CTC TCC CAG TCT CCA GCA ATC CTG TCT GCA TCT CCA GGG      48
Gln Ile Val Leu Ser Gln Ser Pro Ala Ile Leu Ser Ala Ser Pro Gly
 1               5                  10                  15

GAA AAG GTC ACA ATG ACT TGC AGG GCC AGC TCA AGT GTA AAT TAC ATG      96
Glu Lys Val Thr Met Thr Cys Arg Ala Ser Ser Ser Val Asn Tyr Met
            20                  25                  30

CAC TGG TAC CAG CAG AAG CCA GGA TCC TCC CCC AAA CCC TGG ATT TCT     144
His Trp Tyr Gln Gln Lys Pro Gly Ser Ser Pro Lys Pro Trp Ile Ser
        35                  40                  45

GCC ACA TCC AAC CTG GCT TCT GGA GTC CCT GCT CGC TTC AGT GGC AGT     192
Ala Thr Ser Asn Leu Ala Ser Gly Val Pro Ala Arg Phe Ser Gly Ser
    50                  55                  60

GGG TCT GGG ACC TCT TAC TCT CTC ACA ATC AGC AGA GTG GAG GCT GAA     240
Gly Ser Gly Thr Ser Tyr Ser Leu Thr Ile Ser Arg Val Glu Ala Glu
65                  70                  75                  80

GAT GCT GCC ACT TAT TAC TGC CAG CAG TGG AGT AGT AAC CCA CCC ACG     288
Asp Ala Ala Thr Tyr Tyr Cys Gln Gln Trp Ser Ser Asn Pro Pro Thr
                85                  90                  95

TTC GGA GGG GGG ACC ATG CTG GAA ATA AGA                             318
Phe Gly Gly Gly Thr Met Leu Glu Ile Arg
            100                 105

(2) INFORMATION FOR SEQ ID NO: 89:

```
    (i) SEQUENCE CHARACTERISTICS:
        (A) LENGTH: 106 amino acids
        (B) TYPE: amino acid
        (D) TOPOLOGY: linear (ii) MOLECULE TYPE: protein (xi) SEQUENCE DESCRIPTION: SEQ ID NO: 89:

Gln Ile Val Leu Ser Gln Ser Pro Ala Ile Leu Ser Ala Ser Pro Gly
 1               5                  10                  15

Glu Lys Val Thr Met Thr Cys Arg Ala Ser Ser Ser Val Asn Tyr Met
                20                  25                  30

His Trp Tyr Gln Gln Lys Pro Gly Ser Ser Pro Lys Pro Trp Ile Ser
            35                  40                  45

Ala Thr Ser Asn Leu Ala Ser Gly Val Pro Ala Arg Phe Ser Gly Ser
        50                  55                  60

Gly Ser Gly Thr Ser Tyr Ser Leu Thr Ile Ser Arg Val Glu Ala Glu
 65                  70                  75                  80

Asp Ala Ala Thr Tyr Tyr Cys Gln Gln Trp Ser Ser Asn Pro Pro Thr
                85                  90                  95

Phe Gly Gly Gly Thr Met Leu Glu Ile Arg
                100                 105
```

We claim:

1. A humanized antibody or an antigen-binding fragment thereof having binding specificity to LTA of Gram positive bacteria, the humanized antibody comprising:
   (i) a light chain comprising three complementarity determining regions (CDRs) from the immunoglobulin light chain variable region sequence set forth as SEQ ID NO:89, and framework regions from a human acceptor immunoglobulin light chain; and
   (ii) a heavy chain comprising three complementarity determining regions (CDRs) from the immunoglobulin heavy chain variable region sequence set forth as SEQ ID NO:87, and framework regions from a human acceptor immunoglobulin heavy chain.

2. The humanized antibody of claim 1, which enhances opsonization of Gram-positive bacteria over background as compared to an appropriate control in an in vitro opsonization assay.

3. The humanized antibody of claim 2, wherein the opsonization assay is performed in the presence of complement, cells, a cell line, or a combination thereof.

4. The humanized antibody of claim 3, wherein the complement or cells or both are human in origin.

5. The humanized antibody of claim 3, wherein the cells are phagocytic cells.

6. The humanized antibody of claim 3, wherein the cells are macrophages, monocytes, neutrophils, or combinations thereof.

7. The humanized antibody of claim 3, wherein the opsonization is measured by measuring opsonophagocytic bactericidal activity.

8. The humanized antibody or antigen-binding fragment thereof of claim 1, wherein the antibody binds LTA of Gram positive bacteria fixed to a solid support.

9. The humanized antibody or antigen-binding fragment thereof of claim 8, wherein the solid support is a plate well, bead, or a micro-bead.

10. The humanized antibody of claim 1, which confers a statistically significant enhancement of survival or reduced bacteremia in an animal model.

11. The humanized antibody of claim 10, wherein the statistically significant enhancement of survival in an animal model is 25% or greater.

12. The humanized antibody of claim 10, wherein the statistically significant enhancement of survival in an animal model is 50% or greater.

13. The humanized antibody of claim 10, wherein the statistically significant enhancement of survival in an animal model is 70% or greater.

14. The humanized antibody of claim 10, wherein the statistically significant enhancement of survival in an animal model is 76% or greater.

15. The humanized antibody of claim 10, wherein the statistically significant enhancement of survival in an animal model is 90% or greater.

16. The humanized antibody of claim 10, wherein the statistically significant enhancement of survival in an animal model is between 67% and 83%.

17. The humanized antibody of claim 10, wherein the statistically significant enhancement of survival in an animal model is between 83% and 100%.

18. The humanized antibody or antigen-binding fragment thereof of claim 1, which binds to LTA at a level that is twice background or greater.

19. The humanized antibody or antigen-binding fragment thereof of claim 1, which recognizes a peptide sequence selected from: WRMYFSHRHAHLRSP (SEQ ID NO 1); and WHWRHRIPLQLAAGR (SEQ ID NO 2).

20. The humanized antibody of claim 1, further comprising human constant regions of an IgG isotype or an IgM isotype.

21. The humanized antibody or antigen-binding fragment thereof of claim 1, which is an antigen-binding fragment selected from the group consisting of Fab, Fab', F(ab')2, or SFv.

22. The humanized antibody of claim 1, which enhances survival in an animal model by 10% or more over animals not treated with the humanized antibody.

23. A composition comprising the humanized antibody or antigen-binding fragment thereof of claim 1 and a pharmaceutically acceptable carrier.

24. The humanized antibody or antigen-binding fragment thereof of any claim 1, further comprising an amino acid substitution in the framework regions.

25. The humanized antibody or antigen-binding fragment thereof of claim 1, which is a humanized antibody which blocks the binding of gram positive bacteria to human epithelial cells.

26. The humanized antibody of claim 2, wherein the opsonization is measured by measuring opsonophagocytic activity.

27. A chimeric antibody comprising the heavy chain variable region sequence set forth as SEQ ID NO:87 and the light chain variable region sequence set forth as SEQ ID NO:89 and human constant regions.

28. The chimeric antibody of claim 27, which enhances opsonization of Gram-positive bacteria over background as compared to an appropriate control in an in vitro opsonization assay.

29. The chimeric antibody of claim 28, wherein the opsonization assay is performed in the presence of complement, cells, a cell line, or a combination thereof.

30. The chimeric antibody of claim 29, wherein the complement or cells or both are human in origin.

31. The chimeric antibody of claim 29, wherein the cells are phagocytic cells.

32. The chimeric antibody of claim 29, wherein the cells are macrophages, monocytes, neutrophils, or combinations thereof.

33. The chimeric antibody of claim 29, wherein opsonization is measured by measuring opsonophagocytic activity.

34. The chimeric antibody of claim 29, wherein opsonization is measured by measuring opsonophagocytic bactericidal activity.

35. The chimeric antibody of claim 27, wherein the antibody is capable of binding to LTA of Gram positive bacteria fixed to a solid support.

36. The chimeric antibody of claim 35, wherein the solid support is a plate well, bead, or a micro-bead.

37. The chimeric antibody of claim 27, which confers a statistically significant enhancement of survival or reduced bacteremia in an animal model.

38. The chimeric antibody of claim 37, wherein the statistically significant enhancement of survival in an animal model is 25% or greater.

39. The chimeric antibody of claim 37, wherein the statistically significant enhancement of survival in an animal model is 50% or greater.

40. The chimeric antibody of claim 37, wherein the statistically significant enhancement of survival in an animal model is 70% or greater.

41. The chimeric antibody of claim 37, wherein the statistically significant enhancement of survival in an animal model is 76% or greater.

42. The chimeric antibody of claim 37, wherein the statistically significant enhancement of survival in an animal model is 90% or greater.

43. The chimeric antibody of claim 37, wherein the statistically significant enhancement of survival in an animal model is between 67% and 83%.

44. The chimeric antibody of claim 37, wherein the statistically significant enhancement of survival in an animal model is between 83% and 100%.

45. The chimeric antibody of claim 27, which binds to LTA at a level that is twice background or greater.

46. The chimeric antibody of claim 27, which recognizes a peptide sequence selected from: WRMYFSHRHAHLRSP (SEQ ID NO 1); and WHWRHRIPLQLAAGR (SEQ ID NO 2).

47. The chimeric antibody of claim 27, in which the human constant region is of the IgG isotype or IgM isotype.

48. The chimeric antibody of claim 27, which enhances survival in an animal model by 10% or more over animals not treated with the chimeric antibody.

49. A composition comprising the chimeric antibody of claim 27 and a pharmaceutically acceptable carrier.

50. The chimeric antibody of claim 27, wherein the chimeric antibody blocks the binding of Gram positive bacteria to human epithelial cells.

51. A humanized antibody or an antigen-binding fragment thereof having binding specificity to LTA of Gram positive bacteria, the humanized antibody comprising:
(i) a light chain comprising three complementarity determining regions (CDRs) from the immunoglobulin light chain variable region sequence set forth as SEQ ID NO:89; and
(ii) a heavy chain comprising three complementarity determining regions (CDRs) from the immunoglobulin heavy chain variable region sequence set forth as SEQ ID NO:87.

52. The humanized antibody of claim 51 further comprising human constant regions of an IgG isotype or IgM isotype.

53. The humanized antibody or antigen-binding fragment thereof of 51, which is an antigen-binding fragment selected from the group consisting of Fab, Fab', F(ab')2, or SFv.

54. A composition comprising the humanized antibody or antigen-binding fragment thereof of claim 51 and a pharmaceutically acceptable carrier.

55. The humanized antibody or antigen-binding fragment thereof of claim 51, wherein the humanized antibody blocks the binding of Gram positive bacteria to human epithelial cells.

56. A chimeric antibody comprising the heavy chain variable region sequence set forth as SEQ ID NO:87 and the light chain variable region sequence set forth as SEQ ID NO:90 and human constant regions.

57. The chimeric antibody of claim 56 which enhances opsonization of Gram-positive bacteria over background as compared to an appropriate control in an in vitro opsonization assay.

58. The chimeric antibody of claim 57, wherein the opsonization assay is performed in the presence of complement, cells, a cell line, or a combination thereof.

59. The chimeric antibody of claim 58, wherein the complement or cells or both are human in origin.

60. The chimeric antibody of claim 58, wherein the cells are phagocytic cells.

61. The chimeric antibody of claim 58, wherein the cells are macrophages, monocytes, neutrophils, or combinations thereof.

62. The chimeric antibody of claim 58, wherein opsonization is measured by measuring opsonophagocytic activity.

63. The chimeric antibody of claim 58, wherein opsonization is measured by measuring opsonophagocytic bactericidal activity.

64. The chimeric antibody of claim 56, wherein the antibody is capable of binding to LTA of Gram positive bacteria fixed to a solid support.

65. The chimeric antibody of claim 64, wherein the solid support is a plate well, bead, or a micro-bead.

66. The chimeric antibody of claim 56, which confers a statistically significant enhancement of survival or reduced bacteremia in an animal model.

67. The chimeric antibody of claim 66, wherein the statistically significant enhancement of survival in an animal model is 25% or greater.

68. The chimeric antibody of claim 66, wherein the statistically significant enhancement of survival in an animal model is 50% or greater.

69. The chimeric antibody of claim 66, wherein the statistically significant enhancement of survival in an animal model is 70% or greater.

70. The chimeric antibody of claim 66, wherein the statistically significant enhancement of survival in an animal model is 76% or greater.

71. The chimeric antibody of claim 66, wherein the statistically significant enhancement of survival in an animal model is 90% or greater.

72. The chimeric antibody of claim 66, wherein the statistically significant enhancement of survival in an animal model is between 67% and 83%.

73. The chimeric antibody of claim 66, wherein the statistically significant enhancement of survival in an animal model is between 83% and 100%.

74. The chimeric antibody of claim 56, which binds to LTA at a level that is twice background or greater.

75. The chimeric antibody of claim 56, which recognizes a peptide sequence selected from: WRMYFSHRHAHLRSP (SEQ ID NO 1); and WHWRHRIPLQLAAGR (SEQ ID NO 2).

76. The chimeric antibody of claim 56, in which the human constant region is of the IgG isotype or IgM isotype.

77. The chimeric antibody of claim 56, which enhances survival in an animal model by 10% or more over animals not treated with the chimeric antibody.

78. A composition comprising the chimeric antibody of claim 56 and a pharmaceutically acceptable carrier.

79. The chimeric antibody of claim 56, wherein the chimeric antibody blocks the binding of Gram positive bacteria to human epithelial cells.

\* \* \* \* \*

UNITED STATES PATENT AND TRADEMARK OFFICE
CERTIFICATE OF CORRECTION

| | | |
|---|---|---|
| PATENT NO. | : 7,511,122 B2 | Page 1 of 1 |
| APPLICATION NO. | : 11/193440 | |
| DATED | : March 31, 2009 | |
| INVENTOR(S) | : Gerald Walter Fischer et al. | |

It is certified that error appears in the above-identified patent and that said Letters Patent is hereby corrected as shown below:

At column 77, please insert the following paragraph before the claims section:

```
(2) INFORMATION FOR SEQ ID NO: 90:

(i) SEQUENCE CHARACTERISTICS:
        (A) LENGTH:   106 amino acids
        (B) TYPE: amino acid
        (D) TOPOLOGY: linear (ii) MOLECULAR TYPE: protein (xi) SEQUENCE DESCRIPTION:   SEQ ID NO: 90:

Asp Ile Val Leu Ser Gln Ser Pro Ala Ile Leu Ser Ala Ser Pro Gly
 1               5                  10                  15

Glu Lys Val Thr Met Thr Cys Arg Ala Ser Ser Ser Val Asn Tyr Met
                20                  25                  30

His Trp Tyr Gln Gln Lys Pro Gly Ser Ser Pro Lys Pro Trp Ile Ser
            35                  40                  45

Ala Thr Ser Asn Leu Ala Ser Gly Val Pro Ala Arg Phe Ser Gly Ser
        50                  55                  60

Gly Ser Gly Thr Ser Tyr Ser Leu Thr Ile Ser Arg Val Glu Ala Glu
 65                 70                  75                  80

Asp Ala Ala Thr Tyr Tyr Cys Gln Gln Trp Ser Ser Asn Pro Pro Thr
                85                  90                  95

Phe Gly Gly Gly Thr Met Leu Glu Ile Lys
                100                 105
```

-- --

Signed and Sealed this
Fourth Day of October, 2011

David J. Kappos
*Director of the United States Patent and Trademark Office*